United States Patent
Jansen et al.

(10) Patent No.: US 11,078,548 B2
(45) Date of Patent: Aug. 3, 2021

(54) METHOD FOR PRODUCING XYLITOL BY FERMENTATION

(71) Applicant: VIRDIA, LLC, Danville, VA (US)

(72) Inventors: Robert Jansen, Collinsville, IL (US); James Alan Lawson, Ellsworth, ME (US); Adam Tyler Carden, Henderson, NC (US); Philip Travisano, Danville, VA (US); Brendon Christopher Stout, Burlington, NC (US); Noa Lapidot, Mevaseret Zion (IL)

(73) Assignee: VIRDIA, LLC, Danville, VA (US)

( * ) Notice: Subject to any disclaimer, the term of this patent is extended or adjusted under 35 U.S.C. 154(b) by 0 days.

(21) Appl. No.: 15/541,544

(22) PCT Filed: Jan. 6, 2016

(86) PCT No.: PCT/US2016/012384
§ 371 (c)(1),
(2) Date: Jul. 5, 2017

(87) PCT Pub. No.: WO2016/112134
PCT Pub. Date: Jul. 14, 2016

(65) Prior Publication Data
US 2017/0369957 A1 Dec. 28, 2017

Related U.S. Application Data

(60) Provisional application No. 62/100,791, filed on Jan. 7, 2015, provisional application No. 62/249,801, filed on Nov. 2, 2015.

(51) Int. Cl.
| | |
|---|---|
| *C12P 7/00* | (2006.01) |
| *C13K 13/00* | (2006.01) |
| *C08B 37/00* | (2006.01) |
| *C13K 1/02* | (2006.01) |
| *C13K 11/00* | (2006.01) |
| *C08H 8/00* | (2010.01) |
| *C12P 7/18* | (2006.01) |

(52) U.S. Cl.
CPC ........ *C13K 13/002* (2013.01); *C08B 37/0057* (2013.01); *C08H 8/00* (2013.01); *C12P 7/18* (2013.01); *C13K 1/02* (2013.01); *C13K 11/00* (2013.01); *C13K 13/00* (2013.01); *C13K 13/007* (2013.01)

(58) Field of Classification Search
None
See application file for complete search history.

(56) References Cited

U.S. PATENT DOCUMENTS

| | | |
|---|---|---|
| 1,344,671 A | 6/1920 | Bergius |
| 1,544,149 A | 6/1925 | Hagglund |
| 2,008,284 A | 7/1935 | Koch et al. |
| 2,239,095 A | 4/1941 | Hasche |
| 2,380,448 A | 7/1945 | Katzen |
| 2,440,442 A | 4/1948 | Hillyer et al. |
| 2,752,270 A | 6/1956 | Specht |
| 2,890,972 A | 6/1959 | Wheaton |
| 2,917,390 A | 12/1959 | Apel et al. |
| 2,944,923 A | 7/1960 | Riehm |
| 2,989,569 A | 6/1961 | Apel |
| 3,132,051 A | 5/1964 | Nobile et al. |
| 3,212,933 A | 10/1965 | Hess et al. |
| 3,616,222 A | 10/1971 | Dasinger |
| 3,839,318 A | 10/1974 | Mansfield |
| 3,990,904 A | 11/1976 | Friese et al. |
| 4,008,285 A | 2/1977 | Melaja et al. |
| 4,029,515 A | 6/1977 | Kiminki et al. |
| 4,102,705 A | 7/1978 | Pfeiffer et al. |
| 4,105,467 A | 8/1978 | Buckl et al. |
| 4,165,240 A | 8/1979 | Enokizono et al. |
| 4,174,976 A | 11/1979 | Bose et al. |
| 4,199,374 A | 4/1980 | Dwivedi et al. |
| 4,237,110 A | 12/1980 | Forster et al. |
| 4,266,981 A | 5/1981 | Tsao et al. |
| 4,277,626 A | 7/1981 | Forss et al. |
| 4,278,471 A | 7/1981 | Whittingham |
| 4,291,007 A | 9/1981 | Baniel |
| 4,299,677 A | 11/1981 | Venkatasubramanian et al. |
| 4,328,004 A | 5/1982 | Globus |
| 4,374,738 A | 2/1983 | Kelley |
| 4,382,843 A | 5/1983 | Black |
| 4,395,543 A | 7/1983 | Wang et al. |
| 4,425,136 A | 1/1984 | Pearson et al. |
| 4,445,938 A | 5/1984 | Verwaerde et al. |
| 4,470,851 A | 9/1984 | Paszner et al. |
| 4,472,501 A | 9/1984 | Takasawa et al. |
| 4,496,426 A | 1/1985 | Baumeister et al. |
| 4,503,278 A | 3/1985 | Chen et al. |

(Continued)

FOREIGN PATENT DOCUMENTS

| | | |
|---|---|---|
| CA | 2735396 A1 | 3/2010 |
| CN | 1082115 A | 2/1994 |

(Continued)

OTHER PUBLICATIONS

Rafiqul et al. (Food Reviews Int'l, vo. 29, pp. 127-156, 2013).*
Rivas (J. Agric. Food Chem., vol. 54, 2006, pp. 4430-4435).*
Co-pending U.S. Appl. No. 15/573,801, filed Nov. 13, 2017.
Co-pending U.S. Appl. No. 15/933,210, filed Mar. 22, 2018.
EP 16735376.2 Extended Search Report and Written Opinion dated May 9, 2018.
Co-pending U.S. Appl. No. 15/948,837, filed Apr. 9, 2018.
Co-pending U.S. Appl. No. 16/016,467, filed Jun. 22, 2018.

(Continued)

*Primary Examiner* — Hope A Robinson
(74) *Attorney, Agent, or Firm* — Polsinelli PC

(57) ABSTRACT

The present disclosure relates to systems, methods, and processes for the production of sugars and conversion products from biomass.

13 Claims, 12 Drawing Sheets

(56) References Cited

U.S. PATENT DOCUMENTS

| | | |
|---|---|---|
| 4,516,566 A | 5/1985 | Chao et al. |
| 4,520,105 A | 5/1985 | Sinner et al. |
| 4,525,218 A | 6/1985 | Chen et al. |
| 4,556,430 A | 12/1985 | Converse et al. |
| 4,579,595 A | 4/1986 | Sachetto et al. |
| 4,608,245 A | 8/1986 | Gaddy et al. |
| 4,612,286 A | 9/1986 | Sherman et al. |
| 4,615,742 A | 10/1986 | Wright |
| 4,631,129 A | 12/1986 | Heikkila |
| 4,677,198 A | 6/1987 | Linnett et al. |
| 4,701,414 A | 10/1987 | Van Dijken et al. |
| 4,713,413 A | 12/1987 | Tegge et al. |
| 4,746,401 A | 5/1988 | Roberts et al. |
| 4,764,596 A | 8/1988 | Lora et al. |
| 4,840,903 A | 6/1989 | Wu |
| 4,901,635 A | 2/1990 | Williams |
| 4,934,177 A | 6/1990 | Cuthbertson et al. |
| 4,966,650 A | 10/1990 | Delong et al. |
| 4,992,308 A | 2/1991 | Sunol |
| 5,028,336 A | 7/1991 | Bartels et al. |
| 5,049,494 A | 9/1991 | Allenza |
| 5,081,026 A | 1/1992 | Heikkila et al. |
| 5,114,491 A | 5/1992 | Sarhaddar |
| 5,205,473 A | 4/1993 | Coffin, Sr. |
| 5,227,446 A | 7/1993 | Denzinger et al. |
| 5,230,742 A | 7/1993 | Lillard, Jr. et al. |
| 5,244,553 A | 9/1993 | Goldstein |
| 5,332,842 A | 7/1994 | Dickakian |
| 5,370,997 A | 12/1994 | Antranikian et al. |
| 5,407,580 A | 4/1995 | Hester et al. |
| 5,411,594 A | 5/1995 | Brelsford |
| 5,421,964 A | 6/1995 | Mahler et al. |
| 5,424,417 A | 6/1995 | Torget et al. |
| 5,480,490 A | 1/1996 | Toth et al. |
| 5,538,637 A | 7/1996 | Hester et al. |
| 5,580,389 A | 12/1996 | Farone et al. |
| 5,597,714 A | 1/1997 | Farone et al. |
| 5,696,195 A | 12/1997 | Tuminello et al. |
| 5,705,369 A | 1/1998 | Torget et al. |
| 5,711,817 A | 1/1998 | Titmas |
| 5,726,046 A | 3/1998 | Farone et al. |
| 5,728,225 A | 3/1998 | Duflot et al. |
| 5,730,837 A | 3/1998 | Black et al. |
| 5,730,877 A | 3/1998 | Heikkila et al. |
| 5,782,982 A | 7/1998 | Farone et al. |
| 5,820,687 A | 10/1998 | Farone et al. |
| 5,837,831 A | 11/1998 | Gruning et al. |
| 5,846,787 A | 12/1998 | Ladisch et al. |
| 5,856,261 A | 1/1999 | Culross et al. |
| 5,865,948 A | 2/1999 | Lora et al. |
| 5,876,505 A | 3/1999 | Klyosov et al. |
| 5,969,195 A | 10/1999 | Stabel et al. |
| 5,980,640 A | 11/1999 | Nurmi et al. |
| 6,001,410 A | 12/1999 | Bolen et al. |
| 6,007,636 A | 12/1999 | Lightner |
| 6,022,419 A | 2/2000 | Torget et al. |
| 6,063,204 A | 5/2000 | Hester et al. |
| 6,086,681 A | 7/2000 | Lindroos et al. |
| 6,093,217 A | 7/2000 | Frolich et al. |
| 6,124,443 A | 9/2000 | Darsow |
| 6,136,868 A | 10/2000 | Culross et al. |
| 6,224,776 B1 | 5/2001 | Heikkilä et al. |
| 6,230,477 B1 | 5/2001 | Caillouet |
| 6,239,274 B1 | 5/2001 | Heikkilä et al. |
| 6,258,175 B1 | 7/2001 | Lightner |
| 6,391,204 B1 | 5/2002 | Russo, Jr. |
| 6,409,841 B1 | 6/2002 | Lombard |
| 6,419,788 B1 | 7/2002 | Wingerson |
| 6,419,828 B1 | 7/2002 | Russo, Jr. |
| 6,431,370 B1 | 8/2002 | Braunstein et al. |
| 6,451,123 B1 | 9/2002 | Saska et al. |
| 6,479,713 B1 | 11/2002 | Werpy et al. |
| 6,486,366 B1 | 11/2002 | Ostgard et al. |
| 6,548,662 B1 | 4/2003 | Ohsaki et al. |
| 6,572,775 B2 | 6/2003 | Heikkila et al. |
| 6,620,292 B2 | 9/2003 | Wingerson |
| 6,692,578 B2 | 2/2004 | Schmidt et al. |
| 6,747,076 B2 | 6/2004 | Schneider et al. |
| 6,752,902 B2 | 6/2004 | Heikkila et al. |
| 6,824,599 B2 | 11/2004 | Swatloski et al. |
| 6,841,085 B2 | 1/2005 | Werpy et al. |
| 6,852,345 B2 | 2/2005 | Hill et al. |
| 6,872,316 B2 | 3/2005 | Heikkila et al. |
| 6,875,349 B2 | 4/2005 | Heikkila et al. |
| 6,896,811 B2 | 5/2005 | Heikkila et al. |
| 6,924,371 B2 | 8/2005 | Karki et al. |
| 6,936,110 B2 | 8/2005 | Van Thorre et al. |
| 6,942,754 B2 | 9/2005 | Izumi et al. |
| 7,022,239 B2 | 4/2006 | Heikkila et al. |
| 7,026,152 B2 | 4/2006 | Ingram et al. |
| 7,038,094 B2 | 5/2006 | Werpy et al. |
| 7,109,005 B2 | 9/2006 | Eroma et al. |
| 7,198,925 B2 | 4/2007 | Foody |
| 7,229,558 B2 | 6/2007 | Heikkila et al. |
| 7,361,273 B2 | 4/2008 | Heikkila et al. |
| 7,399,323 B2 | 7/2008 | Renninger et al. |
| 7,465,791 B1 | 12/2008 | Hallberg et al. |
| 7,501,025 B2 | 3/2009 | Bakker et al. |
| 7,503,981 B2 | 3/2009 | Wyman et al. |
| 7,524,660 B2 | 4/2009 | Caimi et al. |
| 7,557,262 B2 | 7/2009 | Lanahan et al. |
| 7,649,086 B2 | 1/2010 | Belanger et al. |
| 7,699,958 B2 | 4/2010 | Griffith et al. |
| 7,704,381 B2 | 4/2010 | Siekmann et al. |
| 7,713,725 B2 | 5/2010 | England et al. |
| 7,717,364 B2 | 5/2010 | Wingerson |
| 7,718,070 B2 | 5/2010 | Wahnon et al. |
| 7,771,964 B2 | 8/2010 | Kim et al. |
| 7,834,092 B2 | 11/2010 | Uradnisheck et al. |
| 7,880,049 B2 | 2/2011 | Dumesic et al. |
| 7,883,882 B2 | 2/2011 | Franklin et al. |
| 7,901,511 B2 | 3/2011 | Griffin et al. |
| 7,935,156 B2 | 5/2011 | Renninger et al. |
| 7,942,940 B2 | 5/2011 | Renninger et al. |
| 7,947,858 B2 | 5/2011 | Buchert et al. |
| 7,959,811 B2 | 6/2011 | Airaksinen et al. |
| 7,977,517 B2 | 7/2011 | Cortright et al. |
| 7,993,709 B2 | 8/2011 | Brunet |
| 8,017,818 B2 | 9/2011 | Cortright et al. |
| 8,022,260 B2 | 9/2011 | O'Connor et al. |
| 8,026,378 B2 | 9/2011 | Selifonov |
| 8,030,039 B1 | 10/2011 | Retsina et al. |
| 8,052,953 B2 | 11/2011 | Chen |
| 8,053,468 B2 | 11/2011 | Selifonov |
| 8,084,508 B2 | 12/2011 | Yakobson et al. |
| 8,084,635 B2 | 12/2011 | Selifonov |
| 8,101,808 B2 | 1/2012 | Evanko et al. |
| 8,152,867 B2 | 4/2012 | Dumenil |
| 8,163,092 B2 | 4/2012 | Baniel et al. |
| 8,178,701 B2 | 5/2012 | Selifonov |
| 8,188,030 B2 | 5/2012 | Rieth et al. |
| 8,277,643 B2 | 10/2012 | Huber et al. |
| 8,382,905 B2 | 2/2013 | Takeshima et al. |
| 8,404,355 B2 | 3/2013 | Jansen et al. |
| 8,500,910 B2 | 8/2013 | Brady et al. |
| 8,637,660 B2 | 1/2014 | Fanselow et al. |
| 8,637,661 B2 | 1/2014 | Fanselow et al. |
| 8,657,960 B2 | 2/2014 | North |
| 8,685,685 B2 | 4/2014 | Retsina et al. |
| 8,722,878 B2 | 5/2014 | Raines et al. |
| 8,894,771 B2 | 11/2014 | Floyd et al. |
| 8,926,794 B2 | 1/2015 | Han et al. |
| 8,932,467 B2 | 1/2015 | Fosbol et al. |
| 8,999,065 B2 | 4/2015 | Kazachkin et al. |
| 9,115,467 B2 | 8/2015 | Jansen et al. |
| 9,200,337 B2 | 12/2015 | Colakyan et al. |
| 9,243,303 B2 | 1/2016 | Fang |
| 9,410,216 B2 | 8/2016 | Eyal et al. |
| 9,476,106 B2 | 10/2016 | Eyal et al. |
| 9,512,495 B2 | 12/2016 | Eyal et al. |
| 9,617,608 B2 | 4/2017 | Eyal et al. |
| 9,650,687 B2 | 5/2017 | Jansen et al. |
| 9,765,478 B2 | 9/2017 | Brandt et al. |
| 9,845,514 B2 | 12/2017 | Eyal et al. |

(56) References Cited

U.S. PATENT DOCUMENTS

| | | |
|---|---|---|
| 9,963,673 B2 | 5/2018 | Eyal et al. |
| 9,976,194 B2 | 5/2018 | Eyal et al. |
| 10,041,138 B1 | 8/2018 | Eyal et al. |
| 10,240,217 B2 | 3/2019 | Jansen et al. |
| 10,752,878 B2 | 8/2020 | Eyal et al. |
| 10,760,138 B2 | 9/2020 | Eyal et al. |
| 2001/0003797 A1 | 6/2001 | Guevara et al. |
| 2002/0061950 A1 | 5/2002 | Yamamoto et al. |
| 2002/0069981 A1 | 6/2002 | Speaks et al. |
| 2002/0096274 A1 | 7/2002 | Lindstrom et al. |
| 2002/0153317 A1 | 10/2002 | Heikkila et al. |
| 2002/0159990 A1 | 10/2002 | Ingram et al. |
| 2002/0164731 A1 | 11/2002 | Eroma et al. |
| 2003/0094416 A1 | 5/2003 | Heikkila et al. |
| 2003/0121516 A1 | 7/2003 | Hyoky et al. |
| 2003/0192660 A1 | 10/2003 | Speaks et al. |
| 2003/0199049 A1 | 10/2003 | Nguyen et al. |
| 2003/0222021 A1 | 12/2003 | Ennelin et al. |
| 2004/0074217 A1 | 4/2004 | Reaux |
| 2004/0108085 A1 | 6/2004 | Kettenbach et al. |
| 2004/0121446 A1 | 6/2004 | England et al. |
| 2004/0127371 A1 | 7/2004 | Arrowsmith et al. |
| 2004/0199049 A1 | 10/2004 | Parasher et al. |
| 2004/0231661 A1 | 11/2004 | Griffin et al. |
| 2004/0237499 A1 | 12/2004 | Yogev et al. |
| 2005/0034823 A1 | 2/2005 | Brelid et al. |
| 2005/0069998 A1 | 3/2005 | Ballesteros Perdices et al. |
| 2005/0136520 A1 | 6/2005 | Kinley et al. |
| 2005/0148056 A1 | 7/2005 | Levine et al. |
| 2005/0244934 A1 | 11/2005 | Foody et al. |
| 2006/0024801 A1 | 2/2006 | Holtzapple et al. |
| 2006/0041059 A1 | 2/2006 | Fukasawa et al. |
| 2006/0051812 A1 | 3/2006 | Helin et al. |
| 2006/0207734 A1 | 9/2006 | Day et al. |
| 2006/0246563 A1 | 11/2006 | Eroma et al. |
| 2006/0281913 A1 | 12/2006 | Ferreira et al. |
| 2007/0020375 A1 | 1/2007 | Jansen et al. |
| 2007/0031953 A1 | 2/2007 | Dunson et al. |
| 2007/0053987 A1 | 3/2007 | Bayer et al. |
| 2007/0112187 A1 | 5/2007 | Heikkila et al. |
| 2007/0184555 A1 | 8/2007 | Banavali et al. |
| 2007/0197363 A1 | 8/2007 | Parrotta et al. |
| 2007/0219521 A1 | 9/2007 | Hird et al. |
| 2007/0254348 A1 | 11/2007 | Retsina et al. |
| 2008/0029233 A1 | 2/2008 | Wingerson et al. |
| 2008/0032344 A1 | 2/2008 | Fallavollita |
| 2008/0041366 A1 | 2/2008 | Wahnon et al. |
| 2008/0057555 A1 | 3/2008 | Nguyen |
| 2008/0102502 A1 | 5/2008 | Foody et al. |
| 2008/0168982 A1 | 7/2008 | Vente et al. |
| 2008/0182305 A1 | 7/2008 | Foody et al. |
| 2008/0193992 A1 | 8/2008 | Levine |
| 2008/0202504 A1 | 8/2008 | Hilst |
| 2008/0210393 A1 | 9/2008 | Gutierrez-Suarez et al. |
| 2008/0216391 A1 | 9/2008 | Cortright et al. |
| 2008/0227161 A1 | 9/2008 | Levie et al. |
| 2008/0274509 A1 | 11/2008 | Filho et al. |
| 2008/0274528 A1 | 11/2008 | Dixon et al. |
| 2008/0292766 A1 | 11/2008 | Hoffman et al. |
| 2008/0299606 A1 | 12/2008 | Pompejus et al. |
| 2008/0300434 A1 | 12/2008 | Cortright et al. |
| 2008/0300435 A1 | 12/2008 | Cortright et al. |
| 2008/0305210 A1 | 12/2008 | Petersen |
| 2009/0053783 A1 | 2/2009 | Gokarn et al. |
| 2009/0056707 A1 | 3/2009 | Foody et al. |
| 2009/0056889 A1 | 3/2009 | Ren et al. |
| 2009/0061486 A1 | 3/2009 | Edwards et al. |
| 2009/0061495 A1 | 3/2009 | Beatty et al. |
| 2009/0062232 A1 | 3/2009 | Fujikawa et al. |
| 2009/0124829 A1 | 5/2009 | Gong |
| 2009/0142848 A1 | 6/2009 | Wyman et al. |
| 2009/0155873 A1 | 6/2009 | Kashiyama et al. |
| 2009/0173339 A1 | 7/2009 | Heikkilae et al. |
| 2009/0176286 A1 | 7/2009 | O'Connor et al. |
| 2009/0176979 A1 | 7/2009 | Hara et al. |
| 2009/0215718 A1 | 8/2009 | Van Laere et al. |
| 2009/0218055 A1 | 9/2009 | Uusitalo et al. |
| 2009/0226979 A1 | 9/2009 | Retsina et al. |
| 2009/0226993 A1 | 9/2009 | Kumar et al. |
| 2009/0229599 A1 | 9/2009 | Zhang et al. |
| 2009/0232892 A1 | 9/2009 | Yamasaki et al. |
| 2009/0286295 A1 | 11/2009 | Medoff et al. |
| 2009/0305942 A1 | 12/2009 | Day et al. |
| 2010/0009408 A1 | 1/2010 | England et al. |
| 2010/0024807 A1 | 2/2010 | Burke et al. |
| 2010/0028557 A1 | 2/2010 | Nagano |
| 2010/0043782 A1 | 2/2010 | Kilambi et al. |
| 2010/0043784 A1 | 2/2010 | Jensen |
| 2010/0048884 A1 | 2/2010 | Kilambi |
| 2010/0048924 A1 | 2/2010 | Kilambi |
| 2010/0055753 A1 | 3/2010 | Geros |
| 2010/0069626 A1 | 3/2010 | Kilambi |
| 2010/0083565 A1 | 4/2010 | Gruter et al. |
| 2010/0086981 A1 | 4/2010 | Latouf et al. |
| 2010/0093995 A1 | 4/2010 | Baniel et al. |
| 2010/0116267 A1 | 5/2010 | Mraz et al. |
| 2010/0124772 A1 | 5/2010 | Sabesan |
| 2010/0136634 A1 | 6/2010 | Kratochvil et al. |
| 2010/0136642 A1 | 6/2010 | Belanger et al. |
| 2010/0146844 A1 | 6/2010 | Dumenil |
| 2010/0151527 A1 | 6/2010 | Endo et al. |
| 2010/0151535 A1 | 6/2010 | Franklin et al. |
| 2010/0159566 A1 | 6/2010 | Leschine et al. |
| 2010/0160624 A1 | 6/2010 | Cunningham |
| 2010/0163019 A1 | 7/2010 | Chornet et al. |
| 2010/0167351 A1 | 7/2010 | Eyal et al. |
| 2010/0170504 A1 | 7/2010 | Zhang |
| 2010/0184151 A1 | 7/2010 | Tolan et al. |
| 2010/0184176 A1 | 7/2010 | Ishida et al. |
| 2010/0189706 A1 | 7/2010 | Chang et al. |
| 2010/0196979 A1 | 8/2010 | Birkmire et al. |
| 2010/0203605 A1 | 8/2010 | Kim et al. |
| 2010/0213130 A1 | 8/2010 | Airaksinen et al. |
| 2010/0233761 A1 | 9/2010 | Czartoski et al. |
| 2010/0249390 A1 | 9/2010 | Azuma et al. |
| 2010/0255554 A1 | 10/2010 | Benson et al. |
| 2010/0268000 A1 | 10/2010 | Parekh et al. |
| 2010/0269990 A1 | 10/2010 | Dottori et al. |
| 2010/0279354 A1 | 11/2010 | De Crecy |
| 2010/0279361 A1 | 11/2010 | South et al. |
| 2010/0279372 A1 | 11/2010 | Cho et al. |
| 2010/0287826 A1 | 11/2010 | Hoffman et al. |
| 2010/0297704 A1 | 11/2010 | Li |
| 2010/0305241 A1 | 12/2010 | Balakshin et al. |
| 2010/0305242 A1 | 12/2010 | Balakshin et al. |
| 2010/0305243 A1 | 12/2010 | Balakshin et al. |
| 2010/0305244 A1 | 12/2010 | Balakshin et al. |
| 2010/0313882 A1 | 12/2010 | Dottori et al. |
| 2011/0003348 A1 | 1/2011 | Genta et al. |
| 2011/0003352 A1 | 1/2011 | Retsina et al. |
| 2011/0020873 A1 | 1/2011 | Ren et al. |
| 2011/0020910 A1 | 1/2011 | Glass et al. |
| 2011/0028710 A1 | 2/2011 | Baniel et al. |
| 2011/0033640 A1 | 2/2011 | Yamada et al. |
| 2011/0033896 A1 | 2/2011 | Boy et al. |
| 2011/0053238 A1 | 3/2011 | Ohgren Gredegard et al. |
| 2011/0059316 A1 | 3/2011 | Kilambi et al. |
| 2011/0060132 A1 | 3/2011 | Lewis |
| 2011/0061645 A1 | 3/2011 | Fosdick et al. |
| 2011/0065159 A1 | 3/2011 | Raines et al. |
| 2011/0070131 A1 | 3/2011 | Schmidt et al. |
| 2011/0097776 A1 | 4/2011 | Johnson |
| 2011/0100359 A1 | 5/2011 | North |
| 2011/0105737 A1 | 5/2011 | Benjelloun Mlayah et al. |
| 2011/0124057 A1 | 5/2011 | Genta et al. |
| 2011/0126448 A1 | 6/2011 | Dumenil |
| 2011/0129880 A1 | 6/2011 | Conners et al. |
| 2011/0129886 A1 | 6/2011 | Howard et al. |
| 2011/0143411 A1 | 6/2011 | Yuan et al. |
| 2011/0143412 A1 | 6/2011 | Kim et al. |
| 2011/0146138 A1 | 6/2011 | Berry et al. |
| 2011/0155559 A1 | 6/2011 | Medoff |
| 2011/0178290 A1 | 7/2011 | Baniel et al. |
| 2011/0183394 A1 | 7/2011 | Bell et al. |

(56) References Cited

U.S. PATENT DOCUMENTS

| | | |
|---|---|---|
| 2011/0192560 A1 | 8/2011 | Heikkila et al. |
| 2011/0201059 A1 | 8/2011 | Hall et al. |
| 2011/0256615 A1 | 10/2011 | Brady et al. |
| 2011/0262984 A1 | 10/2011 | Nguyen |
| 2011/0263811 A1 | 10/2011 | Sawai et al. |
| 2011/0268652 A1 | 11/2011 | Machhammer et al. |
| 2011/0271875 A1 | 11/2011 | Ahmed et al. |
| 2011/0275860 A1 | 11/2011 | Beldring et al. |
| 2011/0281298 A1 | 11/2011 | Rawls et al. |
| 2011/0300617 A1 | 12/2011 | Genta et al. |
| 2011/0314726 A1 | 12/2011 | Jameel et al. |
| 2011/0318796 A1 | 12/2011 | Walther |
| 2012/0006320 A1 | 1/2012 | Nguyen |
| 2012/0023810 A1 | 2/2012 | Fjare et al. |
| 2012/0036768 A1 | 2/2012 | Phillips et al. |
| 2012/0040408 A1 | 2/2012 | Decker et al. |
| 2012/0055466 A1 | 3/2012 | Cotti Comettini et al. |
| 2012/0058526 A1 | 3/2012 | Jansen et al. |
| 2012/0104313 A1 | 5/2012 | Garbero et al. |
| 2012/0116063 A1 | 5/2012 | Jansen et al. |
| 2012/0122170 A1 | 5/2012 | Ropars et al. |
| 2012/0134912 A1 | 5/2012 | Baniel et al. |
| 2012/0135489 A1 | 5/2012 | Weydahl |
| 2012/0156517 A1 | 6/2012 | Vuori et al. |
| 2012/0167874 A1 | 7/2012 | Jansen et al. |
| 2012/0184026 A1 | 7/2012 | Eyal |
| 2012/0227733 A1 | 9/2012 | Eyal et al. |
| 2012/0240921 A1 | 9/2012 | Fukuoka et al. |
| 2012/0264873 A1 | 10/2012 | Eyal et al. |
| 2012/0279497 A1 | 11/2012 | Jansen et al. |
| 2012/0282655 A1 | 11/2012 | Gibbs |
| 2012/0289692 A1 | 11/2012 | Gray et al. |
| 2012/0308991 A1 | 12/2012 | Eiteman et al. |
| 2012/0323053 A1 | 12/2012 | Qiao et al. |
| 2013/0012610 A1 | 1/2013 | Belanger et al. |
| 2013/0019859 A1 | 1/2013 | Qiao et al. |
| 2013/0028832 A1 | 1/2013 | Eyal et al. |
| 2013/0028833 A1 | 1/2013 | Eyal et al. |
| 2013/0047979 A1 | 2/2013 | Eyal et al. |
| 2013/0115653 A1 | 5/2013 | Peterson et al. |
| 2013/0167836 A1 | 7/2013 | Floyd et al. |
| 2013/0167837 A1 | 7/2013 | Floyd et al. |
| 2013/0183729 A1 | 7/2013 | Huang et al. |
| 2013/0210101 A1 | 8/2013 | Parekh et al. |
| 2013/0216693 A1 | 8/2013 | Harrison et al. |
| 2013/0217070 A1 | 8/2013 | Zhao et al. |
| 2013/0252312 A1 | 9/2013 | Yoshikuni et al. |
| 2013/0276778 A1 | 10/2013 | Jansen et al. |
| 2013/0295628 A1 | 11/2013 | Retsina et al. |
| 2014/0011248 A1 | 1/2014 | Medoff et al. |
| 2014/0123973 A1 | 5/2014 | North |
| 2014/0154759 A1 | 6/2014 | Retsina et al. |
| 2014/0171379 A1 | 6/2014 | Jansen et al. |
| 2014/0175331 A1 | 6/2014 | Jansen et al. |
| 2014/0200365 A1 | 7/2014 | De Haan et al. |
| 2014/0202452 A1 | 7/2014 | Jansen et al. |
| 2014/0220651 A1 | 8/2014 | Raines et al. |
| 2014/0227161 A1 | 8/2014 | Manesh et al. |
| 2014/0242867 A1 | 8/2014 | Jansen et al. |
| 2014/0309416 A1 | 10/2014 | Teixeira et al. |
| 2014/0316162 A1 | 10/2014 | Gao et al. |
| 2014/0356915 A1 | 12/2014 | Retsina et al. |
| 2015/0020797 A1 | 1/2015 | Eyal et al. |
| 2015/0028255 A1 | 1/2015 | Eyal et al. |
| 2015/0048274 A1 | 2/2015 | Eyal et al. |
| 2015/0136345 A1 | 5/2015 | Tunc et al. |
| 2015/0144126 A1 | 5/2015 | Jansen et al. |
| 2015/0176090 A1 | 6/2015 | Dumesic et al. |
| 2015/0184261 A1 | 7/2015 | Floyd et al. |
| 2015/0197824 A1 | 7/2015 | Floyd et al. |
| 2015/0201660 A1 | 7/2015 | Kannar et al. |
| 2015/0299738 A1 | 10/2015 | Wang et al. |
| 2016/0108481 A1 | 4/2016 | Eyal et al. |
| 2016/0108482 A1 | 4/2016 | Eyal et al. |
| 2016/0222477 A1 | 8/2016 | Jansen et al. |
| 2016/0376546 A1 | 12/2016 | Eyal et al. |
| 2017/0037486 A1 | 2/2017 | Eyal et al. |
| 2017/0130282 A1 | 5/2017 | Eyal et al. |
| 2018/0142314 A1 | 5/2018 | Eyal et al. |

FOREIGN PATENT DOCUMENTS

| | | |
|---|---|---|
| CN | 1353310 A | 6/2002 |
| CN | 1505682 A | 6/2004 |
| CN | 101001952 A | 7/2007 |
| CN | 101120102 A | 2/2008 |
| CN | 101279722 A | 10/2008 |
| CN | 101313073 A | 11/2008 |
| CN | 101550431 A | 10/2009 |
| CN | 101613970 A | 12/2009 |
| CN | 101628853 A | 1/2010 |
| CN | 101787398 A | 7/2010 |
| CN | 101824054 A | 9/2010 |
| CN | 102239184 A | 11/2011 |
| CN | 102433358 B | 10/2013 |
| CN | 103555864 A | 2/2014 |
| CN | 103717622 A | 4/2014 |
| DE | 1955392 A1 | 6/1971 |
| EP | 0018621 A1 | 11/1980 |
| EP | 0317036 A1 | 5/1989 |
| EP | 0700957 A1 | 3/1996 |
| EP | 0814676 A1 | 1/1998 |
| EP | 0690931 B1 | 10/2001 |
| EP | 0697904 B1 | 6/2002 |
| EP | 1304412 A2 | 4/2003 |
| EP | 1458805 B1 | 8/2011 |
| EP | 1733282 B1 | 1/2012 |
| EP | 2325246 B1 | 11/2013 |
| GB | 1562682 A | 3/1980 |
| GB | 2488918 B | 3/2014 |
| JP | 55141451 A | 4/1976 |
| JP | 2835894 B2 | 12/1998 |
| JP | H11500912 A | 1/1999 |
| JP | 2001226409 A | 8/2001 |
| JP | 2002177000 A | 6/2002 |
| JP | 2005023041 A | 1/2005 |
| JP | 2006101829 A | 4/2006 |
| JP | 2006223152 A | 8/2006 |
| JP | 2008035853 A | 2/2008 |
| JP | 2010501013 A | 1/2010 |
| JP | 2011103874 A | 6/2011 |
| JP | 2011223975 A | 11/2011 |
| KR | 20140108301 A | 9/2014 |
| RU | 2313572 C2 | 12/2007 |
| WO | WO-8201723 A1 | 5/1982 |
| WO | WO-9305186 A1 | 3/1993 |
| WO | WO-9417213 A1 | 8/1994 |
| WO | WO-9426380 A1 | 11/1994 |
| WO | WO-0061276 A1 | 10/2000 |
| WO | WO-0125143 A1 | 4/2001 |
| WO | WO-0132715 A1 | 5/2001 |
| WO | WO-0202826 A1 | 1/2002 |
| WO | WO-02053783 A1 | 7/2002 |
| WO | WO-02070753 A2 | 9/2002 |
| WO | WO-03010339 A1 | 2/2003 |
| WO | WO-03056038 A1 | 7/2003 |
| WO | WO-2004003236 A1 | 1/2004 |
| WO | WO-2004013409 A1 | 2/2004 |
| WO | WO-2004050983 A1 | 6/2004 |
| WO | WO-2006006164 A2 | 1/2006 |
| WO | WO-2006034581 A1 | 4/2006 |
| WO | WO-2006038863 A1 | 4/2006 |
| WO | WO-2006056838 A1 | 6/2006 |
| WO | WO-2006086861 A2 | 8/2006 |
| WO | WO-2006086861 A3 | 10/2006 |
| WO | WO-2007019505 A2 | 2/2007 |
| WO | WO-2007019505 A3 | 6/2007 |
| WO | WO-2007102638 A1 | 9/2007 |
| WO | WO-2007112314 A2 | 10/2007 |
| WO | WO-2007112314 A3 | 11/2007 |
| WO | WO-2007130984 A2 | 11/2007 |
| WO | WO-2008019468 A1 | 2/2008 |
| WO | WO-2008027699 A2 | 3/2008 |
| WO | WO-2008069830 A2 | 6/2008 |

(56) References Cited

FOREIGN PATENT DOCUMENTS

| | | |
|---|---|---|
| WO | WO-2008027699 A3 | 7/2008 |
| WO | WO-2008109877 A1 | 9/2008 |
| WO | WO-2008111045 A1 | 9/2008 |
| WO | WO-2008123419 A1 | 10/2008 |
| WO | WO-2008131229 A1 | 10/2008 |
| WO | WO-2008069830 A3 | 11/2008 |
| WO | WO-2008137639 A1 | 11/2008 |
| WO | WO-2008144903 A1 | 12/2008 |
| WO | WO-2009003292 A1 | 1/2009 |
| WO | WO-2009015663 A2 | 2/2009 |
| WO | WO-2009020459 A2 | 2/2009 |
| WO | WO-2009030713 A1 | 3/2009 |
| WO | WO-2009031164 A1 | 3/2009 |
| WO | WO-2009036674 A1 | 3/2009 |
| WO | WO-2009020459 A3 | 4/2009 |
| WO | WO-2006006164 A3 | 5/2009 |
| WO | WO-2009060126 A1 | 5/2009 |
| WO | WO-2009110374 A1 | 9/2009 |
| WO | WO-2009125400 A2 | 10/2009 |
| WO | WO-2009135480 A1 | 11/2009 |
| WO | WO-2009137839 A1 | 11/2009 |
| WO | WO-2009142837 A2 | 11/2009 |
| WO | WO-2009015663 A3 | 12/2009 |
| WO | WO-2009154447 A1 | 12/2009 |
| WO | WO-2009155982 A1 | 12/2009 |
| WO | WO-2009125400 A3 | 1/2010 |
| WO | WO-2010006840 A2 | 1/2010 |
| WO | WO-2010009343 A2 | 1/2010 |
| WO | WO-2010009515 A1 | 1/2010 |
| WO | WO-2010015404 A1 | 2/2010 |
| WO | WO-2010018105 A1 | 2/2010 |
| WO | WO-2010020977 A2 | 2/2010 |
| WO | WO-2009142837 A3 | 3/2010 |
| WO | WO-2010026244 A1 | 3/2010 |
| WO | WO-2010026572 A1 | 3/2010 |
| WO | WO-2010009343 A3 | 4/2010 |
| WO | WO-2010034055 A1 | 4/2010 |
| WO | WO-2010037178 A1 | 4/2010 |
| WO | WO-2010038021 A2 | 4/2010 |
| WO | WO-2010043424 A1 | 4/2010 |
| WO | WO-2010045576 A2 | 4/2010 |
| WO | WO-2010046532 A1 | 4/2010 |
| WO | WO-2010046619 A1 | 4/2010 |
| WO | WO-2010006840 A3 | 5/2010 |
| WO | WO-2010064229 A2 | 6/2010 |
| WO | WO-2010064229 A3 | 7/2010 |
| WO | WO-2010081231 A1 | 7/2010 |
| WO | WO-2010038021 A3 | 8/2010 |
| WO | WO-2010106230 A1 | 9/2010 |
| WO | WO-2010020977 A3 | 10/2010 |
| WO | WO-2010113129 A2 | 10/2010 |
| WO | WO-2010113130 A2 | 10/2010 |
| WO | WO-2010122554 A1 | 10/2010 |
| WO | WO-2010128272 A1 | 11/2010 |
| WO | WO-2010113129 A3 | 12/2010 |
| WO | WO-2010135804 A1 | 12/2010 |
| WO | WO-2010135805 A1 | 12/2010 |
| WO | WO-2010135806 A1 | 12/2010 |
| WO | WO-2010135807 A1 | 12/2010 |
| WO | WO-2010135832 A1 | 12/2010 |
| WO | WO-2010135833 A1 | 12/2010 |
| WO | WO-2010146331 A2 | 12/2010 |
| WO | WO-2010113130 A3 | 1/2011 |
| WO | WO-2011002660 A1 | 1/2011 |
| WO | WO-2011007043 A1 | 1/2011 |
| WO | WO-2011007369 A1 | 1/2011 |
| WO | WO-2011017587 A1 | 2/2011 |
| WO | WO-2011028554 A1 | 3/2011 |
| WO | WO-2011039751 A2 | 4/2011 |
| WO | WO-2011066487 A1 | 6/2011 |
| WO | WO-2011070602 A1 | 6/2011 |
| WO | WO-2011080131 A2 | 7/2011 |
| WO | WO-2011088302 A1 | 7/2011 |
| WO | WO-2011089589 A1 | 7/2011 |
| WO | WO-2011091044 A1 | 7/2011 |
| WO | WO-2011095977 A1 | 8/2011 |
| WO | WO-2011097719 A1 | 8/2011 |
| WO | WO-2011080131 A3 | 9/2011 |
| WO | WO-2011111189 A1 | 9/2011 |
| WO | WO-2011111190 A1 | 9/2011 |
| WO | WO-2010146331 A3 | 10/2011 |
| WO | WO-2011039751 A3 | 10/2011 |
| WO | WO-2011121181 A1 | 10/2011 |
| WO | WO-2011140222 A1 | 11/2011 |
| WO | WO-2011151823 A1 | 12/2011 |
| WO | WO-2011154604 A1 | 12/2011 |
| WO | WO-2011154967 A1 | 12/2011 |
| WO | WO-2011161685 A2 | 12/2011 |
| WO | WO-2011163084 A1 | 12/2011 |
| WO | WO-2012001688 A2 | 1/2012 |
| WO | WO-2012015575 A1 | 2/2012 |
| WO | WO-2012018740 A1 | 2/2012 |
| WO | WO-2012031270 A1 | 3/2012 |
| WO | WO-2012050650 A1 | 4/2012 |
| WO | WO-2012061085 A2 | 5/2012 |
| WO | WO-2012079021 A2 | 6/2012 |
| WO | WO-2012081740 A1 | 6/2012 |
| WO | WO-2012085684 A2 | 6/2012 |
| WO | WO-2012106727 A1 | 8/2012 |
| WO | WO-2012137201 A1 | 10/2012 |
| WO | WO-2013038399 A1 | 3/2013 |
| WO | WO-2013040702 A1 | 3/2013 |
| WO | WO-2013055785 A1 | 4/2013 |
| WO | WO-2013070969 A2 | 5/2013 |
| WO | WO-2013083876 A2 | 6/2013 |
| WO | WO-2013166469 A2 | 11/2013 |
| WO | WO-2013192572 A1 | 12/2013 |
| WO | WO-2014013506 A1 | 1/2014 |
| WO | WO-2014044753 A1 | 3/2014 |
| WO | WO-2014081605 A1 | 5/2014 |
| WO | WO-2014126471 A1 | 8/2014 |
| WO | WO-2014138553 A1 | 9/2014 |
| WO | WO-2014169079 A2 | 10/2014 |
| WO | WO-2014178911 A1 | 11/2014 |
| WO | WO-2015139141 A1 | 9/2015 |
| WO | WO-2016112134 A1 | 7/2016 |
| WO | WO-2016191503 A1 | 12/2016 |

OTHER PUBLICATIONS

Allosio-Ouarnier, et al. Application of High Performance Anion Exchange Chromatography to the Study of Carbohydrate Changes in Barley During Malting. Journal—Institute of Brewing 106(1):45-52. Jan. 2000.

Neureiter et al. Dilute-acid hydrolysis of sugarcane bagasse at varying conditions. Applied Biochemistry and Biotechnology. Mar. 2002, vol. 98, Issue 1-9, pp. 49-58.

Sevcik, et al. Rapid analysis of carbohydrates in aqueous extracts and hydrolysates of biomass using a carbonate-modified anion-exchange column. J Chromatogr A. Mar. 4, 2011;1218(9):1236-43. doi: 10.1016/j.chroma.2011.01.002. Epub Jan 11, 2011.

Barton. "Table 18 Hoy's Cohesion Parameters for liquids (and solids and subcooled liquids) at 25° C." in CRC Handboook of solubility parameters and other cohesion parameters, Second Edition, Jan. 1, 1991. CRC Press, Boca Raton, FL. pp. 123-138.

Co-pending U.S. Appl. No. 16/243,888, filed Jan. 9, 2019.

Rangamannar, et al. Improved wet bulk storage of bagasse for newsprint pulp production—part 1. Pulping conference TAPPI proceedings. 1993; 391-398.

Co-pending U.S. Appl. No. 16/560,653, filed Sep. 4, 2019.

Hirajama et al. Semibatch Hydrothermal Hydrolysis of Cellulose in a Filter Paper by Dilute Organic Acids. Ind Eng Chem Res 54:6052-6059 (May 22, 2015).

Raveendran et al. Influence of mineral matter on biomass pyrolysis characteristics. Fuel 74(12):1812-1822 (1995).

Zhuang et al. Analysis of cellulose hydrolysis products in extremely low acids. Nongye Gongcheng Xuebao 23(2):177-182 (2007). Abstract only. 1 page.

Aden, et al. Lignocellulosic Biomass to Ethanol Process Design and Economics Utilizing Co-Current Dilute Acid Prehydrolysis and Enzymatic Hydrolysis for Corn Stover. National Renewable Energy Laboratory, NREL is a U.S. Department of Energy Laboratory Operated by Midwest Research Institute. Jun. 2002.

(56) References Cited

OTHER PUBLICATIONS

ADM corn 42/43 syrup. Typical data information. Accessed Oct. 5, 2012.
Agblevor, et al. Analysis of biomass sugars using a novel HPLC method. Appl Biochem Biotechnol. Mar. 2007;136(3):309-26.
Ahmed, et al. Preparation and studies on immobilized α-glucosidase from bakers yeast Saccharomyces cerevisiae. J. Serb. Chem. Soc. 2007; 72(12):1255-1263.
Amidon, et al. Biorefinery: Conversion of Woody Biomass to Chemicals, Energy and Materials. Journal of Biobased Materials and Bioenergy. 2008; 2:100-120.
Antonoplis, et al. High pressure HCl conversion of cellulose to glucose. Lawrence Berkeley National Laboratory, University of California, Paper LBL,14221. Aug. 1981.
ASTM Standards. Standard Test Method for Ash in Biomass. Designation: E1755-01 (Reapproved 2007).
Atalla, et al. Analysis of Lignin and Cellulose in Biological Energy Sources by Raman Microscopy. 2011.
Badger. Ethanol from cellulose: a general review. Trends in new crops and new uses. 2002; 17-21.
Barton. CRC handbook of solubility parameters and other cohesion parameters. CRC Press. Boca Raton. 1991; 122-138.
Beatriz, et al. Purification of xylitol obtained by fermentation of corncob hydrolysates. Journal of Agriculture and Food Chemistry. 2006; 54(12):4430-4435. (Abstract only).
Beck, et al. Production of ethanol by bioconversion of wood sugars derived from two-stage dilute acid hydrolysis of hardwood. Biomass. 1984; 6:101-110.
Bergius. Conversion of wood to carbohydrates and problems in the industrial use of concentrated hydrochloric acid. Industrial and Engineering chemistry. 1937; 29(3):247-253.
Bergius. The utilisation of wood for the production of foodstuffs, alcohol and glucose. Chemical society institution. Nov. 15, 1933.
Bergius. Winslow Notes on Bergius Process. 1937.
Bergius. Wood Sugar Plants at Mannheim-Rheinau & Regensburg. 1945.
Berndes, et al. The contribution of biomass in the future global energy supply: a review of 17 studies. Biomass and Bioenergy. 2003; 25:1-28.
Binder, et al. Mechanistic insights on the conversion of sugars into 5-hydroxymethylfurfural. Energy Environ. Sci., 2010; 3:765-771.
Biology Online. "Oligosaccharide". Downloaded Mar. 27, 2017. 1 page.
Bond. Xylitol. Informational data sheet. Mar. 3, 2009; 786-790.
Bozell. The Use of Renewable Feedstocks for the Production of Chemicals and Materials—A Brief Overview of Concepts. National Renewable Energy Laboratory, 1617 Cole Boulevard, Golden, CO 80401. 2010.
Bridgwater, et al. Identification and market analysis of most promising added-value products to be co-produced with the fuels. Project No. 212831, Project end date: May 31, 2010; 1-132.
Brown. Determination of Dry Substance in Beet Sugar Juices, A Precision Method. Industrial and Engineering chemistry. Jul. 1924; 16(7):746-748.
Brown, et al. Initial Market Assessment for Small-Scale Biomass-Based CHP, Prepared under Task No. WF6N.1050. National Renewable Energy Laboratory. Jan. 2008.
Brummer, et al. Understanding Carbohydrate Analysis. Chapter 2. Copyright 2005 by Taylor & Francis Group, LLC.
Bunker. The Wartime Production of Food Yeast in Germany. 2010.
Buranov, et al. Extraction and characterization of hemicelluloses from flax shives by different methods. Carbohydrate Polymers, vol. 79, No. 1, 2010 (pp. 17-25).
Burchell, et al. The development of novel activated carbon composites. 17th Annual Conference on Fossil Energy Materials, Wyndham Baltimore Inner Harbor Hotel, Baltimore, Maryland, Apr. 22-24, 2003.
Byrne. Expression, purification and crystallisation of membrane proteins. 2011.
Campa et al. Capillary Electrophoresis of Neutral Carbohydrates. Methods in molecular biology.2008; 384:247-305.
Campa et al. Capillary electrophoresis of sugar acids. Methods in molecular biology. 2008; 384: 307-355.
Campbell, et al. The Saccharification of Wood by the Bergius process at Suddeutschen Holzversucherung Werke A.G. Regensburg. Report on visit to Suddeutschen Holzversucherung Werke A.G. Regensburg.CIOS trip No. 764, this target was visited on Aug. 9, 1945.
Campos. Calculations of VLE in electrolytes systems using chemical theory: aqueous acis chloridric system. 2nd Mercosur Congress on Chemical Engineering; 4th Mercosur Congress on Process Systems Engineering. 2008.
Canilha, et al. Bioconversion of hemicellulose from sugarcane biomass into sustainable products. Sustainable Degradation of Lignocellulosic Biomass—Techniques, Applications and Commercialization. book edited by Anuj K. Chandel and Silvio Silvério da Silva, ISBN 978-953-51-1119-1, Published: May 15, 2013; Ch 2:15-45.
Cardona, et al. Production of bioethanol from sugarcane bagasse: Status and perspectives. Bioresource Technology. 2010; 101:4754-4766.
Carole, et al. Opportunities in the Industrial Biobased Products Industry. Applied Biochemistry and Biotechnology. 2004; 113-116:871-88.
Carr. The Biobased Revolution: How Biotechnology and Policy Are Changing the Way Materials Are Made. ASC Fall Convention & Expo. Oct. 11, 2005.
Carvalheiro, et al. Hemicellulose biorefineries: a review on biomass pretreatments. Journal of Scientific and Industrial Research. 2008; 67:849-864.
Carvalho, et al. Comparison of different procedures for the detoxification of eucalyptus hemicellulosic hydrolysate for use in fermentative processes. J Chem Technol Biotechnol 2006; 81:152-157.
Cassales, et al. Optimization of soybean hull acid hydrolysis and its characterization as a potential substrate for bioprocessing. Biomass and Bioenergy. 2011; 35:4675-4683.
Cayle, et al. The application of Mathews' Formula in Enzymatic Starch Conversions. Mar. 1966; 43:237-244.
Chandel, et al. Detoxification of Lignocellulosic Hydrolysates for Improved Bioethanol Production. Biofuel Production—Recent Developments and Prospects. Sep. 1, 2011, pp. 225-246.
Chaow-U-Thai et al. Removal of ash from sugarcane leaves and tops. International Journal of Biosciences.2012; 2(5): 12-17.
Cheng et al. A novel method to prepare L-arabinose from xylose mother liquor by yeast-mediated biopurification. Microbial cell factories.2011; 10 (43): 1-11.
Claricone Clarifiers and FiltraCone treatment plants. CB&I. Accessed Nov. 30, 2011.
Cole. XCV. The determination of reducing sugars by titration of ferricyanide. Biochem. 1933 xxvii, pp. 723-726. 0.
Coma, et al. alpha-Glucosidase and N-Acetyl-p-o-glucosaminidase Isoenzymes in Serum. Clin. Chem. 1992; 38(2):223-226.
Corn sweetener guide. Corn sweetener refining with ion exchange resins. Purolite. Jan. 18, 2007. 60 pages.
CUI. Structural Analysis of Polysaccharides. Chapter 3. Copyright 2005 by Taylor & Francis Group, LLC.
Curtis, et al. Equilibria in furfural-water systems under increased pressure and the influence of added salts upon the mutual solubilities of furfural and water. Aus. J. Sci. Res; 1948; 1(2): 213-235.
De Souza, et al. Composition and structure of sugarcane cell wall polysaccharides: implications for seconds generation bioethanol production. Bioenerg. Res. 2012; 16 pages. doi:10.1007/s12155-012-9268-1.
Delgado, et al. Sugar processing and by-products of the sugar industry. FAO Agricultural Services Bulletin 144. Rome, 2001.
Demirbas. Furfural Production from Fruit Shells by Acid-Catalyzed Hydrolysis, Energy Sources, Part A: Recovery, Utilization, and Environmental Effects. 2006; 28(2):157-165.
Demirbas. Products from lignocellulosic materials via degradation processes. Energy Sources, Part A. 2008; 30:27-37.
Dever, et al. Partial Chemical Characterization of Corn Root Cell Walls. Plant Physiol 43, 50-56, 1968.

(56) References Cited

OTHER PUBLICATIONS dictionary.com. "Oligosaccharide". Downloaded Mar. 27, 2017. 2 pages.
Dipardo. Outlook for Biomass Ethanol Production and Demand. Energy Information Administration. 2008; 1-14.
Dowex Ion exchange resins for HFCS deashing and polishing. Technical Manual. The Dow Chemical Company. Published Jun. 2002. 28 pages.
Dyadic. AlternaFuel® 200P, Product #326, (for considerations in biomass saccharification applications). 2010.
Dyadic. Enzyme Development for Fuel Ethanol Production from Pre-treated Biomass, Technical Report May 2010, Saccharification I.D: Sacc May 17, 2010.
Encyclopaedia Britannica. Biochemistry. "Oligosaccharide". Downloaded Mar. 27, 2017. 1 page.
Eyal, et al. Extraction of Strong Mineral Acids by Organic Acid-Base Couples. Ind. Eng. Chem. Process Des. Dev. 1982, 21, 334-337.
Eyal, et al. pH dependence of carboxylicand mineral acid extraction by amine-based extractants: effects of pKa, Amine Basicity, and diluent properties. Ind. Eng. Chem. Res. 1995; 34:1789-1798.
Eyal, et al. Recovery and concentration of strong mineral acids from dilute solutions through LLX.I: review of parameters for adjusting extractant propert and analysis of process options. Solvent Extraction and ion exchange. 1991; 9(2):195-210.
Eyal, et al. Sulfuric acid recovery through solvent aided decomposition of ammonium sulfate. Solvent Extraction and ion exchange. 1986; 44:803-821.
Fahim, et al. Liquid-Liquid Equilibria of the Ternary System Water + Acetic Acid + 1-Hexanol. J. Chem. Eng. Data. 1997; 42:183-186.
Ferrari, et al., Ethanol production from eucalyptus wood hemicellulose hydrolysate by pichia stipitis, 1992, biotech and bioengineering, 40:753-759.
Finney, Nathaniel. Essentials of Glycobiology. Carbohydrate Structure and Nomenclature. Lecture. Apr. 1, 2004. pp. 1-26.
Foran, et al. Beyond 2025: Transitions to the biomass-alcohol economy using ethanol and methanol. Working Paper Series 99/07. Dec. 1999.
Foxit. Chemicals partition in wood. Mar. 2011.
Franco, et al. How much trash to remove from sugarcane field to produce bioenergy? Brazilian Bioethanol Science and Technology Laboratory. 2008. 3 pages.
Galego, et al. Mechanism of the thermal resinification of pure furfural . Revista CENIC, Ciencias Fisicas. 1975; 6(1):163-180. Abstract only.
Gamez et al. Study of the hydrolysis of sugar cane bagasse using phosphoric acid. Journal of Food Engineering.2006; 74: 78-88.
Georgieva, et al. Enzymatic hydrolysis and ethanol fermentation of high dry matter wet-exploded wheat straw at low enzyme loading. Applied biochemistry and biotechnology. 2008;148:35-44.
Georgopoulos, et al. Thermoplastic polymers reinforced with fibrous agricultural residues. 2009.
Goldstein. Potential for Converting Wood into Plastics, Chemicals from wood may regain importance as the cost of petroleum continues to rise. Science, Sep. 12, 1975; 189(4206):847-852.
Gray, et al. Sugar Monomer and Oligomer Solubility, Data and Predictions for Application to Biomass Hydrolysis. Applied Biochemistry and Biotechnology. 2003; 105-108:179-193.
Górecka, et al. The application of ICP-MS and ICP-OES in determination of micronutrients in wood ashes used as soil conditioners. Talanta. Dec. 15, 2006;70(5):950-6.
Grethlein, et al. The Cost of Ethanol Production from Lignocellulosic Biomass—A Comparison of Selected Alternative Processes. USDA. Specific Cooperative Agreement No. 58-1935-2-050. Apr. 30, 1993.
Griffith, et al. Low cost carbon fiber for transportation application. USDE. 2003.
Gullon, et al. Production of oligosaccharides and sugars from rye straw: a kinetic approach. Bioresource technology, 2010, 101(17), pp. 6676-6684.
Hagglund. The Decomposition of Wood by Acids wood Saccharification. Chemistry of Wood. New York: Academic Press, 1951. 631. Chapter IV. 390-413.
Hagglund. Wood Saccharification. A Modified Rheinau Process. 2011.
Hall. Polyhydric alcohol from wood. US Department of Agriculture, Forest Service, Forest Products Laboratory , Madison, Wisconsin. No. 1984. Jul. 1954.
Hallac, et al. Biomass Characterization of Buddleja davidii: A Potential Feedstock for Biofuel Production. J. Agric. Food Chem. 2009; 57(4):1275-1281.
Hamelinck, et al. Ethanol from lignocellulosic biomass: techno-economic performance in short-, middle- and long-term. Biomass and Bioenergy; 2005; 28; 384-410.
Hamelinck, et al. Production of advanced biofuels. International Sugar Journal. 2006; 108(1287):168-175.
Han, et al. Optimizing lignocellulosic feedstock for improved biofuel productivity and processing. Biofuels, Bioprod. Bioref. 2007; 1:135-146.
Hanchar, et al. Separation of glucose and pentose sugars by selective enzyme hydrolysis of AFEX-treated corn fiber. Appl Biochem Biotechnol. Apr. 2007;137-140(1-12):313-25. doi: 10.1007/s12010-007-9061-3.
Harada, et al. Formation of Isoamylase by Pseudomonas. Applied Microbiology. Oct. 1968; 16(10):1439-1444.
Harris. Derived products and chemical utilization of wood waste. Forest Products Laboratory; Forest Service US Department of Agriculture; Rept. No. R1666-10. Jun. 1949.
Harris, et al. Hydrolysis of wood cellulose with hydrochloric acid and sulfur dioxide and the decomposition of its hydrolytic products. Journal of Physical and Colloid Chemistry. (1949), 53:344-51. Abstract only.
Harris, et al. The Madison Wood-Sugar Process. US Dept. of Agriculture. Jun. 1946; 1-21.
Hasegawa, et al. New Pretreatment Methods Combining a Hot Water Treatment and Water/Acetone Extraction for Thermo-Chemical Conversion of Biomass. Energy & Fuels. 2004; 18:755-760.
Hayes, et al. The Biofine Process: Production of Levulinic Acid, Furfural and Formic Acid from Lignocellulosic Feedstocks. Biorefinery (8b). 2011.
Heinonen, et al. Chromatographic recovery of monosaccharides for the production of bioethanol from wood. Ind. Eng. Chem. Res. 2010; 49:2907-2915.
Held. Catalytic conversion of renewable plant sugars to fungible liquid hydrocarbon fuels using the bioforming process. TAPPI IBBC session 3. Virent Energy systems. Oct. 15, 2009.
Herty. Advanced Materials Development Center. HCI Clean Tech Composite Sample—Extracted Wood Sample. 2010.
Hinz, et al. Hemicellulase production in Chrysosporium lucknowense C1. Journal of Cereal Science. 2009; 50(3):318-323. doi:10.1016/j.jcs.2009.07.005.
Hirst, et al. CCCLXXXII.—The action of highly concentrated hydrochloric acid on cellulose and on some derivatives of glucose and of xylose. 1923; 3226-3235.
Hodge. Chemistry of Browning Reactions in Model Systems. Agricultural and Food Chemistry. Oct. 14, 1953; 1(15):928-943.
Holmen. Direct conversion of methane to fuels and chemicals. Catalysts Today. 2009; 142:2-8.
Hou-Rui, et al. Novel Isolates for Biological Detoxification of Lignocellulosic Hydrolysate. Appl Biochem Biotechnol 2009; 152:199-212.
Hu, et al. Chemical profiles of switchgrass. Bioresource Technology. 2010; 101:3253-3257.
Hu, et al. The direct conversion of xylan to lactic acid by lactobacillus brevis transformed with a xylanase gene. Green Chem., vol. 13(7), pp. 1729-1734 (2011).
Huang, et al. A review of separation technologies in current and future biorefineries. Separation and Purification Technology. 2008; 62:1-21.
Huber. Breaking the Chemical and Engineering Barriers to Lignocellulosic Biofuels: Next Generation. Based on the: Jun. 25-26, 2007, Workshop, Washington D.C.

(56) References Cited

OTHER PUBLICATIONS

Huber, et al. Synthesis of Transportation Fuels from Biomass: Chemistry, Catalysts, and Engineering. Chemical Reviews. Published on Web Jun. 27, 2006 p. EST: 54.3, 10.1021/cr068360d.

Ibrahim, et al. Comparison of alkaline pulping with steam explosion for glucose production from rice straw. Carbohydrate Polymers. 2011; 83:720-726.

International search report and written opinion dated Feb. 15, 2013 for PCT/US2012/059542.

Ioannidou et al. Direct determination of toxic trace metals in honey and sugars using inductively coupled plasma atomic emission spectrometry. Talanta, 65(1): 92-97 (2005).

Iranmahboob, et al. Optimizing acid-hydrolysis: a critical step for production of ethanol from mixed wood chips. Biomass and Bioenergy. 2002; 22:401-404.

Ismagilov, et al. Direct conversion of methane on Mo/ZSM-5 catalysts to produce benzene and hydrogen: achievements and perspectives. Energy and Environmental Science. 2008; 1:526-541.

IsoClear 42% high fructose 80% solids corn syrup. Technical product information. Cargill. Updated Aug. 14, 2012.

Itzkowitz. Biodiesel from sugars. 2011.

Izydorczyk, et al. Polysaccharide Gums: Structures, Functional Properties, and Applications. Chapter 6. Copyright 2005 by Taylor & Francis Group, LLC.

Izydorczyk. Understanding the Chemistry of Food Carbohydrates. Chapter 1. Copyright 2005 by Taylor & Francis Group, LLC.

Jacobsen et al. Xylose Monomer and Oligomer Yields for Uncatalyzed Hydrolysis of Sugarcane Bagasse Hemicellulose at Varying Solids Concentration. Industrial & Engineering Chemistry Research; 2002; 41; 1454-1461.

Johnson. Effects of Dilute Acid Hydrolyzate Components on Glucose Degradation. National Bioenergy Center, NREL, 1617 Cole Blvd., Golden, Colorado 80401, USA. 2011.

Kadam, et al. Generating Process and Economic Data Needed for Preliminary Design of PureVision Biorefineries. DOE Project No. DE-FG36-05G085004, Final Nonproprietary Technical Report. Dec. 28, 2007.

Kaewwongsa, et al. Intestinal digestibility of the residual components of cassava pulp solid state fermentation by *Saccharomyces cerevisiae*. Suranaree J. Sci. Technol. 2009; 16(4):291-296.

Kamm, et al. Chemical and biochemical generation of carbohydrates from lignocellulose-feedstock (Lupinus nootkatensis)—quantification of glucose. Chemosphere. 2006; 62:97-105.

Kamm, et al. Definition and technical status of Biorefineries. BioreFuture 2008, Tuesday Feb. 12, 2008, Brussels.

Kaparaju, et al. Bioethanol, biohydrogen and biogas production from wheat straw in a biorefinery concept. Bioresour Technol. May 2009;100(9):2562-8. doi: 10.1016/j.biortech.2008.11.011. Epub Jan. 8, 2009.

Khan, et al. Kinetic Study on Palm Oil Waste Decomposition. Biofuel's Engineering Process Technology. 2011. Chapter 22, pp. 523-536.

Kim, et al. Continuous Countercurrent Extraction of Hemicellulose from Pretreated Wood Residues. Applied Biochemistry and Biotechnology. 2001; 91-93:253-267.

Kim, et al. Enzyme hydrolysis and ethanol fermentaion of liquid hot water and AFEX pretreated distillers' grains at high-solid loadings. Bio. Tech. 2008; 99:5206-5215.

Kimberley, et al. A colorimetric method for the quantitation of galacturonic acid. Applied biochemistry and biotechnology. 1993; 43:51-54.

Kinders, et al. Saccharification of HCl-treated substrate provided by HCL-Cleantech, Technical Report, Mar. 2010. Dyadic International Inc. // Confidential and Proprietary Information.

Kireble, et al. The Electromotive Force Measurements of Hydrochloric Acid Solutions with and without Sucrose and their Relation to the Rate of Sucrose Hydrolysis. Chemical Laboratory of Trinity college. Jan. 1935; 57:19-22.

Kjellstrand, et al. Development of toxic degradation products during heat sterilization of glucose-containing fluids for peritoneal dialysis: influence of time and temperature. Perit Dial Int. 1995;15(1):26-32.

Kucuk, et al. Biomass Conversion Processes. Energy Convers. Mgmt. 1997; 38(2):151-165.

Kumar, et al. Effect of Enzyme Supplementation at Moderate Cellulase Loadings on Initial Glucose and Xylose Release From Corn Stover Solids Pretreated by Leading Technologies. Biotechnology and Bioengineering. Feb. 1, 2009; 102(2):457-567.

Kumar, et al. Methods for Pretreatment of Lignocellulosic Biomass for Efficient Hydrolysis and Biofuel Production. Ind. Eng. Chem. Res. 2009; 48:3713-3729.

Kunkes, et al. Catalytic conversion of biomass to monofunctional hydrocarbons and targeted liquid-fuel classes. Science. Oct. 17, 2008;322(5900):417-21. doi: 10.1126/science.1159210. Epub Sep. 18, 2008.

Lam, et al. Kinetic Modeling of Pseudolignin Formation in Steam Exploded Woody Biomass. 2011.

Lange, et al. Lignocellulose conversion: an introduction to chemistry, process and economics. Biofuels, Bioprod. Bioref. 2007; 1:39-48.

Lavarack, et al. The acid hydrolysis of sugarcane bagasse hemicellulose to produce xylose, arabinose, glucose and other products. Biomass and Bioenergy. 2002; 23:367-380.

Lee, et al. Dilute-Acid Hydrolysis of Lignocellulosic Biomass. Advances in Biochemical Engineering/ Biotechnology. 1999; 65:93-115.

Leonard, et al. Fermentation of wood sugars to ethyl alcohol. US Department of Agriculture, Forest Service, Forest Products Laboratory, Madison, Wisconsin. No. R1466. Dec. 1944.

Leshchuk, et al. Penetration of concentrated hydrochloric acid into the pores of wood particles and the formation of hydrolyzates within the particles. Sbornik Trudov. Gosudarstvennyi Nauchno-issledovatel'skii Institut Gidroliznoi i Sul'fitno-spirtovoi Promyshlennosti (1966), 15 156-67. CODEN: SGSSAC. Abstract only. 0.

Li, et al. Acidolysis of Wood in Ionic Liquids. Ind. Eng. Chem. Res. 2010; 49(7):3126-3136.

Li, et al. Interaction of Supercritical Fluids with Lignocellulosic Materials. Ind. Eng. Chem. Res. 1988; 27:1301-1312.

Liavoga, et al. Release of D-xylose from wheat straw by acid and xylanase hydrolysis and purification of xylitol. J Agric Food Chem. Sep. 19, 2007;55(19):7758-66. Epub Aug. 28, 2007.

Lin, et al. Ethanol fermentation from biomass resources: current state and prospects. Appl Microbiol Biotechnol. 2006; 69:627-642.

Liu. Understanding Starches and Their Role in Foods. Chapter 7. Copyright 2005 by Taylor & Francis Group, LLC.

Lora. GreenValue-Technologies and Products. GreenValueEnterprises LLC, Media, PA, USA. 2011.

Lora. Non-Wood Biorefinery Developments Outside North America. 2011.

Lu, et al. Hydrolysis of Japanese beech by batch and semi-flow water under subcritical temperatures and pressures. Biomass and Bioenergy, Feb. 2010, pp. 1089-1097.

Lynd, et al. Strategic Biorefinery Analysis: Analysis of Biorefineries, Jan. 24, 2002-Jul. 1, 2002. Subcontract Report, NREL/SR-510-35578, Jan. 10, 2005.

Mabee, et al. Updates on Softwood-to-Ethanol Process Development. Applied Biochemistry and Biotechnology, 2006;129-132:55-70.

Mai, et al. Biotechnology in the wood industry. Appl Microbiol Biotechnol; 2004; 63:477-494.

Marchal, et al. Conversion into acetone and butanol of lignocellulosic substrates pretreated by steam explosion. Biotechnology Letters. 1986; 8(5):365-370.

Marker, et al. Optical properties of glucose. 2009.

Martinez, et al. Detoxification of dilute acid hydrolysates of lignocellulose with lime. Biotechnology Progress, American Institute of Chemical Engineers, vol. 17, Jan. 1, 2001, pp. 287-293.

Mascal, et al. Direct, High Yield Conversion of Cellulose into Biofuel. Angew. Chem. Int. Ed. 2008; 7:7924-7926.

Mascal, et al. High-Yield Chemical Conversion of Biomass into Biofuels and Value added Products. Clean Technology 2010, www.ct-si.org, ISBN 978-1-4398-3419-0. 124-127.

(56) References Cited

OTHER PUBLICATIONS

Mascal et al. Towards the efficient, total glycan utilization of biomass. ChemSusChem; 2009; 2(5); 423-426.
Mateos-Espejel, et al. Implications of converting a Kraft pulp mill to a dissolving pulp operation with a hemicellulose extractionstage. 2012 PEERS Conference. 32-70.
McAloon, et al. Determining the Cost of Producing Ethanol from Corn Starch and Lignocellulosic Feedstocks. National Renewable Energy Laboratory, Contract No. DE-AC36-99-G010337, NREL/TP-580-28893. Prepared under Task No. BFP1.7110. Oct. 2000.
McKenzie, et al. Levulinic acid. Organic Syntheses, Coll. vol. 1, p. 335 (1941); vol. 9, p. 50 (1929). Apr. 29, 2010.
Medical Dictionary: thefreedictionary.com. "Oligosaccharide". Downloaded Mar. 27, 2017. 2 pages.
Michalka, Optimization of Sugar Consumption in the Fermentation of Temulose for Ethanol Production, 2007.
Mielenz. Ethanol production from biomass: technology and commercialization status. Current Opinion in Microbiology. 2001; 4:324-329.
Mikkola, et al. Hydrolytic decomposition of glycosides in aqueous acids. ARKIVOC 2009 (iii) 39-53.
Miljkovic. Carbohydrates, Synthesis, Mechanisms, and Stereoelectronic Effects. Springer Science+Business Media, LLC 2009.
Miller-Ihli et al. Direct determination of lead in sugars using graphite furnace atomic absorption spectrometry. Atomic Spectroscopy, 14(4): 85-89 (1993).
Minifie. Chocolate, Cocoa, and Confectionery. Science and Technology. An Aspen Publication. 3rd Ed. 1989.
Moelwyn-Hughes. The kinetics of the hydrolysis of certain glucosides, part 11: trehalose, umethylglucoside and tetramethyl-a-amethyglucoside. Nov. 23, 1928; 81-92.
Mythili, et al. Synthesis, mechanical, thermal and chemical properties of polyurethanes based on cardanol. Bull. Mater. Sci. Jun. 2004 ;27(3):235-241.
Nikam et al. Density and Viscosity Studies of Glucose and Fructose Solutions in Aqueous and in NH4CL. Journal of Molecular Liquids; 2000; 87; 97-105.
Novozymes. The key to the first commercially viable enzymes for cellulosic ethanol. 2010. www.bioenergy.novozymes.com.
NREL. Enzyme Sugar-Ethanol Platform Project. National Renewable Energy Laboratory, Operated for the U.S. Department of Energy by Midwest Research Institute • Battelle • Bechtel. 2010.
Nutrients review.com. "Oligosaccharides". Downloaded Mar. 27, 2017. 4 pages.
Nystrand. Feasibility of lignocellulose as feedstock for biological production of super absorbent polymers. Department of Physics, Chemistry and Biology Master's Thesis; Linkoping University Department of Physics, Chemistry and Biology 581 83 Linköping. Oct. 2010.
Olsson, et al. Fermentation of lignocellulosic hydrolysates for ethanol production. Enzyme and Microbial Technology. 1996; 18:312-331.
Onda et al. Selective Hydrolysis of Cellulose and Polysaccharides into Sugars by Catalytic Hydrothermal Method Using Sulfonated Activated-carbon. Journal of Japan Petroleum Institue.2012; 55(2): 73-86.
Ong. Conversion of lignocellulosic biomass to fuel ethanol—a brief review. The planter kuala lumpur. 2004; 80(941):517-524.
Oxford Dictionary. "Oligosaccharide". Downloaded Mar. 27, 2017. 1 page.
Palmqvist, et al. Fermentation of lignocellulosic hydrolysates. II: inhibitors and mechanisms of inhibition. Bioresource Technology. 2000; 74:25-33.
Pan, et al. Biorefining of Softwoods Using Ethanol Organosolv Pulping: Preliminary Evaluation of Process Streams for Manufacture of Fuel-Grade Ethanol and Co-Products. Biotechnology and bioengineering. May 20, 2005; 90(4).
Papadopoulous, et al. Behavior of sweetgum wood xylan and lignin during hydrolysis with concentrated hydrochloric acid at moderate temperatures. Dep. Wood Pap. Sci., North Carolina State Univ., Raleigh, NC, USA. Journal of Applied Polymer Science: Applied Polymer Symposium (1983), 37(Proc. Cellul. Conf., 9th, 1982, Part 2), 631-40. CODEN: JPSSDD ISSN: 0271-9460. Abstract only.
Paszner, et al. High-yield Organosolv process for conversion of cellulosic biomass to ethanol. Fac. For., Dep. Harvest. Wood Sci., Vancouver, BC, Can. Energy from Biomass and Wastes (1989), 12 1297-318. CODEN: EBWADU ISSN: 0277-7851. Abstract only.
Patel, et al. Medium and long-term Opportunities and Risks of the Biotechnological Production of Bulk Chemicals from Renewable Resources—The Potential of White Biotechnology The BREW project. Utrecht University. Sep 2006. www.chem.uu.nl/nws.
Pazur. Reversibility of enzymatic transglucosylation reactions. Received for publication, Jan. 17, 1955, pp. 531-538.
Perlack, et al. Biomass as feedstock for a bioenergy and bioproducts industry: the technical feasibility of a billion-ton annual supply. U.S. Department of Energy, under contract DE-AC05-00OR22725. Apr. 2005.
Pessoa Jr, et al. Acid hydrolysis of hemicellulose from sugarcane bagasse. Braz. J. Chem. Eng. vol. 14 No. 3 São Paulo Sep. 1997.
Philip, et al. Review Polyhydroxyalkanoates: biodegradable polymers with a range of applications. J Chem Technol Biotechnol. 2007; 82:233-247.
Phillips, et al. Thermochemical Ethanol via Indirect Gasification and Mixed Alcohol Synthesis of Lignocellulosic Biomass. National Renewable Energy Laboratory, Technical Report NREL/TP-510-41168. Apr. 2007.
Phillips. Technoeconomic Analysis of a Lignocellulosic Biomass Indirect Gasification Process to Make Ethanol. Ind. Eng. Chem. Res. 2007; 46:8887-8897.
Pierce. Instruction Acylation Derivatization Reagents. Pierce, Rockford, IL 61105, US. 2010.
Ping, et al. Evaluation of grape stalks as bioresource. Industrial crops and products. 2011; 33:200-204.
Pohl et al. Direct Determination of the Total Concentrations of Magnesium, Calcium, Manganese, and Iron in Addition to their Chemical and Physical Fractions in Dark Honeys. Anal. Lett., 44(13): 2265-2279 (2011).
Polymer Science. Making Polyurethane. Polymer Science Learning Center, Department of Polymer Science the University of Southern Mississippi. 2005.
Prater, et al. Determination of Sulfur Dioxide in Dehydrated Foods. Industrial and engineering chemistry. Mar. 1944; 16(3):153-157.
Priefert, et al. Biotechnological production of vanillin. Appl Microbiol Biotechnol. 2001; 56:296-314. Abstract only.
Qian, et al. Acidic Sugar Degradation Pathways an Ab Initio Molecular Dynamics Study. Applied Biochemistry and Biotechnology. 2005;121-124:989-997.
Rabinovich. Wood hydrolysis industry in the Soviet Union and Russia: a mini-review. Cellulose Chem. Technol.2010; 44(4-6):173-186.
Radiotis, et al. Optimizing Production of Xylose and Xylooligomers from Wood Chips. 3rd NWBC, Stockholm, Sweden Mar. 23, 2011.
Ragauskas, et al. From wood to fuels Integrating biofuels and pulp production. Industrial biotechnology. 2006; 2(1):55-65.
Ragauskas, et al. The Path Forward for Biofuels and Biomaterials. Science. Jan. 26, 2006; 311:484-489.
Raz. Weyland bioethanol report. 2010.
Reimann, et al. Element levels in birch and spruce wood ashes—green energy? Science of the Total environment. 2008; 393:191-197.
Ritcey et al. Development of Industrial Solvent Extraction Processes. (Report) Gordon M. Ritcey & Associates, Inc; Nepean, Ontario, Canada.2004.
Robbins, et al. Liquid-Liquid Extraction Operations and Equipment. Sec. 15. 2009.
Rockwood, et al. Energy Product Options for Eucalyptus Species Grown as Short Rotation Woody Crops. Int. J. Mol. Sci. 2008; 9:1361-1378; DOI: 10.3390/ijms9081361.
Rondinini, et al. Reference value standards and primary standards for pH measurements in Organic Solvents and Water + Organic Solvent Mixtures of Moderate to High Permittivities. Pure & Appl. Chem. 1987; 59(11):1549-1560.

(56) References Cited

OTHER PUBLICATIONS

Rovio, et al. Determination of monosaccharide composition in plant fiber materials by capillary zone electrophoresis. Journal of Chromatography A. 2008; 1185:139-144.
Rovio, et al. Determination of neutral carbohydrates by CZE with direct UV detection. Electrophoresis. 2007; 28:3129-3135.
Rozmarin, et al. Fermentative evaluation of prehydrolyzates from chemical cellulose manufacturing. II. Study on some factors affecting the inversion process. Rom. Revista Padurilor-Industria Lemnului-Celuloza si Hirtie: Celuloza si Hirtie (1977), 26(4), 158-62. CODEN: RPLHDX ISSN: 0258-2287. Abstract only.
Rumbold. Selection of production hosts for real-life feedstock utilization. TNO Kwaliteit van Leven, Oct. 20, 2007.
Saari et al. Adsorption Equilibria of Arabinose, Fructose, Galactose, Rhamnose, Sucrose, and Xylose on Ion-Exchange Resins. J. Chem. Eng.; 2010; 55; 3462-3467.
Saddler et. al. Pretreatment of Lodgepole Pine Killed by Mountain Pine Beetle Using the Ethanol Organosolv Process: Fractionation and Process Optimization. Ind. Eng. Chem. Res. 2007;46: 2609-2617.
Saeman. Kinetics of the hydrolysis of wood and of the decomposition of sugars in dilute acid at high tempratures. USDA. Sep. 1944.
Saha, et al. Dilute Acid Pretreatment, Enzymatic Saccharification, and Fermentation of Rice Hulls to Ethanol. Biotechnol. Prog. 2005; 21:816-822.
Saltberg et al. Removal of metal ions from wood chips during acidic leaching 1: Comparison between Scandinavian softwood, birch and eucalyptus. Nordic Pulp and Paper Research Journal. 2006; 21: 507-512.
Saltberg, et al. Removal of metal ions from wood chips during acidic leaching 2: Modeling leaching of calcium ions from softwood chips. Nordic Pulp and Paper Research J. 2006; 21(4):513-519.
Sanchez, et al. Structural analysis of acid catalysed furfuraldehyde resins by thermal degradation techniques. Eur. Polym. J. 1994; 30(1):43-50.
Sanchez, et al. Trends in biotechnological production of fuel ethanol from different feedstocks. Bioresource Technology. 2008; 99:5270-5295.
Sanders, et al. Shuttle hydrochloric acid process for the preparation of oligosaccharides containing products from wood. Comm. Eur. Communities, [Rep.] EUR (1987), (EUR 11084, Degrad. Lignocellul. Ruminants Ind. Processes), 97-101. CODEN: CECED9 ISSN: 0303-755X. Abstract only.
Sasaki, et al. Cellulose hydrolysis in subcritical and supercritical water. J. Of Supercritical Fluids. 1998; 13:261-268.
Sasaki, et al. Dissolution and Hydrolysis of Cellulose in Subcritical and Supercritical Water. Ind. Eng. Chem. Res. 2000, pp. 2883-2890.
Sassner, et al. Techno-economic evaluation of bioethanol production from three different lignocellulosic materials. Biomass and bioenergy. 2008; 32:422-430.
Satin Sweet® 65% High Maltose Corn Syrup. Cargill foods. www.cargillfoods.com Updated Aug. 12, 2014.
Sato, et al. Determination of monosaccharides derivatized with 2-aminobenzoic Acid by capillary electrophoresis. Ana. BioChem. 1997; 251: 119-121.
Schaefer. Bio-Based opportunities in chemicals & energy. Novozymes. London, UBS. Nov. 17, 2010.
Schenck. Glucose and Glucose-Containing Syrups. Ullmann's Encyclopedia of Industrial Chemistry, vol. 17, http://dx.doi.org/10.1002%2F14356007.a12_457.pub2, 2006 (pp. 45-66).
Schoenemann. The New Rheinau Wood Saccharification Process. Institute of Chemical Technology. Jul. 27, 1953; 1-49.
Schuchardt et al. Hydrolysis of sugar cane bagasse with hydrochloric acid, promoted by metallic cations. Journal of Chemical Technology & Biotechnology. 1986; 36:329-334.
Scurfield, et al. Amino-Acid Composition of Wood Proteins. J. Experimental Botany. 1970; 21(6):857-68.
Seppala, et al. The effect of additives on the speed of the crystallization front of xylitol with various degrees of supercooling. Experimental Thermal and Fluid Science 34 (2010) 523-527.
Sharkov. Production of Polyhydric Alcohols from Wood Polysaccharides. Angew. Chem. internat. Edit. 1963; 2(8):405-492.
Sheehan, et al. Energy and Environmental Aspects of Using Corn Stover for Fuel Ethanol. Journal of Industrial Ecology. 2004; 7(3-4):117-146.
Shen, et al. Product overview and market projection of emerging bio-based plastics, Utrecht University. PRO-BIP 2009.
Shimizu, et al. Integrated process for total utilization of wood components by steam-explosion pretreatment. Biomass and bioenergy. 1998; 14(3):195-203.
Sidiras, et al. Simulation of acid-catalysed organosolv fractionation of wheat straw. Bioresource Technology. 2004; 94:91-98.
Sigma. Enzymatic Assay of $\alpha$-Glucosidase. Sigma quality control test procedure. Sigma Product information, Revised: Aug. 9, 1996.
Sigma. Enzymes and Reagents for Alternative Energy. Sigma-Aldrich. Biofiles. 2010; 5(5).
Singh, et al. Visualization of Biomass Solubilization and Cellulose Regeneration During Ionic Liquid Pretreatment of Switchgrass. Biotechnology and Bioengineering. Sep. 1, 2009; 104(1):68-75.
Sluiter, et al. Determination of Ash in Biomass, Laboratory Analytical Procedure (LAP), Issue Date: Jul. 17, 2005. Technical Report, NREL/TP-510-42622, Jan. 1, 2008.
Sluiter, et al. Determination of Sugars, Byproducts, and Degradation Products in Liquid Fraction Process Samples. Laboratory Analytical Procedure (LAP), Contract No. DE-AC36-99-GO10337. Issue Date: Dec. 8, 2006.
Sluiter, et al. Determination of Sugars, Byproducts, and Degradation Products in Liquid Fraction Process Samples, Laboratory Analytical Procedure (LAP), Issue Date: Dec. 8, 2006. Technical Report, NREL/TP-510-42623, Jan. 1, 2008.
Sluiter, et al. Determination of Total Solids in Biomass and Total Dissolved Solids in Liquid Process Samples, Laboratory Analytical Procedure (LAP), Issue Date: Mar. 31, 2008. Technical Report, NREL/TP-510-42621, Revised Mar. 2008.
So, et al. Economic Analysis of Selected Lignocellulose-to-Ethanol Conversion Technologies. Applied Biochemistry and Biotechnology. 1999; 77-79:633-640.
Solange, et al. A study on the recovery of xylitol by batch adsorption and crystallization from fermeneted sugarcane bagasse hydrolysate. Journal of Chemical Technology and Biotechnology. 2006; 81(11):1840-1845. (Abstract only).
Soloman, et al. Grain and cellulosic ethanol: History, economics, and energy policy. Biomass and Bioenergy. 2007; 31:416-425.
Srinorakutara, et al. Approach of Cassava Waste Pretreatments for Fuel Ethanol Production in Thailand. 2010.
Srinorakutara, et al. Utilization of Waste from Cassava Starch Plant for Ethanol Production. The Joint International Conference on "Sustainable Energy and Environment (See)" Dec. 1-3, 2004, Hua Hin, Thailand. 344-349.
Standard test method for ash in biomass. ASTM International. Designation E1755. Reapproved Oct. 9, 2015. 3 pages.
Steele. Recent breakthroughs in enzymes for biomass hydrolysis. Genecor. National Ethanol Conference, Feb. 23-25, 2009, San Antonio, Texas.
Suess. Interaction of organic compounds with calcium carbonate-I. Association phenomena and geochemical implications. Geochimia et Cosmochimic Acata. 1970; 34:157-168.
Sun, et al. Characterization and esterification of hemicelluloses from rye straw. Journal of Agricultural and Food Chemistry. 2000, 48(4), pp. 1247-1252.
Sun, et al. Hydrolysis of lignocellulosic materials for ethanol production: a review. Bioresource Technology. 2002; 83:1-11.
Taherzadeh, et al. Pretreatment of Lignocellulosic Wastes to Improve Ethanol and Biogas Production: A Review. Int. J. Mol. Sci. 2008; 9:1621-1651; DOI: 10.3390/ijms9091621.
Taylor, et al. Novel biosynthetic routes for the production of xylitol. 36th Great Lakes Regional Meeting of the American Cancer Society. Peoria, Il, USA. Oct. 17-20, 2004. Meeting abstract.
Terol et al. High-Temperature Liquid Chromatography Inductively Coupled Plasma Atomic Emission Spectrometry hyphenation for the combined organic and inorganic analysis of foodstuffs. J. Chromatography, 1217(40): 6195-6202 (2010).

(56) References Cited

OTHER PUBLICATIONS

The use of DOWEX ion exchange resins in corn sweetener processing. The Dow Chemical Company. Published Jun. 2002. 12 pages.
Thomsen. How 'green' are algae farms for biofuel production? Biofuels. 2010; 1(4):515-517.
Timell, et al. The acid hydrolysis of glycosides II. Effect of substituents at C-5. Canadian Journal of Chemistry. 1965; 43:2296-2305.
Trickett. Utilization of Baggase for the production of C5 and C6 sugars. MS Thesis; University of Natal, Durban, South Africa. 1982.
Urban, et al. Characterization of polymer-based monolithic capillary columns by inverse size-exclusion chromatography and mercury-intrusion porosimetry. Journal of Chromatography A. 2008; 1182:161-16.
Van Bramer. An Introduction to Mass Spectrometry. Widener University, Department of Chemistry, One University Place, Chester, PA 19013. 1998.
Van Dyke. Enzymatic Hydrolysis of Cellulose—A Kinetic Study. For the degree of Doctor of Science at the Massachusetts Institute of Technology, Sep. 1972.
Vassilev, et al. An overview of the chemical composition of biomass. Fuel, vol. 89, Issue 5, May 2010, pp. 913-933. Available online Nov. 10, 2009.
Veres et al. Studies on matrix effects in the determination of the metal content of sugar complexes by atomic absorption spectrometry. Magyar Kemiai Folyoirat, 93(5): 199-204 (1987).
Von Sivers, et al. A techno-economical comparison of three processes for the production of ethanol from pine. Bioresource Technology. 1995; 51:43-52.
Vulfson, et al. Glycosidases in organic solvents: I. Alkyl-fl-glucoside synthesis in a water-organic two-phase system. Enzyme Microb. Technol. Dec. 1990; 12:950-954.
Vyglazov. Kinetic characteristics of xylitol crystallization from aqueous-ethanolic solutions. Russian Journal of Applied Chemistry. 2004; 77:26-29.
Wang, et al. Measurement and correlation of solubility of xylitol in binary water+ethanol solvent mixtures between 278.00 K and 323.00K. Korean Journal of Chemical Engineering. Apr. 2013; 30(4):931-936.
Wang, et al. Molecular Characteristics of Kraft-AQ Pulping Lignin Fractionated by Sequential Organic Solvent Extraction. Int. J. Mol. Sci. 2010; 11:2988-3001.
Wang, et al. Understanding the Conformation of Polysaccharides. Chapter 5. Copyright 2005 by Taylor & Francis Group, LLC.
Wang, et al. Understanding the Physical Properties of Food Polysaccharides. Chapter 4. Copyright 2005 by Taylor & Francis Group, LLC.
Weingarten, et al. Kinetics of furfural production by dehydration of xylose in a biphasic reactor with microwave heating. Green Chem. 2010; 12:1423-1429.
Williams. Ethanol production potential and costs from lignocellulosic resources in California. 15th European Biomass Conference & Exhibition, May 7-11, 2007, Berlin, Germany.
Wilson, et al. Detection of tannins in modern and fossil barks and in plant residues by high-resolution solid-state $^{13}C$ nuclear magnetic resonance. Org. Geochem. 1988; 12(6):539-546.
Winandy, et al. Wood-plastic composites using thermomechanical pulp made from oxalic acid-pretreated red pine chips. 7th Global WPC and Natural Fibre Composites Congress and Exhibition, Jun. 18-19, 2008 in Kassel / Germany.
Winter, et al. NO and N2O formation during the combustion of wood, straw, malt waste and peat. Bioresource Technology. vol. 70, Issue 1, Oct. 1999, pp. 39-49.
Woodbridge et al. Nitrocellulose from wood pulp. J. Ind.Eng. Chem. 1920; 12(4):380-384.
Wood-Ethanol Report. Environment Canada. 1999.
Wu et al. Determination of trace calcium in glucose by Zeeman flame atomic absorption spectrometry. Guangdong Weiliang Yuansu Kexue, 14(3): 58-60 (2007).
Wyman. Biomass ethanol: Technical Progress, Opportunities, and Commercial Challenges. Annu. Rev. Energy Environ. 1999; 24:189-226.
Wyman, et al. Comparative sugar recovery data from laboratory scale application of leading pretreatment technologies to corn stover. Bioresource Technology. 2005; 96: 2026-2032.
Wyman. Potential Synergies and Challenges in Refining Cellulosic Biomass to Fuels, Chemicals, and Power. Biotechnol. Prog. 2003; 19:254-262.
Wyman. Twenty Years of Trials, Tribulations, and Research Progress in Bioethanol Technology. Applied Biochemistry and Biotechnology. 2001; 91-93:5-21.
Wyman. What is (and is not) vital to advancing cellulosic ethanol. TRENDS in Biotechnology. 2007; 25(4):153-157.
Xylitol A Global Market Overview. May 2014.
Yusmawati et al. Optical Properties and Sugar Content Determination of Commercial Carbonated Drinks using Surface Plasmon Resonance. American Journal of Applied Sciences. 2007;4: 1-4.
Zahedifar. Novel uses of lignin and hemicellulosic sugars from acidhyrolysed lignocellulosic materials. for the degree of Doctor of Philosophy, in the University of Aberdeen, Sep. 1996.
Zhang, et al. Cellodextrin preparation by mixed-acid hydrolysis and chromatographic separation. Analytical Biochemistry, 322(2), 2003 (pp. 225-232).
Zhang, et al. Ethanol production from paper sludge by simultaneous saccharification and co-fermentation using recombinant xylose-fermenting microorganisms. Biotechnology and bioengineering. 2010; 107(2):235-244.
Zhang. Reviving the carbohydrate economy via multi-product lignocellulose biorefineries. J Ind Microbiol Biotechnol. 2008; 35:367-375.
Zhao, et al. Fermentable hexose production from corn stalks and wheat straw with combined supercritical and subcritical hydrothermal technology. Bioscience Technology, vol. 100, Jul. 18, 2009, pp. 5884-5889.
Zhao, et al., Organosolv pretreatment of lignocellulosic biomass for enzymatic hydrolysis, Appl Microbiol Biotechnol (2009) 82:815-827.
Zhao, et al. Small-scale mashing procedure for predicting ethanol yield of sorghum grain. Journal of Cereal Science. 2009; 49:230-238.
Zhao, et al. Supercritical hydrolysis of cellulose for oligosaccharide production in combined technology. Chem. Eng. J. 2009; 150:411-417.
Zinoviev, et al. Background Paper on biofuels Production Technologies. International Center for Science and High Technology and UNIDO. Nov. 2007; 1-106.
Zorina, et al. Study of acid heterogeneous hydrolysis of pulp. USSR. Editor(s): Kiprianov, A. I. Khim. Pererab. Drev. (1982), 35-8. Publisher: Leningr. Lesotekh. Akad., Leningrad, USSR CODEN: 49HIA6. Abstract only.
International Search Report and Written Opinion dated May 17, 2016 for International PCT Patent Application No. PCT/US2016/012384.
Grzenia, et al. Detoxification of biomass hydrolysates by reactive membrane extraction. Journal of Membrane Science. vol. 348, Issues 1-2, Feb. 15, 2010, pp. 6-12.
Co-pending U.S. Appl. No. 16/922,199, filed Jul. 7, 2020.
Co-pending U.S. Appl. No. 16/935,619, filed Jul. 22, 2020.
Co-pending U.S. Appl. No. 16/937,200, filed Jul. 23, 2020.
Co-pending U.S. Appl. No. 16/849,831, filed Apr. 15, 2020.

\* cited by examiner ated Applications

METHOD FOR PRODUCING XYLITOL BY FERMENTATION

CROSS REFERENCE TO RELATED APPLICATIONS

This application is a National Stage Entry of PCT/US2016/012384, filed on Jan. 6, 2016, which claims the benefit of U.S. Provisional Application No. 62/100,791, filed on Jan. 7, 2015, and U.S. Provisional Application No. 62/249,801, filed on Nov. 2, 2015, each incorporated herein by reference in its entirety.

BACKGROUND OF THE INVENTION

Lignocellulosic biomass is an abundant renewable material that has long been recognized as a potential feedstock for producing chemicals, fuels, and materials, including polyol sugar substitutes such as xylitol. Lignocellulosic biomass comprises primarily cellulose, hemicellulose and lignin. Efficient and cost-effective processes to extract, separate and refine sugars from biomass are still a challenge.

Xylitol is a five-carbon sugar alcohol that has favorable properties as a sugar substitute, including low caloric content, good gastrointestinal tolerance, and near insulin-independent metabolism in humans. Traditionally, xylitol is produced by chemical hydrogenation of a monosaccharide mixture containing xylose in the presence of a metal catalyst, such as Raney nickel, necessitating specialized and expensive equipment for the high pressure and temperature requirements of the reaction. The hydrogenation is non-specific and produces polyols of other monosaccharides present in the reaction mixture that are difficult and costly to separate from the desired xylitol product. Trace metal is undesirable and must also be removed from the product. Overall, this expensive and inefficient process produces xylitol in only 40-60% yield. Some basic research has been performed toward the development of bioprocesses for the production of xylitol, but reasonable yields can only be obtained using pure D-xylose as a feedstock.

SUMMARY OF THE INVENTION

As such, there is a pressing need for a method of selecting sugar streams suitable for production of xylitol. The present disclosure addresses this need by providing methods, systems, and compositions to produce xylitol from lignocellulosic biomass. Lignocellulosic biomass can be processed and refined to produce hemicellulose sugar streams, and streams suitable for conversion to xylitol selected. This allows for efficient and cost-effective production of xylitol from renewable sources at an industrial scale.

In one aspect, the disclosure provides a method of producing xylitol from a lignocellulose-containing biomass. In one embodiment, the method comprises: (i) fermenting a refined hemicellulose sugar stream to produce a fermentation broth comprising xylitol; and (ii) recovering xylitol from the fermentation broth, wherein the refined hemicellulose sugar stream has been produced by a process comprising: (a) extracting hemicellulose sugars from the biomass, thereby obtaining a hemicellulose sugar stream and a lignocellulose remainder stream; (b) contacting the hemicellulose sugar stream with an amine extractant to form a mixture; and (c) separating from the mixture an organic stream comprising the amine extractant and at least one impurity and the refined hemicellulose sugar stream. Optionally, the biomass is selected from hardwood, wood-pulp, bagasse, sugarcane leaves, birch, *eucalyptus*, corn cobs, corn stover, coconut hulls, switchgrass, and wheat straw, such as bagasse and sugarcane leaves.

In some examples, the method further comprises reducing ash and soil content of the biomass prior to extracting hemicellulose sugars from the biomass. Optionally, the reducing comprises one or more stages of slurrying, washing, and dewatering the biomass. In some examples, the extracting hemicellulose sugars comprises hot water extraction. Optionally, the hot water extraction further comprises an acid, such as an inorganic acid. In some examples, the acid is present in an amount up to 2% weight/weight. Optionally, the extracting occurs at a temperature of 100 to 200° C.

In some examples, the amine extractant comprises an amine and a diluent. Optionally, the amine comprises at least 20 carbon atoms, such as trilaurylamime. Optionally, the diluent comprises an alcohol, such as hexanol or 2-ethyl-1-hexanol. In some examples, the diluent comprises a $C_{6-12}$ monoalcohol, kerosene, or a mixture thereof. In some examples, the at least one impurity is selected from ash, acid soluble lignin, furfural, fatty acids, inorganic acids, organic acids, methanol, proteins, amino acids, glycerol, sterols, rosin acid, and waxy materials.

In some examples, the fermentation broth further comprises a microorganism selected from naturally occurring bacteria, recombinant bacteria, naturally occurring yeast, recombinant yeast, and fungi, such as an *E. coli* strain. Optionally, the fermenting produces, in less than 80 hours, at least 60 grams of the xylitol per liter of the fermentation broth, such as at least 100 grams of the xylitol per liter of the fermentation broth. Optionally, the fermenting produces the xylitol at a rate of at least 1 g/L/h. In some examples, the fermentation broth comprises less than 1 gram of ethanol per liter.

In some examples, at least 70% of xylose in the biomass is converted to xylitol. Optionally, xylose content of the refined hemicellulose sugar stream is at least 80% the xylose content of the hemicellulose sugar stream. In some examples, the fermenting does not comprise xylose purified by crystallization. Optionally, the refined hemicellulose sugar stream comprises at least 50% xylose weight/weight relative to total dissolved sugars, such as between 50 and 90% xylose weight/weight relative to total dissolved sugars.

In one aspect, the disclosure provides a method for producing xylitol by fermentation of a refined hemicellulose sugar stream derived from a lignocellulosic hydrolysate. In one embodiment, the method comprises converting xylose in the refined hemicellulose sugar stream to xylitol through fermentation by a microorganism, wherein the refined hemicellulose sugar stream comprises: 50 to 90% xylose weight/weight relative to total dissolved sugars, less than 200 ppm calcium, and furfural in an amount up to 1000 ppm. In some examples, the microorganism is selected from naturally occurring bacteria, recombinant bacteria, naturally occurring yeast, recombinant yeast, and fungi, such as an *E. coli* strain. Optionally, the fermentation produces, in less than 80 hours, at least 60 grams of the xylitol per liter of fermentation broth, such as at least 100 grams of the xylitol per liter of fermentation broth. Optionally, the fermentation produces the xylitol at a rate of at least 1 g/L/h. In some examples, the fermentation broth comprises less than 1 gram of ethanol per liter.

In practicing any of the methods described herein, the refined hemicellulose sugar stream may comprise less than 5% oligomers weight/weight relative to total dissolved sugars. Optionally, the refined hemicellulose sugar stream comprises arabinose in an amount up to 12% weight/weight relative to total dissolved sugars, such as between 3 and 12% arabinose weight/weight relative to total dissolved sugars. Optionally, the refined hemicellulose sugar stream comprises at least 10% hexoses weight/weight relative to total dissolved sugars, such as between 10 and 45% hexoses weight/weight relative to total dissolved sugars. Optionally, the hexoses comprise glucose, galactose, mannose, and fructose. In some examples, glucose and fructose comprise at least 50% weight/weight of the hexoses. Optionally, the ratio of xylose to hexoses is between 1.5:1 and 5:1 weight/weight. Optionally, the refined hemicellulose sugar stream comprises disaccharides in an amount up to 8% weight/weight relative to total dissolved sugars. Optionally, the refined hemicellulose sugar stream comprises ash in an amount up to 0.25% weight/weight. Optionally, the refined hemicellulose sugar stream comprises phenolic compounds, wherein the phenolic compounds are present in amounts less than 200 ppm. Optionally, the refined hemicellulose sugar stream comprises furfural in an amount up to 200 ppm. Optionally, the refined hemicellulose sugar stream comprises less than 200 ppm calcium. Optionally, the refined hemicellulose sugar stream comprises nitrogen in an amount up to 1000 ppm.

In one aspect, the disclosure provides a system for producing xylitol from a lignocellulose-containing biomass. In one embodiment, the system comprises: (i) a hemicellulose extraction unit configured to extract and hydrolyze hemicellulose from the biomass to produce a hemicellulose sugar stream and a lignocellulose remainder stream; (ii) a refining unit in fluid communication with the extraction unit, wherein the refining unit is configured to receive the hemicellulose sugar stream and an amine extractant, and wherein the amine extractant removes impurities from the hemicellulose sugar stream to produce a refined hemicellulose sugar stream; (iii) a sensing unit configured to analyze one or more parameters of the refined hemicellulose sugar stream; (iv) a fermentation unit in fluid communication with the refining unit to receive the refined hemicellulose sugar stream, wherein the fermentation unit is configured to contain the refined stream and a microorganism, and wherein the microorganism facilitates production of the xylitol from a monosaccharide in the refined stream to produce a fermentation broth; and (v) a xylitol refining unit, wherein the xylitol refining unit is configured to remove the xylitol from the fermentation broth. In some examples, the system further comprises a wash unit configured to remove ash and soil from the biomass, wherein the hemicellulose extraction unit is in fluid communication with the wash unit.

In some examples, at least 90% of xylose in the refined hemicellulose sugar stream is converted to xylitol in the fermentation unit. Optionally, the xylitol is produced at a rate of at least 1 g/L/h in the fermentation unit. Optionally, the fermentation broth comprises less than 10 g/L ethanol, such as less than 4.5 g/L ethanol, optionally less than 1 g/L ethanol. In some examples, the biomass is selected from bagasse and sugarcane leaves, or a combination thereof. In some examples, the one or more parameters are selected from pH, light absorbance, conductivity, density, xylose concentration, and hexose concentration In one aspect, the disclosure provides a fermentation feedstock. In one embodiment, the fermentation feedstock comprises: (i) 50 to 90% xylose weight/weight relative to total dissolved sugars; (ii) 10 to 45% hexoses weight/weight relative to total dissolved sugars; (iii) arabinose in an amount up to 12% weight/weight relative to total dissolved sugars; (iv) disaccharides in an amount up to 8% weight/weight relative to total dissolved sugars; (v) furfural in an amount up to 1000 ppm; and (vi) less than 200 ppm calcium. Optionally, the feedstock further comprises (vii) less than 1000 ppm acetic acid; and (viii) less than 1000 ppm formic acid. In some examples, the feedstock further comprises a microorganism. In another embodiment, the fermentation feedstock comprises: (i) 50 to 90% xylose weight/weight relative to total dissolved sugars; (ii) less than 200 ppm calcium; (iii) furfural in an amount up to 1000 ppm; and (iv) a microorganism. Optionally, the feedstock further comprises 10 to 50% hexoses weight/weight relative to total dissolved sugars. Optionally, the feedstock further comprises arabinose in an amount up to 12% weight/weight relative to total dissolved sugars. Optionally, the feedstock further comprises disaccharides in an amount up to 8% weight/weight relative to total dissolved sugars. Optionally, the feedstock further comprises less than 1000 ppm acetic acid. Optionally, the feedstock further comprises less than 1000 ppm formic acid. In some examples, the feedstock further comprises a $C_{6-12}$ monoalcohol in an amount up to 100 ppm. In some examples, the feedstock further comprises nitrogen in an amount up to 1000 ppm.

In one aspect, the disclosure provides a fermentation broth. In one embodiment, the fermentation broth comprises: (i) at least 60 g/L xylitol; (ii) less than 10 g/L ethanol; (iii) xylose in an amount up to 50 g/L; (iv) hexoses in an amount up to 35 g/L; (v) furfural in an amount up to 1000 ppm; and (vi) less than 200 ppm calcium. In some examples, the broth further comprises: (vii) less than 1000 ppm acetic acid; and (viii) less than 1000 ppm formic acid. Optionally, the broth further comprises a $C_{6-12}$ monoalcohol in an amount up to 100 ppm. In some examples, the broth further comprises a microorganism.

In one aspect, the disclosure provides a xylitol composition. In one embodiment, the xylitol composition comprises: (i) at least 98% xylitol weight/weight relative to total dissolved solids; (ii) oligosaccharides in an amount up to 1% weight/weight relative to total dissolved solids; and (iii) hexoses in an amount up to 1%. In some examples, the xylitol composition further comprises ash in an amount up to 0.25% weight/weight relative to total dissolved solids. Optionally, the xylitol composition further comprises furfural in an amount up to 1000 ppm. Optionally, the xylitol composition further comprises an amine in an amount up to 100 ppm, and wherein the amine comprises at least 12 carbon atoms. Optionally, the xylitol composition further comprises a $C_{6-12}$ monoalcohol in an amount up to 100 ppm. In some examples, the hexoses are selected from glucose, galactose, mannose, and fructose. Optionally, the xylitol composition further comprises less than 100 ppm arabitol, such as less than 1 ppm arabitol. Optionally, the xylitol composition further comprises less than 100 ppm galactitol, such as less than 1 ppm galactitol. Optionally, the composition is derived from a hydrolyzate of a lignocellulose-containing biomass. Optionally, the composition is crystalline. Optionally, the composition is provided as an aqueous solution. In some examples, the aqueous solution comprises at least 50% weight/weight dissolved solids.

In one aspect, the disclosure provides a method of producing a refined hemicellulose sugar stream suitable for conversion to xylitol. In one embodiment, the method comprises: (i) extracting hemicellulose sugars from the biomass, thereby obtaining a hemicellulose sugar stream and a lignocellulose remainder stream; (ii) contacting the hemicellulose sugar stream with an amine extractant to form a mixture; (iii) separating from the mixture an organic stream comprising the amine extractant and at least one impurity and a refined hemicellulose sugar stream; and (iv) measuring concentrations of at least one of xylose, arabinose, hexoses, disaccharides, ash, acetic acid, formic acid, phenolic compounds, furfural, calcium, and nitrogen; wherein the refined hemicellulose sugar stream is suitable for conversion to xylitol if the refined stream comprises: (1) at least 50% xylose weight/weight relative to total dissolved sugars; (2) at least 10% hexoses weight/weight relative to total dissolved sugars; and (3) less than 200 ppm calcium; and wherein the refined stream suitable for conversion to xylitol further comprises at least one characteristic selected from: (4) arabinose in an amount up to 12% weight/weight relative to total dissolved sugars; (5) disaccharides in an amount up to 8% weight/weight relative to total dissolved sugars; (6) ash in an amount up to 0.25% weight/weight; (7) less than 1000 ppm acetic acid; (8) less than 1000 ppm formic acid; (9) phenolic compounds in an amount up to 200 ppm; (10) furfural in an amount up to 200 ppm; and (11) nitrogen in an amount up to 1000 ppm; and wherein a refined stream unsuitable for conversion to xylitol is further refined.

In some examples, the refined stream suitable for conversion to xylitol further comprises furfural in an amount up to 200 ppm. Optionally, the refined stream suitable for conversion to xylitol further comprises arabinose in an amount up to 12% weight/weight relative to total dissolved sugars. Optionally, the refined stream suitable for conversion to xylitol further comprises disaccharides in an amount up to 8% weight/weight relative to total dissolved sugars. Optionally, the refined stream suitable for conversion to xylitol further comprises ash in an amount up to 0.25% weight/weight. Optionally, the refined stream suitable for conversion to xylitol further comprises acetic acid in an amount up to 1000 ppm. Optionally, the refined stream suitable for conversion to xylitol further comprises formic acid in an amount up to 1000 ppm. Optionally, the refined stream suitable for conversion to xylitol further comprises phenolic compounds in an amount up to 200 ppm. Optionally, the refined stream suitable for conversion to xylitol further comprises nitrogen in an amount up to 1000 ppm.

INCORPORATION BY REFERENCE

All publications, patents, and patent applications mentioned in this specification are herein incorporated by reference to the same extent as if each individual publication, patent, or patent application was specifically and individually indicated to be incorporated by reference. PCT/IL2012/050118 filed Apr. 2, 2012, PCT/US2013/039585 filed May 3, 2013, PCT/US2013/068824 filed Nov. 6, 2013, PCT/US2014/053956 filed Sep. 3, 2014, U.S. App. No. 62/100,791 filed Jan. 7, 2015, and U.S. App. No. 62/249,801 filed Nov. 2, 2015 are incorporated by reference.

DETAILED DESCRIPTION OF THE INVENTION

Figure 1:
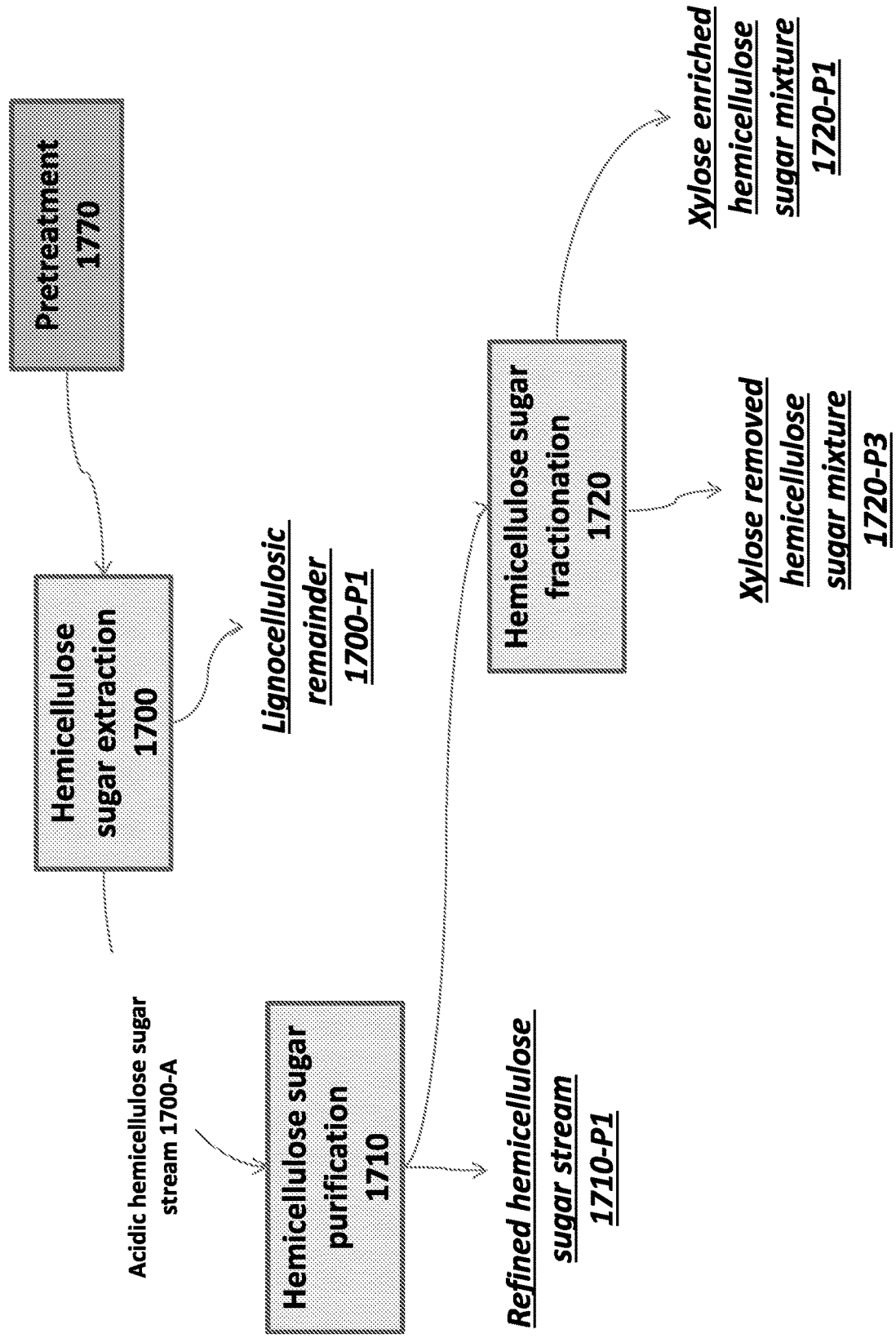
FIG. 1 illustrates a schematic diagram of exemplary conversion processes to convert biomass to downstream products such as a refined hemicellulose sugar stream.

The present disclosure relates to lignocellulosic biomass processing and refining to produce hemicellulose sugars, and the conversion thereof to high-value products (e.g., xylitol). Conversion of the hemicellulose sugars to high-value products may be completed by any suitable chemical, catalytic, enzymatic, metabolic, fermentation, or bioconversion process, or a combination thereof. Optionally, hemicellulose sugars are converted to high-value products by a fermentation process.

In one aspect, the disclosure provides a method of producing xylitol from a lignocellulose-containing biomass. In one example, the method comprises: (i) extracting hemicellulose sugars from the biomass, thereby obtaining a hemicellulose sugar stream and a lignocellulose remainder stream; (ii) contacting the hemicellulose sugar stream with an extractant (e.g., an amine extractant) to form a mixture; and (iii) separating from the mixture an organic stream comprising the extractant and at least one impurity and a refined hemicellulose sugar stream. Optionally, the method further comprises: (iv) fermenting the refined hemicellulose sugar stream to produce a fermentation broth comprising xylitol; and (v) recovering xylitol from the fermentation broth. Optionally, the method further comprises reducing ash and soil content of the biomass prior to extracting hemicellulose sugars from the biomass.

In one aspect, the disclosure provides a method of producing xylitol by fermentation of a refined hemicellulose sugar stream derived from a lignocellulosic hydrolysate. In one example, the method comprises converting xylose in the refined hemicellulose sugar stream to xylitol through fermentation by a microorganism. Optionally, the hemicellulose sugar stream comprises: 50 to 90% xylose weight/weight relative to total dissolved sugars, less than 200 ppm calcium, and furfural in an amount up to 1000 ppm.

In one aspect, the disclosure provides a method of producing a refined hemicellulose sugar stream suitable for conversion to xylitol. In one example, the method comprises: (i) extracting hemicellulose sugars from the biomass, thereby obtaining a hemicellulose sugar stream and a lignocellulose remainder stream; (ii) contacting the hemicellulose sugar stream with an extractant (e.g., an amine extractant) to form a mixture; (iii) separating from the mixture an organic stream comprising the extractant and at least one impurity and a refined hemicellulose sugar stream; and (iv) measuring concentrations of at least one of xylose, arabinose, hexoses, disaccharides, ash, acetic acid, formic acid, phenolic compounds, furfural, levulinic acid, calcium, and nitrogen; wherein a refined hemicellulose sugar stream is suitable for conversion to xylitol if the refined stream comprises: (1) at least 50% xylose weight/weight relative to total dissolved sugars; (2) at least 10% hexoses weight/weight relative to total dissolved sugars; and (3) less than 200 ppm calcium; and wherein the refined stream suitable for conversion to xylitol further comprises at least one characteristic selected from: (4) arabinose in an amount up to 12% weight/weight relative to total dissolved sugars; (5) disaccharides in an amount up to 8% weight/weight relative to total dissolved sugars; (6) ash in an amount up to 0.25% weight/weight; (7) acetic acid in amount up to 1000 ppm; (8) formic acid in amount up to 1000 ppm; (9) phenolic compounds in an amount up to 200 ppm; (10) furfural in an amount up to 200 ppm; and (11) nitrogen in an amount up to 1000 ppm; and wherein a refined stream unsuitable for conversion to xylitol is further refined.

A biomass embodied in a subject method or system disclosed herein is typically high in xylan content. The biomass may be derived from wood, softwood, hardwood such as alder, aspen, birch, beech, maple, poplar, *eucalyptus*, and willow, plants or plant constituents, grains such as wheat, barley, rice, rye and oat, particulates of grain such as straw, hulls, husks, fiber, shells, and stems, corn cobs, corn straw, corn fiber, nutshells, almond shells, coconut shells, bagasse, cottonseed bran, and cottonseed skins. When wood is used as a starting material, it is advantageously used as chips or sawdust. Preferably, the biomass is selected from hardwood, such as birch and *eucalyptus*, bagasse, and sugarcane leaves, or a combination thereof.

A schematic of exemplary conversion processes to convert biomass to a refined hemicellulose sugar stream is provided in FIG. 1. Optionally, lignocellulose-containing biomass is pre-treated (1770) prior to extracting hemicellulose sugars. In some examples, pretreatment of the biomass is not required, i.e., the lignocellulose-containing biomass can be used directly in the hemicellulose sugar extraction. A schematic diagram of exemplary counter current processes for washing biomass is provided in FIG. 8. Pretreatment may comprise a reduction in biomass size (e.g., mechanical breakdown, milling, or grinding). Optionally, the lignocellulose-containing biomass is ground such that the average size of the resultant biomass particles is between about 100 to 1,000 microns, such as about 400-5,000 microns, about 100-400 microns, about 400-1,000 microns, about 1,000-3,000 microns, about 3,000-5,000 microns, or about 5,000-10,000 microns. The average size of the ground biomass particles may be less than 10,000 microns, less than 9,000 microns, less than 8,000 microns, less than 7,000 microns, less than 6,000 microns, less than 5,000 microns, less than 4,000 microns, less than 3,000 microns, less than 2,000 microns, less than 1,000 microns, or less than 500 microns.

Pretreatment of the lignocellulose-containing biomass may comprise reducing ash and soil content of the biomass prior to extracting hemicellulose sugars from the biomass. In some examples, lignocellulose-containing biomass comprising greater than about 4% wt/wt, greater than about 5% wt/wt, greater than about 6% wt/wt, greater than about 7% wt/wt, or greater than about 8% wt/wt apparent ash (as measured by ashing a dry sample of the biomass according to NREL/TP-510-42622) is de-soiled and de-ashed. Ash values greater than about 4% may be indicative of physical incorporation of soil particles in the biomass during the growing season, wherein the soil particles contact and are encased by the biomass as it grows. Reducing ash and soil content of the biomass may comprise one or more stages of slurrying, washing, and dewatering the biomass. A method for reducing ash and soil content may comprise at least one and up to n stages of re-slurry and milling (e.g., grinding) the biomass, and at least one and up to m stages of washing and dewatering the biomass, wherein n is 2, 3, 4, 5, 6, 7, 8, 9 or 10 and m is 2, 3, 4, 5, 6, 7, 8, 9 or 10. Optionally, n is equal to m. In some examples, m is greater than n or n is greater than m. Two or more such cycles of shear treatment and high pressure washing may be necessary to reduce the ash content of the biomass to less than 6%, less than 5%, less than 4%, or less than 3% wt/wt ash.

Hemicellulose sugars may be extracted from lignocellulosic biomass by any suitable method (1700), for example, using an aqueous acidic solution. The aqueous acidic solution may comprise any acid, such as an inorganic acid or an organic acid. Preferably, the solution comprises an inorganic acid, such as $H_2SO_4$, $H_2SO_3$ (which can be introduced as dissolved acid or as $SO_2$ gas), or HCl. In some examples, the aqueous acidic solution may comprise an inorganic and/or an organic acid, including, for example, $H_2SO_4$, $H_2SO_3$, HCl, or acetic acid, or combinations thereof. The acidic aqueous solution can contain an acid in an amount of about 0 to 2% acid or more, such as about 0-1.0%, about 0-1.5%, about 0.5-1.5%, about 0.5-2.0%, about 1.0-2.0%, about 1.5-2.0%, about 0.2-1.0%, about 0.2-0.7%, about 0-0.2%, about 0.2-0.4%, about 0.4-0.6%, about 0.6-0.8%, about 0.8-1.0%, about 1.0-1.2%, about 1.2-1.4%, about 1.4-1.6%, about 1.6-1.8%, or about 1.8-2.0% wt/wt. Optionally, the aqueous solution for the extraction includes 0.2-0.7% $H_2SO_4$ and 0-3,000 ppm $SO_2$. The pH of the acidic aqueous solution may be in the range of about pH 1 to pH 5, such as about pH 1 to pH 3.5.

Elevated temperature or pressure may be used to extract hemicellulose sugars from biomass. In some examples, a temperature in the range of about 100-200° C. is used. A temperature of greater than 50° C., greater than 60° C., greater than 70° C., greater than 80° C., greater than 90° C., greater than 100° C., greater than 110° C., greater than 120° C., greater than 130° C., greater than 140° C., greater than 150° C., greater than 160° C., greater than 170° C., greater than 180° C., greater than 190° C., or greater than 200° C. can be used in the extraction. Preferably, the temperature is in the range of 90-170° C., such as 100-165° C., 110-160° C., 120-150° C., 130-155° C. or 140-150° C. The pressure can be in the range of about 0.4-10 mPa, such as 0.4-5 mPa. Optionally, the pressure is less than 20 mPa, such as less than 10 mPa, less than 9 mPa, less than 8 mPa, less than 7 mPa, less than 6 mPa, or less than 5 mPa. In some examples, the extraction mixture is heated for 0.1-5 hours, preferably 0.1-3 hours, 0.1-1 hour, 0.5-1.5 hours, 0.5-2 hours, 1-2 hours, or 2-3 hours. The extraction process can have a cooling down period of less than one hour. Optionally, hemicellulose sugars are extracted from biomass by contacting the biomass with an aqueous acidic solution and heating the resultant mixture to a temperature of greater than 50° C. at a pressure of less than 10 mPa.

Hemicellulose sugar extraction can produce, in one single extraction process, a hemicellulose sugar stream (1700-A) containing at least 75% monomeric sugars, such as more than 80%, more than 85%, more than 90%, more than 91%, more than 92%, more than 93%, more than 94%, more than 95%, more than 96%, more than 97%, more than 98%, or more than 99% monomeric sugars. The hemicellulose sugar stream may contain 80-99% monomeric sugars. In some examples, at least about 70%, at least 75%, at least 80%, at least 85%, at least 90%, or even at least 95% or more of the hemicellulose sugars present in the biomass can be extracted using a method of the disclosure. Hemicellulose sugar extraction may produce minimal amounts of lignocellulose degradation products, such as furfural, hydroxymethyl furfural, levulinic acid, and formic acid. A xylose yield of greater than 70%, optionally greater than 80%, of theoretical value can be achieved.

Figure 9:
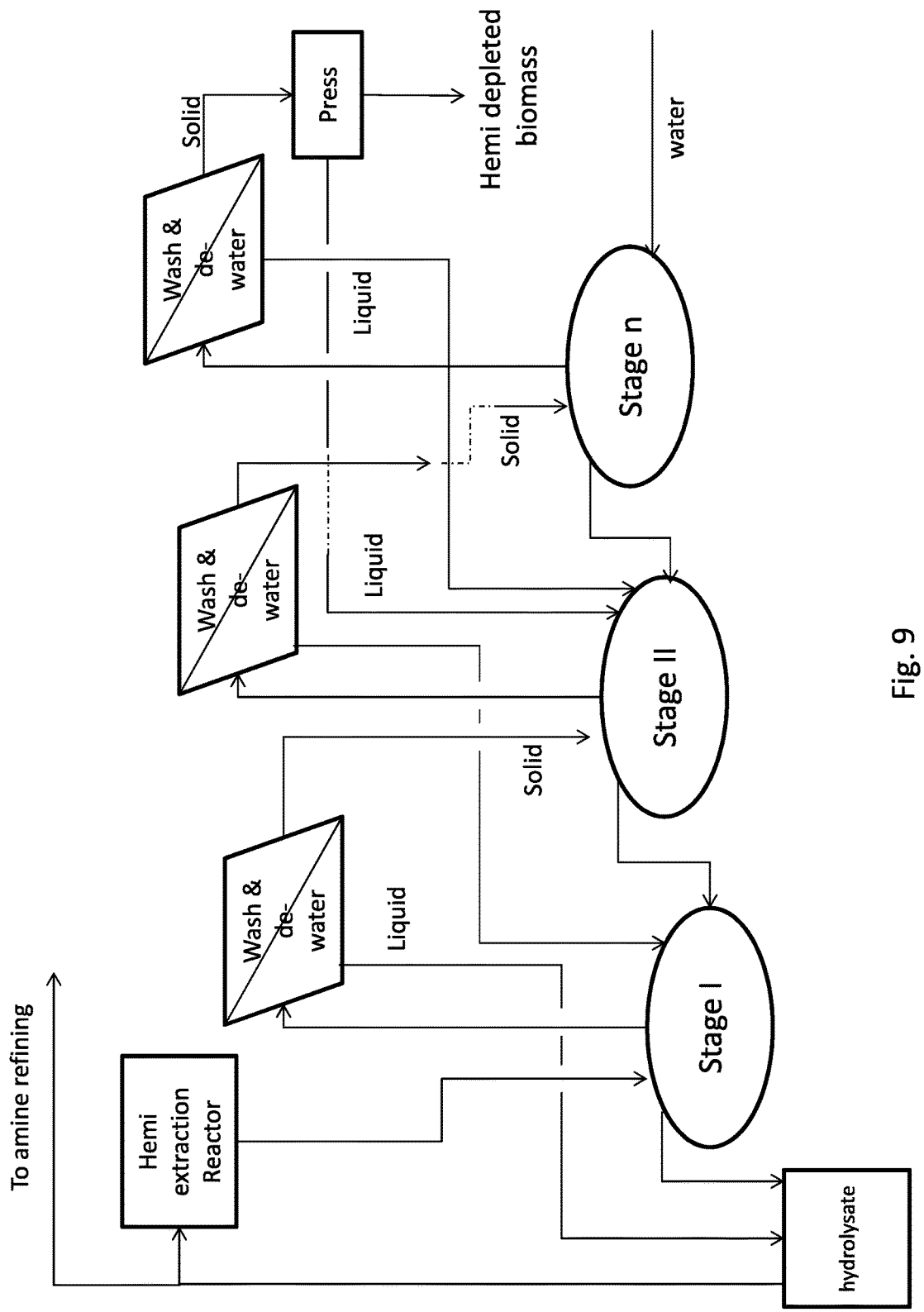
FIG. 9 illustrates a schematic diagram of exemplary sequential processes for washing and de-watering lignocellulosic biomass after extraction of hemicellulose sugars.

The extraction of hemicellulose sugars from the biomass results in a lignocellulose remainder stream (1700-P1) comprising lignin and cellulose. A schematic diagram of exemplary sequential processes for washing and de-watering a lignocellulose remainder stream after extraction of hemicellulose sugars is provided in FIG. 9. In some examples, the extraction of hemicellulose sugars does not remove a substantial amount of the cellulosic sugars. For example, extraction of hemicellulose sugars does not remove more than 1%, more than 2%, more than 5%, more than 10%, more than 15%, more than 20%, more than 30%, more than 40%, more than 50%, or more than 60% weight/weight cellulose. In some examples, the lignocellulose remainder stream comprises less than 50%, less than 45%, less than 40%, less than 35%, less than 30%, less than 25%, less than 20%, less than 15%, less than 10%, less than 5%, less than 2%, or less than 1% weight/weight hemicellulose. The lignocellulose remainder stream may comprise less than 10%, less than 9%, less than 8%, less than 7%, less than 6%, less than 5%, less than 4%, less than 3%, less than 2%, or less than 1% weight/weight ash. In some examples, the lignocellulose remainder stream comprises 0.001-5% weight/weight ash, such as 0.01-4%, 0.1-3%, 0.1-2%, or 0.1-1% weight/weight ash. In some examples, the lignocellulose remainder stream comprises lignin, cellulose, hemicellulose in an amount less than 5% weight/weight, and ash in an amount less than 4% weight/weight. In some examples, less than 10%, less than 5%, less than 4%, less than 3%, less than 2.5%, less than 2%, less than 1.5%, or less than 1% of the lignocellulose solids remain in the hemicellulose sugar stream. Optionally, the lignocellulose remainder stream comprises less than 75%, less than 65%, less than 55%, less than 45%, less than 35%, less than 25%, less than 15%, or less than 10% weight/weight water. The lignocellulose remainder stream may comprise more than 20%, more than 30%, more than 40%, more than 50%, more than 60%, more than 70%, or more than 80% weight/weight solids. The lignocellulose remainder stream may comprise less than 10%, less than 7.5%, less than 5%, less than 4%, less than 3%, less than 2%, less than 1%, or less than 0.5% weight/weight residual soluble carbohydrates. In some examples, the lignocellulose remainder stream comprises about 0.01-5% weight/weight soluble carbohydrates, such as 0.1-5%, 0.5-5%, 0.5-2.5%, or 0.1-2.5% weight/weight soluble carbohydrates. The lignocellulose remainder stream may comprise less than 5%, less than 4%, less than 3%, less than 2%, less than 1%, less than 0.5%, less than 0.2%, or less than 0.1% weight/weight sulfate. In some examples, the lignocellulose remainder stream comprises 0.001-3% weight/weight sulfate, such as 0.01-3%, 0.01-2%, 0.01-1%, or 0.001-1% weight/weight sulfate. The lignocellulose remainder stream may comprise soluble carbohydrates in an amount relative to total solids of less than 5%, ash in an amount relative to total solids of less than 4%, and sulfate in an amount relative to total solids of less than 3%.

Impurities such as ash, acid soluble lignin, furfural, fatty acids, organic acids such as acetic acid and formic acid, methanol, proteins and/or amino acids, glycerol, sterols, rosin acid or waxy materials, or combinations thereof, can be extracted together with the hemicellulose sugars under the same conditions into the hemicellulose sugar stream. At least some of these impurities can be separated from the hemicellulose sugar stream by solvent extraction (e.g., using an amine extractant).

The hemicellulose sugar stream can be refined and optionally fractionated according to processes disclosed in PCT/US2013/039585, incorporated herein by reference. The hemicellulose sugar stream can be optionally filtered, centrifuged, or concentrated by evaporation. Optionally, the hemicellulose sugar stream is contacted with a strong acid cation exchanger (e.g., in $H^+$ form) to convert salts to the respective acids. In some examples, the hemicellulose sugar stream is first contacted with a strong cation exchange resin and then contacted with an amine extractant.

Figure 3:
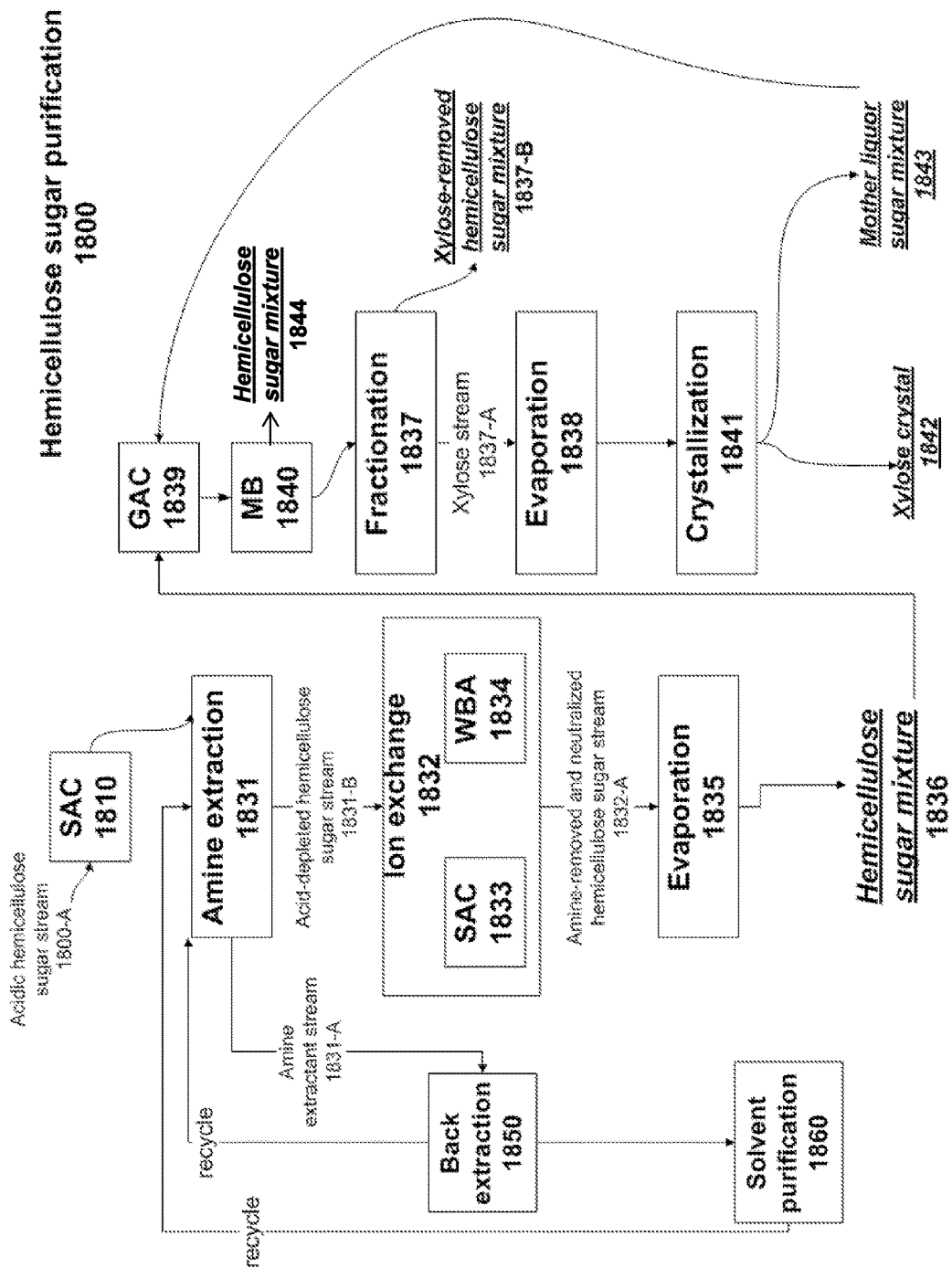
FIG. 3 illustrates a schematic diagram of exemplary conversion processes for the purification of an acidic hemicellulose sugar stream.

Optionally, impurities are removed from the hemicellulose sugar stream by contacting the stream with an amine extractant to form a mixture, wherein the mixture may comprise an organic stream and an aqueous stream (1710). Exemplary conversion processes for the purification of the hemicellulose sugar stream (1700-A and 1800-A) are depicted in FIG. 3, including amine extraction 1831. In some examples, the organic stream (1831-A) comprises the amine extractant and at least one impurity. Optionally, the at least one impurity is selected from a mineral acid (e.g., $H_2SO_4$, $H_2SO_3$, and HCl), an organic acid (e.g., acetic acid and formic acid), furfural, hydroxymethylfurfural, and acid soluble lignin. The aqueous stream may comprise hemicellulose sugars. After separation from the organic stream, the aqueous stream is referred to herein as a refined hemicellulose sugar stream (1710-P1 and 1831-B).

The amine extractant may comprise 10-90%, such as 10-80%, 10-70%, 10-60%, 10-50%, 10-40%, 20-80%, 20-70%, 20-60%, 20-50%, 20-40%, 15-80%, 15-70%, 15-60%, 15-50%, 15-40%, 15-35%, 25-80%, 25-70%, 25-60%, 25-50%, 25-40%, or 25-35% weight/weight of one or more amines having at least 20 carbon atoms. Such amine(s) can be primary, secondary, or tertiary amines. Examples of tertiary amines include trilaurylamine (TLA; e.g. COGNIS ALAMINE 304 from Cognis Corporation; Tucson Ariz.; USA), trioctylamine, tri-isooctylamine, tri-caprylylamine and tri-decylamine.

The amine extractant may further comprise a diluent. In some examples, the amine extractant comprises at least 10%, at least 20%, at least 30%, at least 40%, at least 50%, at least 60%, at least 70%, at least 80%, or at least 90% weight/weight, such as 55-85% weight/weight, of a diluent. Optionally, the diluent is an alcohol, such as butanol, isobutanol, pentanol, hexanol, octanol, decanol, dodecanol, tetradecanol, pentadecanol, hexadecanol, octadecanol, eicosanol, docosanol, tetracosanol, and triacontanol. Optionally, the diluent is a long chain alcohol (e.g. C6, C8, C10, C12, C14, C16 alcohol), or kerosene. In some examples, the diluent is n-hexanol or 2-ethyl-1-hexanol. Optionally, the diluent is 2-ethyl-1-hexanol. In some examples, the diluent comprises one or more additional components, such as a ketone, an aldehyde having at least 5 carbon atoms, or another alcohol.

Optionally, the amine extractant comprises an amine having at least 20 carbon atoms and a diluent (e.g., an alcohol), such as a tertiary amine having at least 20 carbon atoms and an alcohol. In some examples, the amine extractant comprises a tertiary amine having from 20 to 50 carbon atoms and a diluent, wherein the diluent is a $C_{6-12}$ monoalcohol. In some examples, the amine extractant comprises an amine having from 24-40 carbon atoms (e.g., trilaurylamine, trioctylamine, tricaprylamine, or tridecylamine) and a diluent, wherein the diluent is a $C_{6-12}$ monoalcohol (e.g., hexanol, octanol, or 2-ethylhexanol). In some examples, the amine is trilaurylamine and the diluent is hexanol or 2-ethylhexanol.

The amine extractant can comprise an amine and a diluent in a ratio between 1:10 and 10:1 weight/weight, such as 1:9, 1:4, 3:7, 2:3, 1:1, 3:2, 7:3, 4:1, or 9:1 weight/weight. Optionally, the amine extractant comprises trilaurylamine and a $C_{6-12}$ monoalcohol in a ratio of 1:7, 2:7, 3:7, 6:4, 5.5:4.55, 4:7, 5:7, 6:7, 7:7, 5:4, 3:4, 2:4, or 1:4 weight/weight. Optionally, the amine extractant comprises trilaurylamine and a $C_{6-12}$ monoalcohol in a ratio of about 3:7 weight/weight, such as a 3:7 weight/weight ratio of trilaurylamine and hexanol.

Optionally, the hemicellulose sugar stream is extracted with an amine extractant counter-currently, e.g., the hemicellulose sugar stream flows in a direction opposite to the flow of the amine extractant. The amine extraction can be conducted at any temperature at which the amine is soluble, such as 50-70° C. Optionally, the amine extraction comprises more than one extraction step (e.g., 2, 3, or 4 steps). The ratio of the amine extractant stream (organic stream) to the hemicellulose sugar stream (aqueous stream) can range from about 0.5:1 to about 5:1 weight/weight, such as about 0.5:1, about 1:1, about 1.5:1, about 2:1, about 2.5:1, about 3:1, about 3.5:1, about 4:1, about 4.5:1, or about 5:1. In some examples, the ratio of the organic stream to the aqueous stream is about 1.5-3.0:1 weight/weight.

After contacting the hemicellulose sugar stream with the amine extractant, the resulting mixture can be separated into an organic stream (i.e., the organic phase) comprising the amine extractant and at least one impurity and a refined hemicellulose sugar stream (i.e., the aqueous phase). At least a portion of organic acids or inorganic acids (e.g., the acids used in hemicellulose sugar extraction) and other impurities may be extracted into the organic stream. In some examples, the organic stream is contacted with an aqueous stream in a counter current mode to recover any residual sugars absorbed into the organic stream. The organic stream may comprise less than 5%, less than 4%, less than 3%, less than 2%, less than 1%, less than 0.8%, less than 0.6%, less than 0.5%, less than 0.4%, less than 0.3%, less than 0.2%, or less than 0.1% weight/weight hemicellulose sugars, such as 0.01% to 4% hemicellulose sugars. In some examples, the refined hemicellulose sugar stream comprises less than 3%, less than 2%, less than 1%, less than 0.8%, less than 0.6%, less than 0.5%, less than 0.4%, less than 0.3%, less than 0.2%, or less than 0.1% weight/weight acid, such as 0.01% to 3% acid. In some examples, the refined hemicellulose sugar stream comprises less than 5%, less than 4%, less than 3%, less than 2%, less than 1%, less than 0.8%, less than 0.6%, less than 0.5%, less than 0.4%, less than 0.3%, less than 0.2%, or less than 0.1% weight/weight of an amine having at least 20 carbon atoms, such as 0.01% to 4% of an amine. In some examples, the refined hemicellulose sugar stream comprises less than 5%, less than 4%, less than 3%, less than 2%, less than 1%, less than 0.8%, less than 0.6%, less than 0.5%, less than 0.4%, less than 0.3%, less than 0.2%, or less than 0.1% weight/weight of an impurity, such as 0.1% to 4% of an impurity, wherein the impurity is selected from ash, acid soluble lignin, furfural, fatty acids, organic acids such as acetic acid and formic acid, mineral acids such as hydrochloric acid and sulfuric acid, furfural, hydroxymethylfurfural, methanol, proteins, amino acids, glycerol, sterols, rosin acid, and waxy materials. The refined hemicellulose sugar stream may comprise less than 5%, less than 4%, less than 3%, less than 2%, less than 1%, less than 0.8%, less than 0.6%, less than 0.5%, less than 0.4%, less than 0.3%, less than 0.2%, or less than 0.1% weight/weight furfural, such as 0.1% to 4% of furfural. In some examples, the refined hemicellulose sugar stream comprises less than 5%, less than 4%, less than 3%, less than 2%, less than 1%, less than 0.8%, less than 0.6%, less than 0.5%, less than 0.4%, less than 0.3%, less than 0.2%, or less than 0.1% weight/weight ash, such as 0.1% to 4% of ash.

The refined hemicellulose sugar stream can be further purified. For example, residual diluent in the refined hemicellulose sugar stream can be removed using a packed distillation column. The distillation can remove at least 70%, at least 80%, at least 90%, or at least 95% of residual diluent in the refined hemicellulose sugar stream. In some examples, the refined hemicellulose sugar stream is contacted with a strong acid cation (SAC) exchanger (1833) to remove residual metallic cations and residual amines, then optionally contacted with a weak base anion (WBA) exchanger (1834) to remove excess protons. Optionally, the refined hemicellulose sugar stream is purified using a distillation column (e.g., a packed distillation column) followed by a strong acid cation exchanger. In some examples, the refined hemicellulose sugar stream is contacted with a weak base anion (WBA) exchanger to remove excess protons. The refined hemicellulose sugar stream can be pH adjusted, optionally after contacting the stream with a SAC exchanger and/or WBA exchanger. The refined hemicellulose sugar stream can be distilled or evaporated, then further polished by contacting with a SAC resin, a WBA resin, and a MB resin, and optionally concentrated by evaporation. In some examples, the refined hemicellulose sugar stream is evaporated (1835) to 20-80% weight/weight dissolved sugars, such as 25-65% or 30-40% weight/weight dissolved sugars, thereby forming a concentrated sugar solution (1836). The evaporation may be conducted in any conventional evaporator, e.g., a multiple effect evaporator or a mechanical vapor recompression (MVR) evaporator.

Residual solvent present in the hemicellulose sugar stream or concentrated sugar solution can also be removed by evaporation. For example, a solvent that forms a heterogeneous azeotrope with water can be separated and optionally returned to the solvent cycle. Optionally, the refined hemicellulose sugar stream can be contacted with activated carbon to remove residual organic impurities. The refined hemicellulose sugar stream may also be contacted with mixed bed resin system to remove any residual ions or color bodies.

The refined hemicellulose sugar stream produced by the subject systems and methods can comprise sugars in a ratio highly suitable as feed for fermentation, such as for the production of xylitol.

In some examples, the refined hemicellulose sugar stream comprises at least 40%, at least 45%, at least 50%, at least 55%, at least 60%, at least 65%, at least 70%, at least 75%, at least 80%, at least 85%, at least 90%, or at least 95% weight/weight xylose relative to total dissolved sugars. Optionally, the refined hemicellulose sugar stream comprises between 40% and 95% weight/weight xylose relative to total dissolved sugars, such as 50% to 85% xylose.

In some examples, the refined hemicellulose sugar stream comprises less than 15%, less than 14%, less than 13%, less than 12%, less than 11%, less than 10%, less than 9%, less than 8%, less than 7%, less than 6%, less than 5%, less than 4%, less than 3%, or less than 2% weight/weight arabinose relative to total dissolved sugars. Optionally, the refined hemicellulose sugar stream comprises between 1% and 15% weight/weight arabinose relative to total dissolved sugars, such as 3% to 12% arabinose.

In some examples, the refined hemicellulose sugar stream comprises at least 5%, at least 10%, at least 12%, at least 15%, at least 17%, at least 20%, at least 22%, at least 25%, at least 27%, at least 30%, at least 32%, at least 35%, at least 37%, at least 40%, at least 42%, at least 45%, at least 50%, at least 52%, at least 55%, or at least 57% weight/weight hexoses relative to total dissolved sugars. Optionally, the refined hemicellulose sugar stream comprises between 5% and 60% weight/weight hexoses relative to total dissolved sugars, such as 10% to 45% hexoses.

In some examples, the hexoses comprise glucose, galactose, mannose and fructose, wherein glucose and fructose optionally comprise at least 30%, at least 40%, at least 45%, at least 50%, at least 55%, at least 60%, at least 65%, at least 70%, at least 75%, or at least 80% weight/weight of the hexoses. Optionally, the refined hemicellulose sugar stream comprises between 30% and 85% weight/weight glucose and fructose relative to hexoses, such as 50% to 80% glucose and fructose.

In some examples, the refined hemicellulose sugar stream comprises at least 5%, at least 10%, at least 12%, at least 15%, at least 17%, at least 20%, at least 22%, at least 25%, at least 27%, at least 30%, at least 32%, at least 35%, at least 37%, at least 40%, at least 42%, at least 45%, at least 50%, at least 52%, at least 55%, or at least 57% weight/weight glucose relative to total dissolved sugars. Optionally, the refined hemicellulose sugar stream comprises between 5% and 60% weight/weight glucose relative to total dissolved sugars, such as 10% to 45% glucose.

In some examples, the refined hemicellulose sugar stream comprises xylose in a ratio to hexoses of at least 1:1 weight/weight, such as at least 1.5:1, at least 2:1, at least 3:1, at least 4:1, at least 5:1, at least 6:1, or at least 7:1 weight/weight. Optionally, the ratio of xylose to hexoses in the refined hemicellulose sugar stream is between 1:1 and 8:1 weight/weight, such as between 1.5:1 and 5:1 weight/weight.

In some examples, the refined hemicellulose sugar stream comprises less than 15%, less than 10%, less than 9%, less than 8%, less than 7%, less than 6%, less than 5%, less than 4%, less than 3%, less than 2%, or less than 1% weight/weight disaccharides relative to total dissolved sugars. Optionally, the refined hemicellulose sugar stream comprises between 0.1% and 15% weight/weight disaccharides relative to total dissolved sugars, such as 0.5% to 8% disaccharides.

In some examples, the refined hemicellulose sugar stream comprises less than 16%, less than 14%, less than 12%, less than 10%, less than 8%, less than 6%, less than 5%, less than 4%, less than 3%, less than 2%, less than 1%, or less than 0.5% weight/weight oligosaccharides relative to total dissolved sugars, wherein said oligosaccharides comprise at least 3 monosaccharide units. Optionally, the refined hemicellulose sugar stream comprises between 0.1% and 10% weight/weight oligosaccharides relative to total dissolved sugars, such as 0.5% to 5% oligosaccharides.

In some examples, the refined hemicellulose sugar stream comprises ash in an amount up to 2%, up to 1.5%, up to 1%, up to 0.75%, up to 0.50%, up to 0.25%, up to 0.1%, or up to 0.05% weight/weight ash. Optionally, the refined hemicellulose sugar stream comprises between 0.001% and 1% weight/weight ash, such as 0.001% to 0.25% ash.

In some examples, the ash comprises Ca, Cu, Fe, K, Mg, Mn, Na, P, S, or Si, or a combination thereof. In some examples, the refined hemicellulose sugar stream comprises Ca, Cu, Fe, K, Mg, Mn, Na, P, S, and Si at less than 1000 ppm, less than 750 ppm, less than 500 ppm, less than 400 ppm, less than 300 ppm, less than 200 ppm, less than 100 ppm, less than 50 ppm, or less than 10 ppm each. Optionally, the refined hemicellulose sugar stream comprises between 1 ppm and 1000 ppm each of Ca, Cu, Fe, K, Mg, Mn, Na, P, S, and Si, such as 1 ppm to 250 ppm each of Ca, Cu, Fe, K, Mg, Mn, Na, P, S, and Si. In some examples, the refined hemicellulose sugar stream comprises less than 1000 ppm, less than 750 ppm, less than 500 ppm, less than 400 ppm, less than 300 ppm, less than 200 ppm, less than 100 ppm, less than 50 ppm, or less than 10 ppm calcium. Optionally, the refined hemicellulose sugar stream comprises between 1 ppm and 1000 ppm of calcium, such as 1 ppm to 250 ppm calcium.

In some examples, the refined hemicellulose sugar stream comprises phenolic compounds in amounts up to 1000 ppm, up to 750 ppm, up to 500 ppm, up to 400 ppm, up to 300 ppm, up to 200 ppm, up to 100 ppm, up to 50 ppm, or up to 10 ppm. Optionally, the refined hemicellulose sugar stream comprises between 1 ppm and 1000 ppm phenolic compounds, such as 1 ppm to 250 ppm phenolic compounds.

In some examples, the refined hemicellulose sugar stream comprises furfural in an amount up to 1000 ppm, up to 750 ppm, up to 500 ppm, up to 400 ppm, up to 300 ppm, up to 200 ppm, up to 100 ppm, up to 50 ppm, or up to 10 ppm. Optionally, the refined hemicellulose sugar stream comprises between 1 ppm and 1000 ppm of furfural, such as 1 ppm to 250 ppm furfural.

In some examples, the refined hemicellulose sugar stream comprises less than 1000 ppm, less than 750 ppm, less than 500 ppm, less than 400 ppm, less than 300 ppm, less than 200 ppm, less than 100 ppm, less than 50 ppm, or less than 10 ppm organic acids, such as acetic acid, levulinic acid, formic acid, and lactic acid. Optionally, the refined hemicellulose sugar stream comprises between 1 ppm and 1000 ppm organic acids, such as 1 ppm to 250 ppm organic acids. Optionally, the refined hemicellulose sugar stream comprises between 1 ppm and 1000 ppm of acetic acid, such as 1 ppm to 250 ppm acetic acid. Optionally, the refined hemicellulose sugar stream comprises between 1 ppm and 1000 ppm of formic acid, such as 1 ppm to 250 ppm formic acid.

In some examples, the refined hemicellulose sugar stream comprises an amine in an amount up to 1000 ppm, up to 750 ppm, up to 500 ppm, up to 400 ppm, up to 300 ppm, up to 200 ppm, up to 100 ppm, up to 50 ppm, or up to 10 ppm, and wherein the amine comprises at least 12 carbon atoms. Optionally, the amine is a laurylamine, such as monolaurylamine, dilaurylamine, or trilaurylamine. Optionally, the refined hemicellulose sugar stream comprises between 0.1 ppm and 1000 ppm of an amine comprising at least 12 carbon atoms, such as 0.1 ppm to 250 ppm of an amine comprising at least 12 carbon atoms.

In some examples, the refined hemicellulose sugar stream comprises an alcohol in an amount up to 1000 ppm, up to 750 ppm, up to 500 ppm, up to 400 ppm, up to 300 ppm, up to 200 ppm, up to 100 ppm, up to 50 ppm, or up to 10 ppm. The alcohol can be any alcohol that can be used herein as a diluent, such as butanol, pentanol, hexanol, or 2-ethyl-1-hexanol. In some examples, the alcohol is a $C_{6-12}$ monoalcohol, optionally present in the refined hemicellulose sugar stream in an amount up to 200 ppm. Optionally, the refined hemicellulose sugar stream comprises between 1 ppm and 1000 ppm of said alcohol, such as 1 ppm to 250 ppm of said alcohol.

In some examples, the refined hemicellulose sugar stream comprises nitrogen in an amount up to 1000 ppm, up to 750 ppm, up to 500 ppm, up to 400 ppm, up to 300 ppm, up to 200 ppm, or up to 150 ppm. Optionally, the refined hemicellulose sugar stream comprises between 1 ppm and 1000 ppm of nitrogen, such as 1 ppm to 250 ppm nitrogen. Nitrogen may be total Kjeldahl nitrogen measured using the Kjeldahl method.

In some examples, the refined hemicellulose sugar stream comprises: at least 50% weight/weight xylose; arabinose in an amount up to 12% weight/weight; at least 10% weight/weight hexoses; disaccharides in an amount up to 8% weight/weight; ash in an amount up to 0.25% weight/weight; furfural in an amount up to 200 ppm; and nitrogen in an amount up to 1000 ppm. In some examples, the refined hemicellulose sugar stream comprises: at least 50% weight/weight xylose; between 3% and 12% weight/weight arabinose; at least 10% weight/weight hexoses; between 0.001% and 0.25% weight/weight ash; between 1 ppm and 200 ppm furfural; and between 1 ppm and 1000 ppm nitrogen. Optionally, the refined hemicellulose sugar stream comprises 65-75% xylose, 3-10% arabinose and 15-25% hexoses (all weight/weight relative to total dissolved sugars). The refined hemicellulose sugar stream can contain at least 90% weight/weight saccharides relative to total dissolved solids, such as at least 91%, at least 92%, at least 93%, at least 94%, at least 95%, at least 96%, at least 97%, at least 98%, at least 99%, or at least 99.5% saccharides.

The refined hemicellulose sugar stream can have a high purity with respect to ash elements, organic acids, lignin derivatives and sugar degradation products. The refined hemicellulose sugar stream may comprise ash at a concentration of up to 1%, up to 0.5%, up to 0.1%, up to 0.05%, or up to 0.01% weight/weight relative to total dissolved sugars, wherein the ash comprises up to 500 ppm, up to 250 ppm, or up to 100 ppm metallic cations and less than 100 ppm, less than 50 ppm, less than 30 ppm, or less than 20 ppm sulfur relative to total dissolved sugars. In some examples, a refined hemicellulose sugar stream is particularly suitable for fermentation processes that are sensitive to ash elements or to sulfur compounds. The refined hemicellulose sugar stream can comprise less than 5000 ppm ash in total weight/weight relative to xylose, wherein the ash comprises elements selected from Na, Ca, Cu, Fe, K, Mg, Mn, S and P.

In some examples, the refined hemicellulose sugar stream comprises at least one characteristic selected from: (i) a ratio of disaccharides to total dissolved sugars of not more than 0.10 weight/weight; (ii) a ratio of xylose to total dissolved sugars of at least 0.70 weight/weight; (iii) a ratio of arabinose to total dissolved sugars of not more than 0.06 weight/weight; (iv) a ratio of galactose to total dissolved sugars of not more than 0.05 weight/weight; (v) a ratio of the sum of the glucose and fructose to total dissolved sugars of not more than 0.15 weight/weight; (vi) a ratio of mannose to total dissolved sugars of not more than 0.05 weight/weight; (vii) a ratio of fructose to total dissolved sugars of not more than 0.10 weight/weight; (viii) phenolic compounds in an amount of not more than 1000 ppm; (ix) hexanol in an amount of not more than 0.1% weight/weight: (x) furfural in an amount of not more than 1000 ppm; (xi) organic acids in an amount of not more than 1000 ppm; and (xii) less than 1000 ppm each of the elements Ca, Cu, Fe, K, Mg, Mn, S and P relative to total dissolved sugars.

In some examples, the refined hemicellulose sugar stream comprises low levels of additional monosaccharides and disaccharides. Optionally, the additional monosaccharides are selected from lyxose, xylulose, and ribulose. Optionally, the additional disaccharides are selected from gentiobiose, sophorose, nigerose, laminaribiose, and kojibiose. These additional monosaccharides and disaccharides may be beneficial to fermentation processes. In some examples, such rare saccharides are biologically active and may act as promoters to increase activity of enzymatic expression or work as cofactors to increase activity of the enzymes, thus resulting in accelerated biological conversion.

Surprisingly, the refined hemicellulose sugar stream is particularly advantageous in a fermentation process capable of hydrogenating xylose to xylitol, as the fermenting species can utilize the hexoses as their energy source, thus, in some examples, eliminating the need to further purify or fractionate the sugar stream prior to the hydrogenation step. Further purification steps commonly used to enrich the xylose content of a sugar stream, such as chromatographic separation or crystallization, may not be necessary before fermentation. In certain examples, the ratios of sugars in the refined hemicellulose sugar stream are ideal for fermentation to xylitol, wherein enriching the concentration of xylose may reduce the efficiency and yield of the fermentation process. It is further realized that the high purity of the refined hemicellulose sugar stream is advantageous as feed for fermentation, as the concentrations of impurities known as possible fermentation inhibitors, such as phenols, furfurals, organic acids, and alcohols, is low.

Figure 2A:
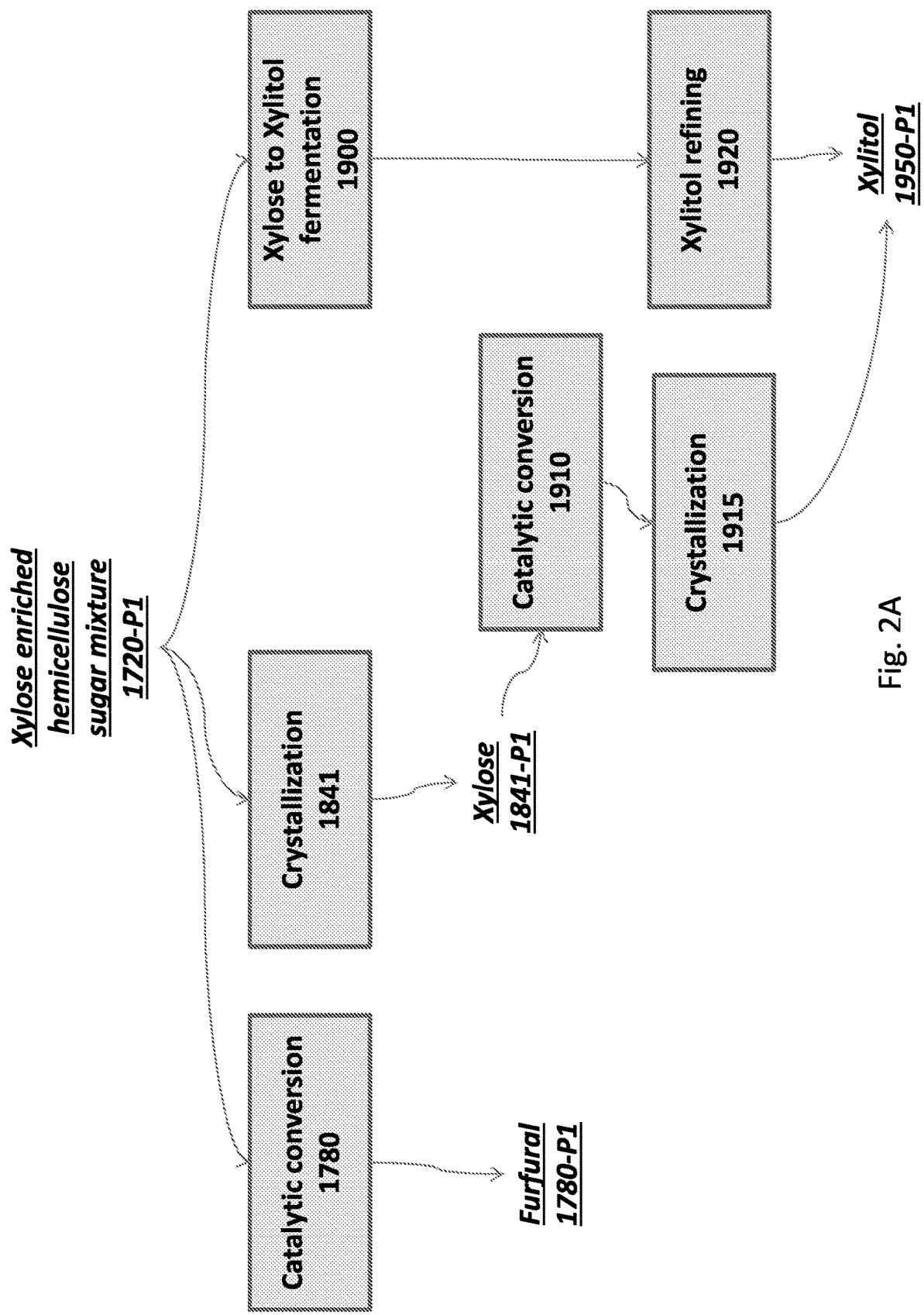
FIG. 2A illustrates a schematic diagram of exemplary conversion processes to convert a xylose enriched hemicellulose sugar mixture to downstream products such as xylitol, xylose, and furfural.
Figure 2B:
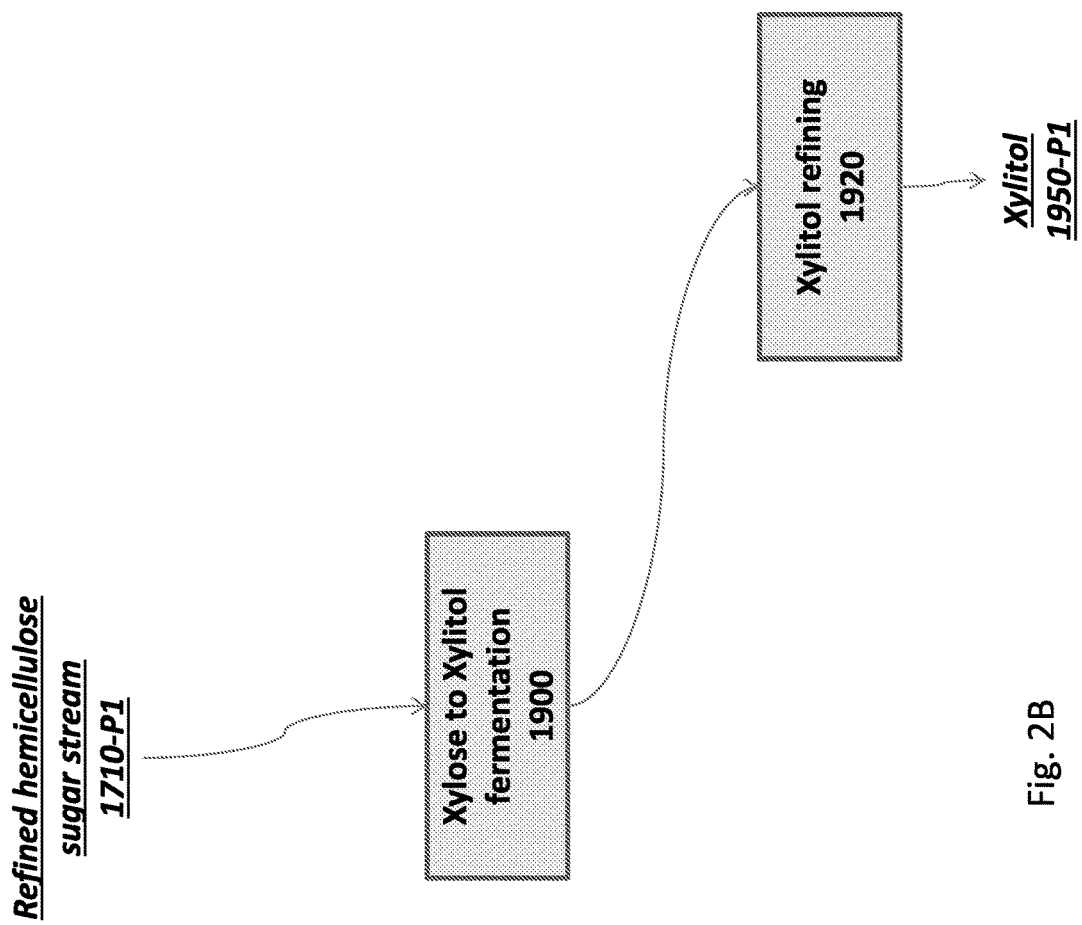
FIG. 2B illustrates a schematic diagram of an exemplary process to convert a refined hemicellulose sugar stream to xylitol.
Figure 4:
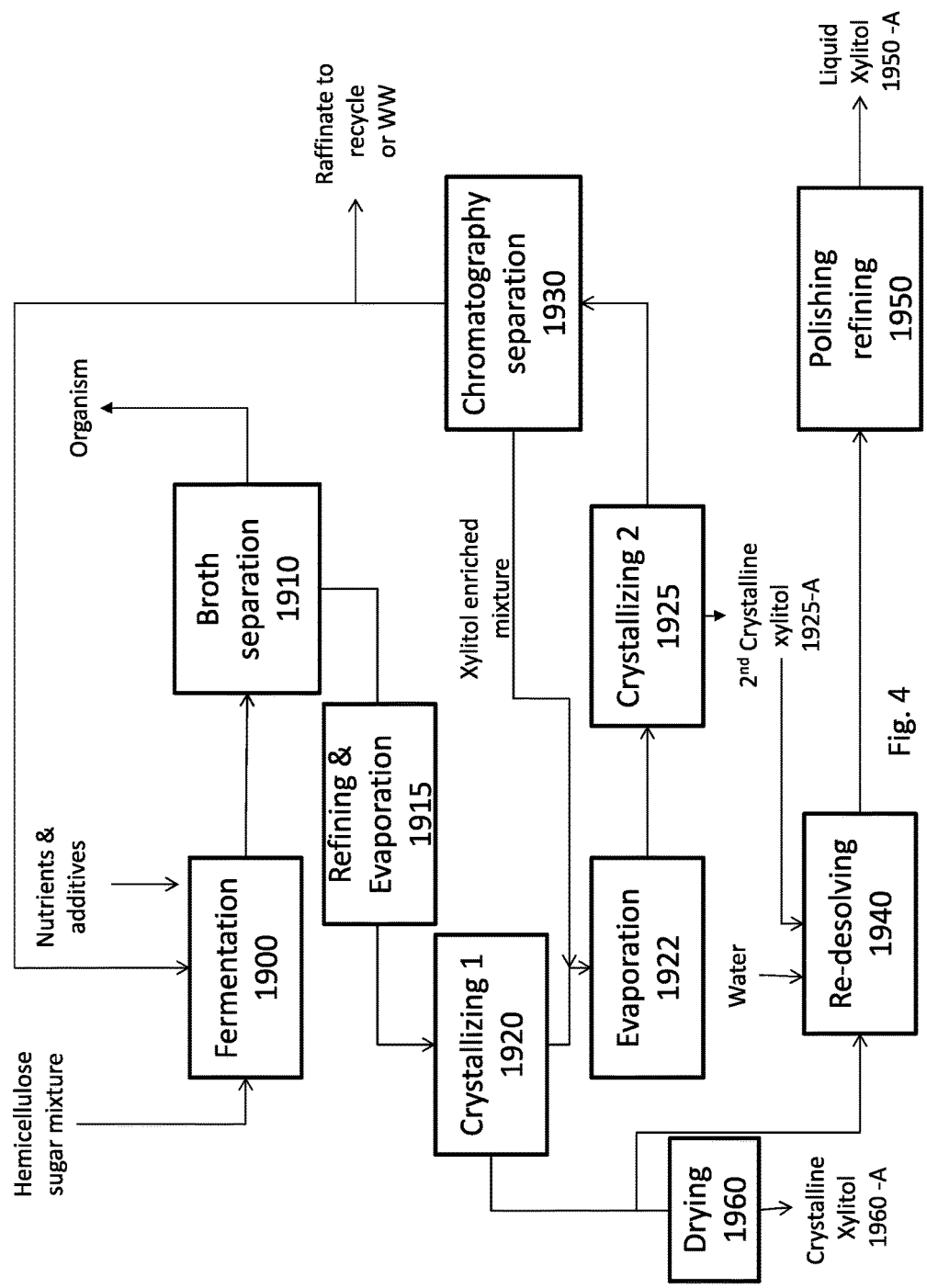
FIG. 4 illustrates a schematic diagram of an exemplary conversion process to convert a hemicellulose sugar mixture to a solution comprising xylitol, with optional refining of the solution to crystalline or liquid xylitol products.
Figure 5:
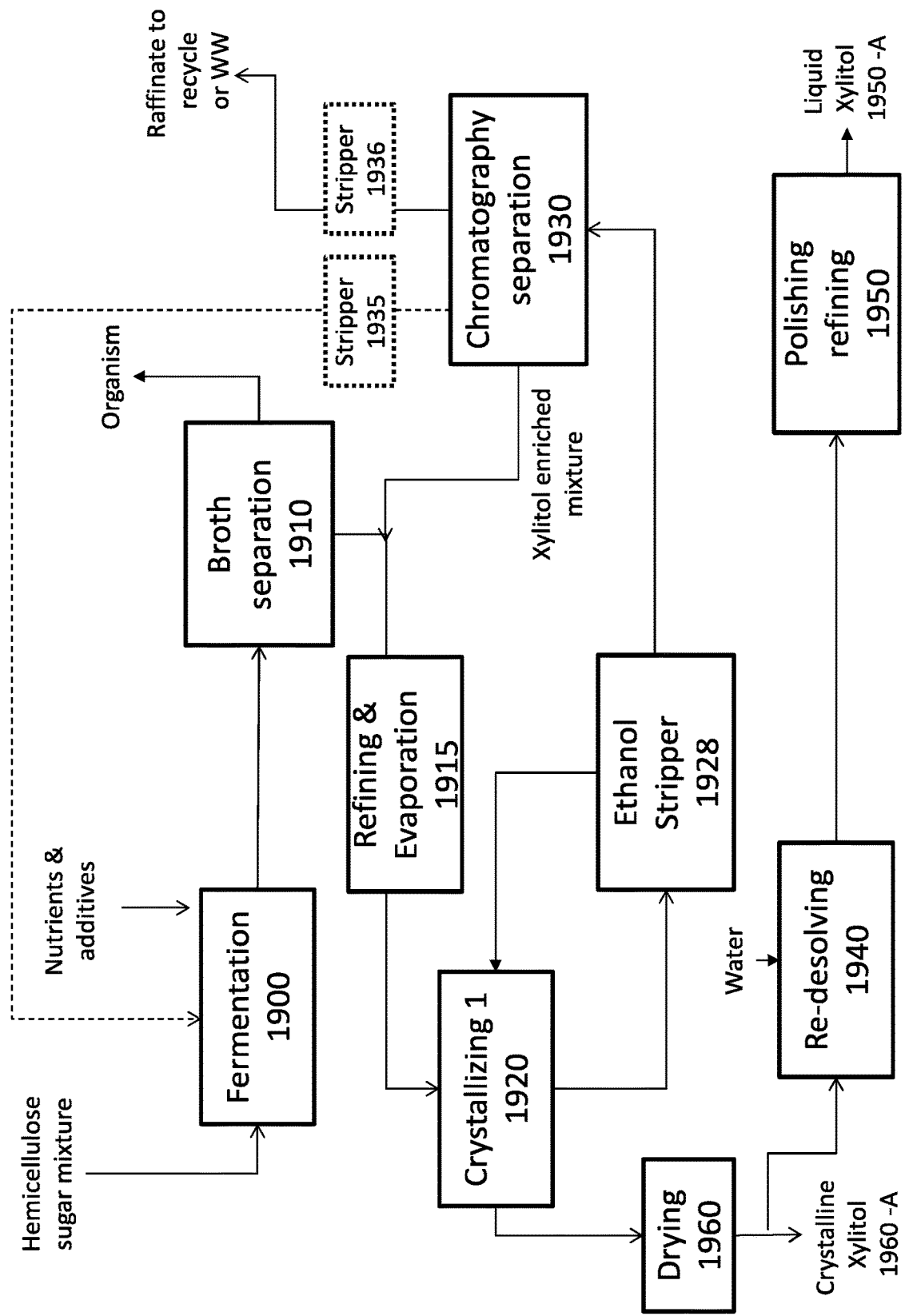
FIG. 5 illustrates a schematic diagram of an exemplary conversion process to convert a hemicellulose sugar mixture to a solution comprising xylitol, with optional refining of xylitol to crystalline or liquid xylitol products.

A fermentation feedstock comprising the refined hemicellulose sugar stream can be utilized by a microorganism for the production of a conversion product. In some examples, the conversion product is a reduced sugar, such as a sugar alcohol. Optionally, the sugar alcohol may be a sugar substitute, such as xylitol. A schematic diagram of an exemplary process to convert a refined hemicellulose sugar stream to xylitol is provided in FIG. 2B. In some examples, a microorganism converts xylose in the refined hemicellulose sugar stream (1710-P1) to xylitol (1950-P1). A method of the present disclosure can comprise fermenting (1900) a fermentation feedstock comprising the refined hemicellulose sugar stream to produce a fermentation broth comprising xylitol. A schematic diagram of an exemplary conversion process to convert a hemicellulose sugar mixture to a solution comprising xylitol, with optional refining of the solution to crystalline (1960-A) or liquid (1950-A) xylitol products, is provided in FIG. 4 and FIG. 5.

The fermentation feedstock may have a very similar composition to the refined hemicellulose sugar stream. Optionally, additives are introduced to the refined hemicellulose sugar stream to generate the fermentation feedstock. Additives may be selected from nutrients, salts, such as NaCl, $MgSO_4$, and $K_2PO_4$, and yeast extract. As such, measured ash levels may be higher in the fermentation feedstock as compared to the refined hemicellulose sugar stream. Optionally, hexoses are added to the refined hemicellulose sugar stream to adjust the xylose:hexose ratio as required for a particular microorganism. In some examples, the concentration of hemicellulose sugars is adjusted in the fermentation feedstock by dilution (e.g., dilution with water) or concentration (e.g., by evaporation).

The fermentation feedstock can comprise at least 40%, at least 45%, at least 50%, at least 55%, at least 60%, at least 65%, at least 70%, at least 75%, at least 80%, at least 90%, or at least 95% weight/weight xylose relative to total dissolved sugars. Optionally, the fermentation feedstock comprises between 40% and 95% weight/weight xylose relative to total dissolved sugars, such as 50% to 90% xylose. In some examples, the fermentation feedstock further comprises at least 5%, at least 10%, at least 12%, at least 15%, at least 17%, at least 20%, at least 22%, at least 25%, at least 27%, at least 30%, at least 32%, at least 35%, at least 37%, at least 40%, at least 42%, at least 45%, at least 50%, at least 52%, at least 55%, or at least 57% weight/weight hexoses relative to total dissolved sugars. Optionally, the fermentation feedstock comprises between 5% and 60% weight/weight hexoses relative to total dissolved sugars, such as 10% to 45% hexoses. In some examples, the fermentation feedstock further comprises less than 15%, less than 14%, less than 13%, less than 12%, less than 11%, less than 10%, less than 9%, less than 8%, less than 7%, less than 6%, less than 5%, less than 4%, less than 3%, or less than 2% weight/weight arabinose relative to total dissolved sugars. Optionally, the fermentation feedstock comprises between 1% and 15% weight/weight arabinose relative to total dissolved sugars, such as 3% to 12% arabinose. In some examples, the fermentation feedstock further comprises less than 15%, less than 10%, less than 9%, less than 8%, less than 7%, less than 6%, less than 5%, less than 4%, less than 3%, less than 2%, or less than 1% weight/weight disaccharides relative to total dissolved sugars. Optionally, the fermentation feedstock comprises between 0.1% and 15% weight/weight disaccharides relative to total dissolved sugars, such as 0.5% to 8% disaccharides. In some examples, the fermentation feedstock further comprises less than 1000 ppm, less than 750 ppm, less than 500 ppm, less than 400 ppm, less than 300 ppm, less than 200 ppm, less than 100 ppm, less than 50 ppm, or less than 10 ppm calcium. Optionally, the fermentation feedstock comprises between 1 ppm and 1000 ppm of calcium, such as 1 ppm to 250 ppm calcium. In some examples, the fermentation feedstock further comprises furfural in an amount up to 1000 ppm, up to 750 ppm, up to 500 ppm, up to 400 ppm, up to 300 ppm, up to 200 ppm, up to 100 ppm, up to 50 ppm, or up to 10 ppm. Optionally, the fermentation feedstock comprises between 1 ppm and 1000 ppm of furfural, such as 1 ppm to 250 ppm furfural. In some examples, the fermentation feedstock further comprises less than 1000 ppm, less than 750 ppm, less than 500 ppm, less than 400 ppm, less than 300 ppm, less than 200 ppm, less than 100 ppm, less than 50 ppm, or less than 10 ppm organic acids, such as acetic acid, levulinic acid, formic acid, and lactic acid. Optionally, the fermentation feedstock comprises between 1 ppm and 1000 ppm organic acids, such as 1 ppm to 1000 ppm acetic acid. Optionally, the fermentation feedstock comprises between 1 ppm and 1000 ppm of formic acid. In some examples, the fermentation feedstock further comprises an amine in an amount up to 1000 ppm, up to 750 ppm, up to 500 ppm, up to 400 ppm, up to 300 ppm, up to 200 ppm, up to 100 ppm, up to 50 ppm, or up to 10 ppm, and wherein the amine comprises at least 12 carbon atoms. Optionally, the amine is a laurylamine, such as monolaurylamine, dilaurylamine, or trilaurylamine. Optionally, the fermentation feedstock comprises between 0.1 ppm and 1000 ppm of an amine comprising at least 12 carbon atoms, such as 0.1 ppm to 250 ppm of an amine comprising at least 12 carbon atoms. In some examples, the fermentation feedstock further comprises a $C_{6-12}$ monoalcohol in an amount up to 1000 ppm, up to 750 ppm, up to 500 ppm, up to 400 ppm, up to 300 ppm, up to 200 ppm, up to 100 ppm, up to 50 ppm, or up to 10 ppm. Optionally, the fermentation feedstock comprises between 1 ppm and 1000 ppm of said $C_{6-12}$ monoalcohol, such as 1 ppm to 250 ppm of said $C_{6-12}$ monoalcohol. In some examples, the fermentation feedstock further comprises nitrogen in an amount up to 1000 ppm, up to 750 ppm, up to 500 ppm, up to 400 ppm, up to 300 ppm, up to 200 ppm, or up to 150 ppm. Optionally, the fermentation feedstock comprises between 1 ppm and 1000 ppm of nitrogen, such as 1 ppm to 250 ppm nitrogen. In some examples, the fermentation feedstock comprises: 50% to 90% weight/weight xylose; 10% to 45% weight/weight hexoses; arabinose in an amount up to 12% weight/weight; disaccharides in an amount up to 8% weight/weight; furfural in an amount up to 1000 ppm; and less than 200 ppm calcium. In some examples, the fermentation feedstock further comprises less than 1000 ppm acetic acid and less than 1000 ppm formic acid. Optionally, the fermentation feedstock further comprises a $C_{6-12}$ monoalcohol in an amount up to 100 ppm.

Various microorganisms have been developed to produce xylitol through a fermentation process. Surprisingly, the refined hemicellulose sugar streams of the present disclosure are particularly well tolerated by many such microorganisms and are efficiently converted to xylitol without the need for further purification, fractionation, separation, or crystallization processes prior to fermentation. Species of microorganisms capable of converting xylose in the refined hemicellulose sugar stream to xylitol include yeasts such as *Pichia, Candida, Hansenula* and *Kluyveromyces*. A strain of *Candida tropicalis* ATCC 13803 can be used for converting xylose to xylitol using glucose in the refined hemicellulose sugar stream for cell growth (see e.g. U.S. Pat. Nos. 5,998, 181 and 5,686,277). Xylitol can be produced by *Candida guilliermondii* FTI 20037 (see e.g. Mussatto and Roberto (2003) J. Appl. Microbiol. 95:331-337). *Saccharomyces cerevisiae* can be used to produce xylitol (see e.g. U.S. Pat. No. 5,866,382). A variety of fermentation systems are able to convert a refined hemicellulose sugar stream to a high xylitol, low arabitol product, through the use of various strains of *E. Coli* (see e.g. PCT/US2011/021277, PCT/US2011/044696, and US Pub. No. 2013/0217070). These systems can utilize C6 sugars and some of the arabinose of a refined hemicellulose sugar stream as an energy source for proliferation and metabolism, while converting predominantly xylose to xylitol with minimal co-conversion of arabinose to arabitol. Optionally, the microorganism is a microorganism described in US Pub. No. 2013/0217070, such as HZ 1434, ZUC220, ZUC170, ZUC136, HZ 2061, or HZ 2062. A two-substrate fermentation with *C. tropicalis* and *Candida Parapsilosis* using glucose for cell growth and xylose for xylitol production can be used (see e.g. U.S. Pat. Nos. 5,998,181 and 5,686,277). Xylitol can be produced as a co-product during fermentative ethanol production by a single yeast strain, utilizing hydrolyzed lignocellulose-containing material (see e.g. US2003/0235881). Xylonic acid can be produced from xylose with a recombinant fungal strain that is genetically modified to express a xylose dehydrogenase gene, which is able to convert xylose to xylonolactone, coupled with xylitol production when the fungal host is selected from the genera *Saccharomyces, Kluyveromyces, Candida* and *Aspergillus* (see e.g. WO 2010/106230). While other genetically engineered organisms have been described to ferment xylose or a sugar mixture to produce xylitol, many show insufficient productivity to be viably commercialized. In some examples, the refined hemicellulose sugar stream (e.g., the fermentation feedstock) is fed into a fermentation unit seeded with the selected species at 10-40% DS, such as 14-28% DS. In some examples, the microorganism selectively reduces xylose to xylitol, without production of other polyols resulting from monosaccharides other than xylose in the fermentation broth.

The refined hemicellulose sugar stream can be added to a fermentation unit containing fermentation media. The fermentation media may comprise nutrients, including, for example, tryptone, yeast extract, potassium phosphate, sodium chloride, and magnesium sulfate. The fermentation unit can be inoculated with a culture of a suitable microorganism, optionally to a final concentration of 10-40% DS. In some examples, the temperature of the fermentation unit is maintained at a suitable temperature for the microorganism, such as 25 to 35° C. Optionally, the pH of the fermentation solution is maintained at pH 6.0 to pH 8.0, such as about pH 7.0. The pH can be adjusted using $NH_4OH$. Optionally, the fermentation solution is agitated, such as by introduction of air. In some examples, additional refined hemicellulose sugar stream is added. In some examples, hexoses, such as glucose, are added to the fermentation solution. Additional refined hemicellulose sugar stream may be added 6 hours, 8 hours, 10 hours, 12 hours, 16 hours, 20 hours, 24 hour, 36 hours, or 48 hours after addition of the microorganism to the fermentation unit. The fermentation process may be allowed to run for at least 12 hours, at least 18 hours, at least 24 hours, at least 36 hours, at least 48 hours, at least 60 hours, at least 72 hours, at least 80 hours, at least 84 hours, at least 96 hours, or at least 108 hours before recovering xylitol from the fermentation broth.

A microorganism described herein can convert the fermentation feedstock into a fermentation broth comprising xylitol. The fermentation broth can comprise at least 50 g/L, at least 60 g/L, at least 70 g/L, at least 80 g/L, at least 90 g/L, at least 100 g/L, at least 110 g/L, at least 120 g/L, at least 130 g/L, or at least 140 g/L xylitol. Optionally, the fermentation broth comprises between 50 and 140 g/L xylitol, such as 60 to 100 g/L, 70 to 100 g/L, 80 to 100 g/L, or 70 to 90 g/L xylitol. In some examples, the microorganism produces little to no ethanol. Optionally, the fermentation broth comprises less than 15 g/L, less than 12 g/L, less than 10 g/L, less than 9 g/L, less than 8 g/L, less than 7 g/L, less than 6 g/L, less than 5 g/L, less than 4 g/L, less than 3 g/L, less than 2 g/L, or less than 1 g/L ethanol. In some examples, the fermentation broth comprises xylose in an amount less than 50 g/L, less than 40 g/L, less than 30 g/L, less than 20 g/L, less than 10 g/L, less than 8 g/L, less than 6 g/L, less than 4 g/L, less than 3 g/L, less than 2 g/L, less than 1 g/L, less than 0.5 g/L, or less than 0.2 g/L. Optionally, the fermentation broth comprises glucose in an amount less than 35 g/L, less than 25 g/L, less than 15 g/L, less than 10 g/L, less than 8 g/L, less than 6 g/L, less than 4 g/L, less than 3 g/L, less than 2 g/L, less than 1 g/L, less than 0.5 g/L, or less than 0.2 g/L. In some examples, the fermentation broth comprises furfural in an amount up to 1000 ppm, up to 750 ppm, up to 500 ppm, up to 400 ppm, up to 300 ppm, up to 200 ppm, up to 100 ppm, up to 50 ppm, or up to 10 ppm. Optionally, the fermentation broth comprises between 1 ppm and 1000 ppm of furfural, such as 1 ppm to 250 ppm furfural. In some examples, the fermentation broth comprises less than 1000 ppm, less than 750 ppm, less than 500 ppm, less than 400 ppm, less than 300 ppm, less than 200 ppm, less than 100 ppm, less than 50 ppm, or less than 10 ppm calcium. Optionally, the fermentation broth comprises between 1 ppm and 1000 ppm of calcium, such as 1 ppm to 250 ppm calcium. In some examples, the fermentation broth comprises less than 1000 ppm, less than 750 ppm, less than 500 ppm, less than 400 ppm, less than 300 ppm, less than 200 ppm, less than 100 ppm, less than 50 ppm, or less than 10 ppm organic acids, such as acetic acid, levulinic acid, formic acid, and lactic acid. Optionally, the fermentation broth comprises between 1 ppm and 1000 ppm organic acids, such as 1 ppm to 1000 ppm acetic acid. Optionally, the fermentation broth comprises between 1 ppm and 1000 ppm of formic acid. In some examples, the fermentation broth comprises a $C_{6-12}$ monoalcohol in an amount up to 1000 ppm, up to 750 ppm, up to 500 ppm, up to 400 ppm, up to 300 ppm, up to 200 ppm, up to 100 ppm, up to 50 ppm, or up to 10 ppm. Optionally, the fermentation broth comprises between 1 ppm and 1000 ppm of said $C_{6-12}$ monoalcohol, such as 1 ppm to 250 ppm of said $C_{6-12}$ monoalcohol. In some examples, the fermentation broth comprises: at least 60 g/L xylitol; less than 50 g/L xylose; less than 10 g/L ethanol; less than 50 g/L hexoses; furfural in an amount up to 1000 ppm; and less than 200 ppm calcium. In some examples, the fermentation broth further comprises less than 1000 ppm acetic acid and less than 1000 ppm formic acid. Optionally, the fermentation broth further comprises a $C_{6-12}$ monoalcohol in an amount up to 100 ppm. Optionally, the fermentation broth comprises less than 100 ppm galactitol, such as less than 50 ppm, less than 10 ppm, less than 1 ppm, or less than 1 ppb galactitol. In some examples, galactitol is not detected in the fermentation broth. In some examples, the fermentation broth comprises a microorganism described herein. Optionally, the microorganism is selected from naturally occurring bacteria, recombinant bacteria, naturally occurring yeast, recombinant yeast, and fungi. The microorganism may be an *E. coli* strain, such as such as HZ 1434, ZUC220, ZUC170, ZUC136, HZ 2061, or HZ 2062.

Optionally, the yield of xylitol in the fermentation broth is more than 90%, more than 91%, more than 92%, more than 93%, more than 94%, more than 95%, more than 96%, more than 97%, or more than 98% of relative to the amount of xylose in the refined hemicellulose sugar stream. In some examples, at least 70%, at least 75%, at least 80%, at least 85%, at least 90%, at least 91%, at least 92%, at least 93%, at least 94%, at least 95%, at least 96%, at least 97%, or at least 98% of xylose in the lignocellulose containing biomass is converted to xylitol. Optionally, the amount of arabitol in the fermentation broth is less than 10% of the total polyols. Optionally, the amount of hexoses is reduced to less than 10%, less than 9%, less than 8%, less than 7%, less than 6%, less than 5%, less than 4%, less than 3%, less than 2%, or less than 1% of the concentration of hexoses in the fermentation feedstock or refined hemicellulose sugar stream. Optionally, the fermenting produces xylitol at a rate of at least 1 g/L/h, at least 2 g/L/h, at least 3 g/L/h, at least 4 g/L/h, at least 5 g/L/h, at least 6 g/L/h, at least 7 g/L/h, or at least 8 g/L/h. In some examples, the fermenting produces—in less than 120 h, less than 110 h, less than 100 h, less than 90 h, less than 80 h, less than 70 h, less than 60 h, less than 50 h, less than 40 h, less than 30 h, less than 20 h, less than 15 h, or less than 10 h-at least 50 g/L, at least 60 g/L, at least 70 g/L, at least 80 g/L, at least 90 g/L, at least 100 g/L, at least 110 g/L, at least 120 g/L, at least 130 g/L, or at least 140 g/L xylitol (per liter of fermentation broth). Optionally, the fermenting produces at least 60 g/L xylitol in less than 80 hours of fermenting, such as 70 g/L xylitol in less than 80 hours. Optionally, the fermenting produces at least 100 g/L xylitol in less than 80 hours of fermenting.

Xylitol can be recovered from the fermentation broth by any suitable method (1910), such as filtration, crystallization, or chromatographic separation, or a combination thereof. The fermentation broth can be filtered or centrifuged to remove the microorganism. In some examples, filtration comprises three steps, including microfiltration, ultrafiltration, and nanofiltration. The fermentation broth may be subjected to microfiltration, optionally followed by ultrafiltration, optionally followed by nanofiltration. The filtration can remove the microorganism from the fermentation broth. The nanofiltration can remove residual disaccharides and oligosaccharides from the fermentation broth. In some examples, the filtration removes at least 10%, at least 20%, at least 30%, at least 40%, at least 50%, at least 60%, at least 70%, at least 80%, at least 90%, at least 95%, or at least 98% weight/weight oligosaccharides having a degree of polymerization of three (DP3) or more from the fermentation broth. In some examples, the filtration removes at least 10%, at least 20%, at least 30%, at least 40%, at least 50%, at least 60%, at least 70%, at least 80%, at least 90%, at least 95%, or at least 98% weight/weight disaccharides (DP2) from the fermentation broth. The filtered solution can be contacted with at least one of the following: activated carbon, such as granulated active carbon (GAC); and ion exchange resin, such as strongly acidic cation (SAC) resin, weakly basic anion (WBA) resins, and mixed bed (MB) resins. The filtered and optionally refined solution can be concentrated by evaporation (1915) to increase the concentration of dissolved solids to at least 50%, at least 60%, at least 70%, or at least 80% weight/weight dissolved solids, such as about 80% weight/weight dissolved solids. In some examples, the concentration of the solution is about 70% to about 90% weight/weight dissolved solids, such as 75% to 85% weight/weight.

The solution can be introduced batch-wise or continuously into a xylitol crystallization unit (1920). Optionally, ethanol is added to a specified concentration, such as 0-40% weight/weight ethanol. Optionally, the solution is seeded with xylitol crystals and cooled gradually at a controlled rate under agitation to induce crystallization. Xylitol crystals can be collected by filtration or centrifugation. Optionally, the collected xylitol crystals are washed and dried (1960). Optionally, the collected xylitol crystals are re-dissolved (1940) to form a xylitol solution. The xylitol solution may be further polished (1950) and the polished solution used as liquid xylitol product (1950-A). Polishing may include contacting the xylitol solution with an ion exchange resin, such as SAC, WBA, and MB resins. Optionally, polishing includes contacting the xylitol solution with granulated active carbon.

The mother liquor of the xylitol crystallization can be concentrated by evaporation (1922) to at least 70% weight/weight dissolved solids, such as 80% to 88% weight/weight dissolved solids. Optionally, the mother liquor is stripped by evaporation to remove ethanol, if present (1928). The concentrated mother liquor can be introduced into a second xylitol crystallization unit (1925) and can optionally be seeded with xylitol crystals. Gradual cooling at a controlled rate may result in a second crystallization of xylitol. These crystals (1925-A) can be collected by filtration or centrifugation. The second crystallization may yield crystals of lower purity than the first crystallization. In some examples, the mother liquor of the second crystallization is separated by chromatography (1930) to yield an extract stream comprising a composition similar to the first mother liquor, a raffinate stream which is low in xylitol and rich in arabitol, and a third stream comprising residual reducing sugars and residual oligomers. The extract stream can be recycled into the second crystallization unit to increase overall xylitol yield. Optionally, the extract stream is stripped by evaporation to remove ethanol, if present. Optionally, the third stream comprising residual reducing sugars is recycled to fermentation. Optionally, the third stream is stripped by evaporation to remove ethanol, if present (1935). Optionally, the raffinate stream comprising arabitol is fed into an anaerobic digester to convert the organic matter to methane that can be used as an energy source. Optionally, the raffinate stream is stripped by evaporation to remove ethanol, if present (1936).

In some examples, recovering xylitol from the fermentation broth comprises: (i) filtering the fermentation broth through a microfilter and collecting the resulting microfiltrate; (ii) filtering the microfiltrate through an ultrafilter and collecting the resulting ultrafiltrate; (iii) filtering the ultrafiltrate through a nanofilter and collecting the resulting nanofiltrate; (iv) contacting the nanofiltrate with an ion exchange resin, thereby producing a refined nanofiltrate; (v) concentrating the refined nanofiltrate by evaporation, thereby producing a concentrated nanofiltrate; (vi) crystallizing xylitol from the concentrated nanofiltrate; and (vii) separating xylitol crystals from the mother liquor. Optionally, recovering xylitol from the fermentation broth further comprises: (viii) dissolving the xylitol crystals to form a xylitol solution; and (ix) polishing the xylitol solution with an ion exchange resin.

Recovered xylitol product can comprise at least 95% weight/weight xylitol, such as at least 96%, at least 97%, at least 98%, at least 99%, at least 99.5%, or at least 99.9% weight/weight xylitol. The xylitol product can be produced by a method described herein. Optionally, the xylitol product comprises less than 1% weight/weight oligosaccharides, such as less than 0.5%, less than 0.25%, less than 0.1%, less than 0.05%, or less than 0.01% weight/weight oligosaccharides. Optionally, the xylitol product comprises hexoses in an amount up to 1% weight/weight, such as up to 0.5%, up to 0.25%, up to 0.1%, up to 0.05%, or up to 0.01% weight/weight hexoses. The hexoses may be selected from glucose, galactose, mannose, and fructose. Optionally, the xylitol product comprises less than 100 ppm arabitol, such as less than 50 ppm, 10 ppm, 1 ppm, or 1 ppb arabitol. Optionally, the xylitol product comprises less than 100 ppm galactitol, such as less than 50 ppm, 10 ppm, 1 ppm, or 1 ppb galactitol. In some examples, galactitol is not detected in the xylitol product. Optionally, the xylitol product comprises ash in an amount up to 0.25% weight/weight, such as up to 0.1%, up to 0.05%, or up to 0.01% weight/weight ash. Optionally, the xylitol product comprises furfural in an amount up to 500 ppm, such as up to 250 ppm, 100 ppm, 50 ppm, 10 ppm, or 1 ppm furfural. Optionally, the xylitol product comprises an amine in an amount up to 500 ppm, such as up to 250 ppm, 100 ppm, 50 ppm, 10 ppm, or 1 ppm amine, and wherein the amine comprises at least 12 carbon atoms. Optionally, the xylitol product comprises a $C_{6-12}$ monoalcohol in an amount up to 500 ppm, such as up to 250 ppm, 100 ppm, 50 ppm, 10 ppm, or 1 ppm $C_{6-12}$ monoalcohol. In some examples, the xylitol product is provided in crystalline form. In some examples, the xylitol product is provided as an aqueous solution. Optionally, the concentration of the aqueous solution is at least 50% weight/weight dissolved solids, for example, about 70% to about 90% weight/weight dissolved solids, such as 75% to 85% weight/weight.

The overall recovery yield of xylitol by a xylitol separation of the subject methods can be more than 70%, more than 75%, more than 80%, more than 85%, more than 86%, more than 87%, more than 88%, more than 89%, more than 90%, more than 91%, more than 92%, more than 93%, more than 94%, more than 95%, more than 96%, more than 97%, or more than 98% xylitol. In some examples, the yield of xylitol recovered by the subject methods is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, or at least 98% xylitol relative to the xylose content of the lignocellulose containing biomass.

Xylitol can be separated from a sugar mixture solution by simulated moving bed (SMB) ion exclusion chromatography using anion exchange resin (see e.g. U.S. Pat. No. 6,451,123). An improved system and method for the fractionation of xylitol by an industrial scale sequential simulated moving bed (SSMB) chromatography can be used (see e.g. U.S. application Ser. No. 14/398,444). Alternatively, a SAC resin can be used for the separation of xylitol from a polyol mixture (see e.g. U.S. Pat. No. 4,008,285), wherein the salt of the resin is selected from the group consisting of alkaline earth metal salts (e.g. $Sr^{2+}$ salts, $Ca^{2+}$ salts), $Fe^{3+}$ salts and $Al^{3+}$ salts. In some examples, a similar SSMB method is applied to yield a xylitol enriched stream, an arabitol stream and a reducing sugar stream comprising monomers and oligomers. The xylitol enriched stream is recycled to the crystallizer feed, such that yield of xylitol is maximized. The reducing sugar stream is optionally stripped of residual ethanol, if present, and recycled to the fermentation unit. The arabitol stream is stripped of residual ethanol, if present, and is fed to a waste treatment process comprising an anaerobic digester to produce methane that can be used as an energy source for the process.

A chromatographic fractionation to achieve enrichment of xylitol concentration can be carried out with ion exchange resins (e.g., a cation exchange resin and an anion exchange resin) as the column packing material. Cation exchange resins include strong acid cation exchange resins and weak acid cation exchange resins. The strong acid cation exchange resins can be in a monovalent or multivalent metal cation form, e.g., in $H^+$, $Mg^{2+}$, $Ca^{2+}$, $Sr^{2+}$ or $Zn^{2+}$ form. The strong acid cation exchange resins typically have a styrene skeleton, which is preferably cross-linked with 3 to 8%, preferably 5 to 6.5% of divinylbenzene. The weak acid cation exchange resins may be in a monovalent or multivalent metal cation form, e.g., $H^+$, $Mg^{2+}$, $Ca^{2+}$, $Sr^{2+}$ form, or $Na^+$ form. Suitable resins can be purchased from Lanxess AG, Purolite, Dow Chemicals Ltd. or Rohm & Haas.

A chromatographic fractionation can be carried out in a batch mode, a simulated moving bed (SMB) mode, or a sequential simulated moving bed (SSMB) mode. The temperature of the chromatographic fractionation is typically in the range of 20 to 90° C., such as 40 to 65° C. The pH of the solution to be fractionated can be acidic or adjusted to a range of pH 2.5 to 7, preferably 3.5 to 6.5, and most preferably 4 to 5.5. The fractionation can be carried out with a linear flow rate of about 1 m/h to about 10 m/h in the separation column.

Figure 7:
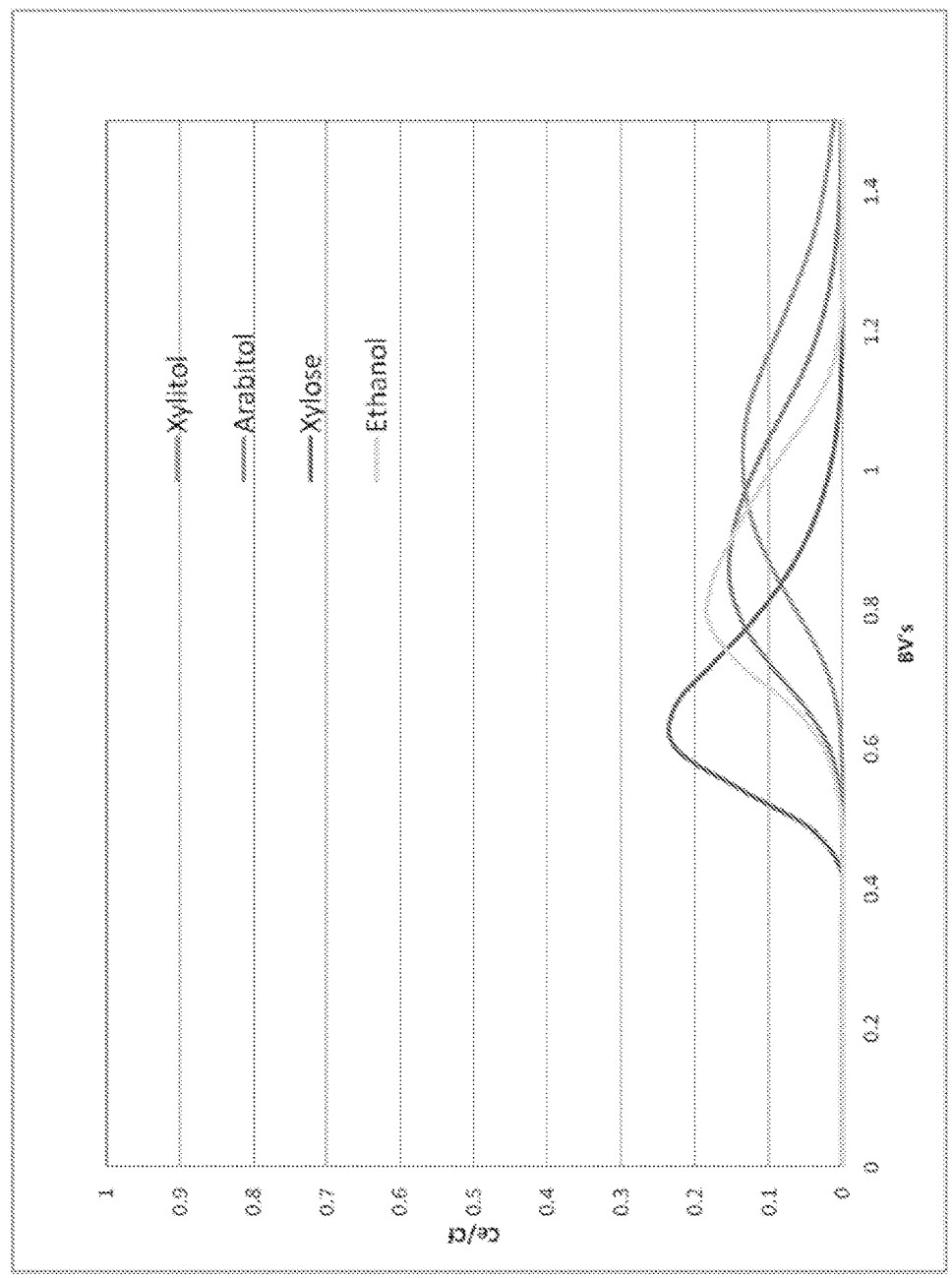
FIG. 7 illustrates results of a pulse test chromatogram showing fractionation of a mother liquor after xylitol crystallization to obtain xylitol enriched and xylitol removed sugar mixtures.

FIG. 7 presents a pulse test showing separation of xylitol from an aqueous mixture comprising xylitol, arabitol, xylose and ethanol, indicating the ability to fractionate xylitol by SSMB. The resin is a SAC resin in the $Sr^{2+}$ form.

A biomass embodied in a subject method or system disclosed herein may be sugarcane bagasse. In some examples, the biomass may comprise sugarcane leaves. While it may be desirable to return some mass of sugarcane leaves back to the soil after harvest, excess mass of sugarcane leaves may be problematic. Many skilled in the art currently consider sugarcane leaves to be waste that needs to be treated, often in environmentally unfriendly solutions such as burning. Sugarcane leaves that enter the sugar mill can reduce production capacity and increase sucrose losses to the exiting fiber (i.e., bagasse). It can be therefore advantageous to the sugarcane growers and/or the sugar mill to use leaves as a source of hemicellulosic sugars. Currently, some of the leaves can be processed through the sugar mill. Since sucrose content in the leaves is low, they effectively reduce the productivity of the sugar mill. In some examples, leaves are separated from the harvested canes by air classification to separate the light leaves from the heavy cane. In some examples, the leaves are collected in the field, baled and then transferred directly to the wash unit for processing. Sugarcane leaves may be processed similarly to sugarcane bagasse or blended with bagasse for processing.

If a high xylose feedstock other than sugarcane bagasse or leaves is used, e.g. birch or *eucalyptus*, the wash step may be unnecessary and the system adapted accordingly by replacing the wash unit with a debarking and sizing system. The hemicellulose extraction units and methods disclosed herein are particularly suitable for recovering hemicellulose sugars comprising xylose from pre-hydrolysates produced at dissolving pulp mills in the production of cellulosic fibers, e.g. viscose and acetate. Pre-hydrolysis is applied at dissolving pulp mills to remove hemicellulose from the biomass prior to a Kraft or sulfite pulping. Dissolving pulps typically contain low levels of residual hemicellulose (e.g., up to 3%, up to 2% or up to 1% weight/weight hemicellulose), compared to higher levels in typical paper grade Kraft pulp, typically about 10%. Typically, pre-hydrolysis is conducted in diffusing pulp digesters by treating the wood chips with steam or water to induce autohydrolysis. Steam hydrolysis can result in the hydrolysate being held by the wood pores. Hydrolysis in water can allow for collection of the formed hydrolysate in higher yields. Optionally, an acid may be added to the water to accelerate hemicellulose hydrolysis. Optionally, the acid may be a mineral acid or an organic acid, e.g. $SO_2$, $H_2SO_4$, HCl, acetic acid, or formic acid. Since pre-hydrolysis conditions can be fairly severe to optimally remove hemicellulose from the biomass, the resulting hydrolysate can be relatively high in degradation products. Nonetheless, the hydrolysate can be refined and xylose and/or xylitol can be harvested in the systems and methods disclosed herein, thus valorizing the hydrolysate stream and contributing significantly to the economics of the mill. Optionally, the system disclosed herein can be combined with the dissolving pulp mill for recovery of chemicals, solvent recycling, and harvesting of energy from waste streams, thus reducing production cost of both the hemicellulose sugars and the dissolving pulp. Optionally, hexoses are added to the hydrolysate prior to fermentation to achieve the preferred ratios of xylose to hexoses as described above for the refined hemicellulose sugar stream and the fermentation feedstock.

In one aspect, the disclosure provides a system for producing xylitol from a lignocellulose-containing biomass. In one example, the system comprises: (i) a hemicellulose extraction unit configured to extract and hydrolyze hemicellulose from the biomass to produce a hemicellulose sugar stream and a lignocellulose remainder stream; (ii) a refining unit in fluid communication with the extraction unit, wherein the refining unit is configured to receive the hemicellulose sugar stream and an amine extractant, and wherein the amine extractant removes impurities from the hemicellulose sugar stream to produce a refined hemicellulose sugar stream; optionally, (iii) a sensing unit configured to analyze one or more parameters of the refined hemicellulose sugar stream, wherein the one or more parameters are selected from pH, light absorbance, conductivity, density, xylose concentration, and hexose concentration; (iv) a fermentation unit in fluid communication with the refining unit to receive the refined hemicellulose sugar stream, wherein the fermentation unit is configured to contain the refined stream and a microorganism, and wherein the microorganism facilitates production of the xylitol from a monosaccharide in the refined stream to produce a fermentation broth; and (v) a xylitol refining unit, wherein the xylitol refining unit is configured to remove the xylitol from the fermentation broth.

Figure 8:
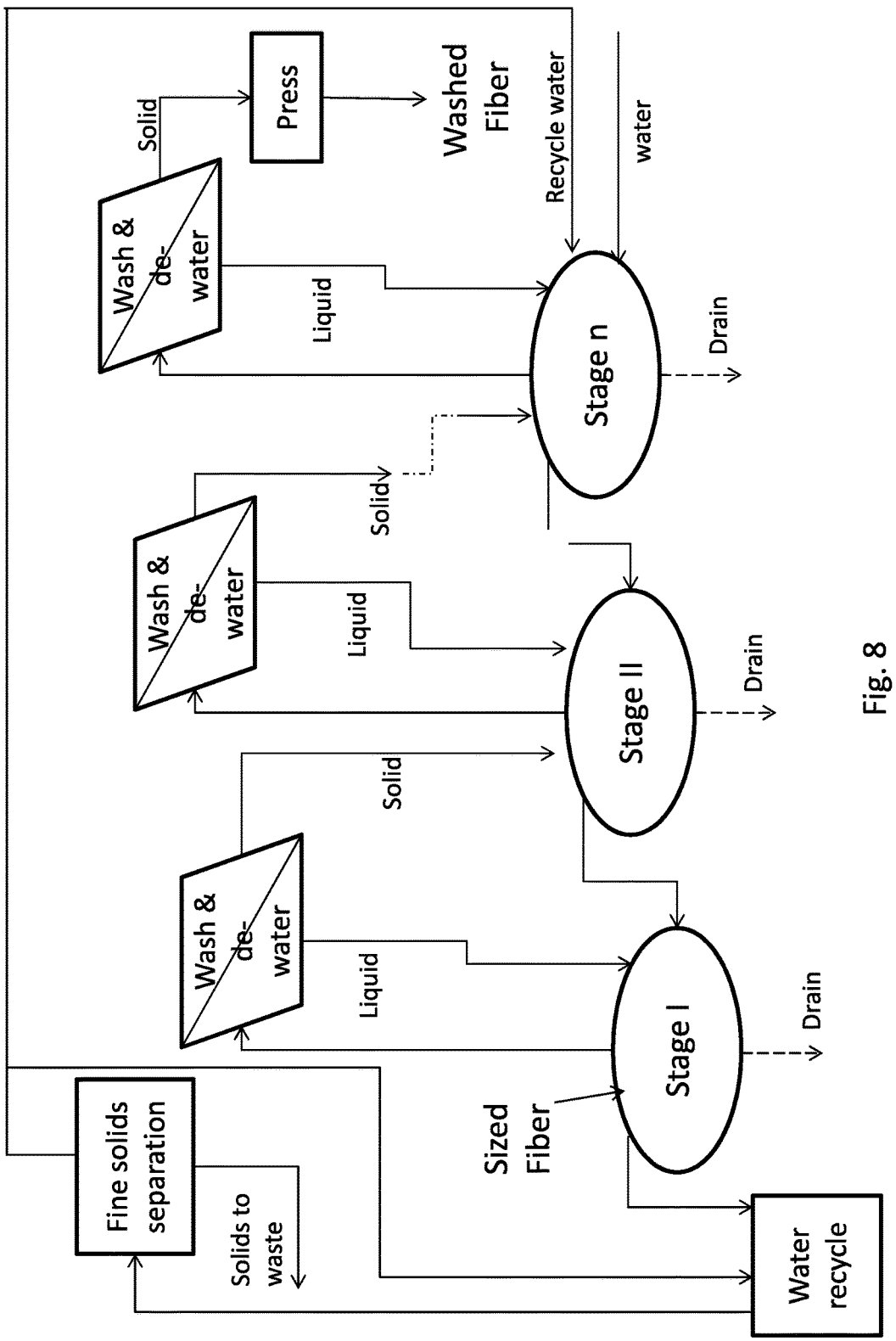
FIG. 8 illustrates a schematic diagram of exemplary sequential processes for washing biomass.

Optionally, the system further comprises a wash unit configured to remove ash and soil from the biomass. The wash unit can be in fluid communication with the hemicellulose extraction unit. Optionally, a counter current wash unit as depicted in FIG. 8 is used to de-soil and de-ash the biomass. A method for reducing ash and soil content may comprise at least one and up to n stages of re-slurry and milling (e.g., grinding) the biomass, and at least one and up to m stages of washing and dewatering the biomass, wherein n is 2, 3, 4, 5, 6, 7, 8, 9 or 10 and m is 2, 3, 4, 5, 6, 7, 8, 9 or 10. Optionally, n is equal to m. In some examples, m is greater than n or n is greater than m.

Each stage of a wash unit used to reduce soil and ash content of a biomass may comprise a tank, wherein the biomass is re-slurried by means of a stirrer, a pump or any other means capable of causing re-slurry of the biomass in water. Optionally, the ratio of liquid to solid in the tank is 30-60:1, such as a liquid to solid ratio of 60 to 1, 55 to 1, 50 to 1, 45 to 1, 40 to 1, 35 to 1, or 30 to 1. Each tank may be equipped with a solids inlet. The tank may be in fluid communication, e.g. via a pump and a pipe, with a dewatering device, wherein the slurry in the tank can be transferred to the dewatering device. The wash unit may comprise a pipe to return the liquid phase from the dewatering device to the tank. Optionally, the dewatering device is positioned higher than the tank so that gravity can assist return of the liquid to the tank. In some examples, each tank is equipped with a liquid inlet connected to receive liquid from its n+1 stage, and a liquid outlet connected to deliver liquid to its n−1 stage, where the liquid outlet of stage I can be connected to deliver liquid to an auxiliary tank for water recycling. The position of the liquid outlet can be at the top of the liquid phase in the tank of each stage, such that liquid is transferred as an overflow stream. Optionally, the tank of stage n comprises an additional water inlet connected to receive a water stream. Optionally, the water stream comprises recycled filtered or treated water from the wash unit, fresh water, or process water from other units of the system.

An auxiliary tank of the wash unit may receive a purge stream. The purge stream may come from the sequential overflow or from the bottom purge of the tanks, in a continuous or intermittent mode. Optionally, the auxiliary tank is connected to at least one device for the separation of fine particles from the liquid, such as a hydrocyclone, a centrifuge, or a filter. A hydrocylone or a centrifuge may be used to recover fine biomass particles from the top outlet. This recovered biomass can be sent to the tank of stage n to minimize biomass losses. Ash and soil particles can be separated from the bottom outlet or the higher density outlet (however positioned in the separation device used). This stream can be further filtered to remove soil and recover the water.

The tank of each stage may also be equipped with a low level liquid/solid outlet, preferably positioned at the bottom of the tank. Optionally, the system is also equipped with at least one inlet of pressurized air. One or more stages may be equipped with a grinding or milling device, wherein such device is optionally an inline or submerged grinding or milling device. In some examples, the grinding or milling is increasingly finer with each progressive stage n in the wash unit. Various vendors offer suitable grinding, milling, homogenizing and pulping devices, including, for example, EBERA Fluid Handling, Bolton Emerson, ARDE-BARINKO and IKA. Different devices may be used at different stages.

Optionally, at least one dewatering device comprises a screen. The screen size may vary between 1000 and 100 micrometers. Optionally, the size of the screen is decreased with each progressive stage m in the wash unit. The screen can be held in a diagonal position or a bent position with respect to earth. Biomass can be collected from the top of the screen and transferred through a solid transfer chute to the tank of stage n+1. A liquid comprising soil particles and fine particles of biomass may go through the screen and can be returned to the tank of stage n. Various vendors offer suitable screening devices, including, for example, Dorr-Oliver and FluidQuip. Different devices may be used at different stages.

In some examples, a dewatering device may be connected to another dewatering device directly (i.e. not through another tank). Optionally, the final dewatering device m applies pressure to reduce water content to a minimum. In some examples, the final water content of the washed biomass may be less than 70, less than 65, less than 60, less than 55, less than 50, less than 45, less than 40, less than 35, or less than 30% wt/wt. In some examples, the final water content of the washed biomass is 40-60% wt/wt. The final dewatering device may comprise a screw press. A suitable screw press can comprise either a single or double screw or a twin screw or roller mill that achieves the final water content at the desired production rate. Various vendors offer suitable screw press devices, including, for example, Vincent Corporation, Stord Bartz, FKC Company Ltd and Parkson Corporation. Different devices may be used at different stages.

Raw biomass can be received by the wash unit from harvest or upstream treatment in chips, lumps, or particles of various sizes. Optionally, the raw biomass is first crushed or shredded to break up lumps and to size the raw biomass to uniform size that can be re-slurried and handled by pumps and mills further downstream. Suitable systems for crushing or shredding may be selected from, but are not limited to, a jaw crusher, a cone crusher, a tub grinder, a hammer mill, and a chipper. Numerous vendors offer such equipment, including, for example, West Salem Machinery, Metso Corporation and Andritz. Optionally, the raw biomass is sized such that greater than 70, 75, 80, 81, 82, 83, 84, 85, 86, 87, 88, 89, 90, 91, 92, 93, 94, 95, 96, 97, 98, or greater than 99% weight/weight goes through a mesh 20 sieve (841 micrometer). Optionally, the raw biomass is sized such that greater than 70, 75, 80, 81, 82, 83, 84, 85, 86, 87, 88, 89, 90, 91, 92, 93, 94, 95, 96, 97, 98, or greater than 99% weight/weight goes through a mesh 12 sieve (1680 micrometer). Optionally, the raw biomass is sized such that greater than 70, 75, 80, 81, 82, 83, 84, 85, 86, 87, 88, 89, 90, 91, 92, 93, 94, 95, 96, 97, 98, or greater than 99% weight/weight goes through a mesh 7 sieve (2830 micrometer). Optionally, the raw biomass is sized such that greater than 70, 75, 80, 81, 82, 83, 84, 85, 86, 87, 88, 89, 90, 91, 92, 93, 94, 95, 96, 97, 98, or greater than 99% weight/weight goes through a mesh 5 sieve (4000 micrometer). In some examples, greater than 93% wt/wt goes through a mesh 12 sieve and greater than 90% wt/wt goes through a mesh 20 sieve. In some examples, about 20% (wt/wt) of the material is retained on a mesh 60 sieve (250 micrometer) and about 20% (wt/wt) is retained on a mesh 40 sieve (400 micrometer). In some examples, less than 4%, less than 5%, less than 6%, less than 7%, less than 8%, less than 9%, less than 10%, less than 11%, or less than 12% weight/weight goes through a mesh 200 sieve (74 micrometer). The sized raw biomass can be transferred by any means of transferring solid material and can be fed to the tank of stage I of the wash unit.

A system described herein may comprise a hemicellulose extraction unit configured to extract and hydrolyze hemicellulose from biomass to produce a hemicellulose sugar stream and a lignocellulose remainder stream. A hemicellulose extraction unit may comprise a tank equipped with a solid feed device and at least one aqueous feed device, wherein the tank can hold pressure of at least 400 psi and can be heated to temperature of at least 250° C. The tank can be equipped with stirring capability to mix solid and liquid streams. Optionally, the tank is equipped with flow capability to move solid and liquid streams. The tank can be equipped with an outlet suitable for removing the reacted slurry. A tank of the extraction unit can optionally have more than one compartment wherein adjacent compartments are separated by weirs. Optionally, the extraction unit may comprise more than one tank, wherein the tanks are in fluid communication with adjacent tanks to allow for mass flow through consecutive tanks. In some examples, the extraction unit comprises a plug flow reactor. The plug flow reactor may be mounted at a low angle to assist in reactor emptying when a shutdown is required. The reactor can be partially or fully jacketed to prevent heat loss.

An aqueous slurry comprising the biomass may be fed continuously to the hemicellulose extraction unit. In some examples, acid concentration of the aqueous slurry is monitored. Optionally, additional acid is added if the acid concentration is below a threshold. Optionally, said monitoring is continuous and said acid addition is controlled by a computerized system that accepts input from at least one probe, wherein the computerized system further controls pumps and valves of the system. Optionally, the extraction product, e.g., a hemicellulose extraction slurry comprising hemicellulose sugars, is removed continuously. In some examples, the aqueous slurry fed to the extraction unit can be heated in the incoming stream. Optionally, the slurry is heated in a tank of the extraction unit. In some examples, a stream exiting the extraction unit (e.g., a hemicellulose extraction slurry) is cooled. Heating or cooling processes may be fast, e.g., flash heating and/or flash cooling. Optionally, heating to the extraction set point is done in less than 60, less than 45, less than 30, less than 25, less than 20, less than 15, less than 10, or less than 5 minutes. Optionally, cooling of the extraction slurry is done in less than 60, less than 45, less than 30, less than 25, less than 20, less than 15, less than 10, or less than 5 minutes. Heat removed at the cooling end can be used to heat the heating end by the use of suitable heat exchangers, e.g. spiral type shell and tube, standard shell and tube or a plate and frame. Suitable heat exchangers can be obtained, for example, from Alfa Laval or Chemineer Inc. In some examples, the extraction unit is used to conduct a batch or preferably a continuous process to extract hemicellulose, organic acids and remaining ash and extractives from biomass.

In some examples, the hemicellulose extraction slurry comprises hemicellulose sugars and lignocellulose remainder. The hemicellulose extraction unit may comprise a system for separating a lignocellulose remainder stream from the hemicellulose sugar stream. Optionally, the lignocellulose remainder stream is washed to remove residual hemicellulose sugars. Optionally, the hemicellulose sugar stream is washed to remove residual lignocellulose components. A system for separating solids, such as the lignocellulose remainder stream, from liquids, such as the hemicellulose sugar stream, following hemicellulose extraction is presented in FIG. 9. This system can comprise at least one solid-liquid separation device. In some examples, the system comprises at least one re-slurry tank. More than one solid-liquid separation and re-slurry step can be conducted, optionally with the wash liquid applied in a counter current manner. The system can comprise 1, 2, 3, 4, 5, or 6 steps of solid-liquid separation followed by re-slurry steps. Solid-liquid separation devices may be selected from bent screens, sedimentation tanks, centrifuges, and hydrocyclones. In some examples, the final wash step is conducted in a centrifuge. The liquid collected at the heaviest load may be transferred to the feed of the extraction liquid.

The lignocellulose remainder stream may be separated from the hemicellulose sugar stream by means of a vacuum belt filter. Vacuum belt filter systems are commercially available from various suppliers, including, for example, Pannevis, BHS-Sonthofen Inc. and FLSmidth. In some examples, the extraction slurry is continuously fed over a moving belt. As the belt moves, vacuum may be applied to remove liquids and create a filtration cake resting on the moving belt. Optionally, the belt passes through a wash zone. Optionally, the belt passes through a drying zone. A wash zone may comprise nozzles that spray a wash fluid on the filtration cake (i.e., the lignocellulose remainder stream) to rinse residual hemicellulose sugars from the lignocellulose remainder stream, thereby increasing the recovery of hemicellulose sugars. The temperature of the extraction slurry and wash fluid may be about 20-100° C., such as 30-90° C., 35-85° C., 35-80° C., 40-80° C., 50-80° C., 40-75° C., or 55-75° C. Optionally, the wash fluid is water. The flow of the wash fluid can be about 0.25, 0.3, 0.4, 0.5, 0.6, 0.7, 0.8, 0.9, or 1 compared to the flow of the extraction slurry. In some examples, less than 40%, less than 30%, less than 20%, less than 10%, less than 5%, less than 4%, less than 3%, less than 2.5%, less than 2%, less than 1.5%, or less than 1% of the solids remain in the hemicellulose sugar stream. In some examples, the belt is rolled over a roller to cause the filtration cake (i.e., the lignocellulose remainder stream) to fall off. Optionally, residual solids are scraped off the belt with scrapers. More than about 60%, more than about 70%, more than about 80%, more than about 90%, or more than about 95% of the solids in the extraction slurry can be recovered in the lignocellulose remainder stream. After removal of the lignocellulose remainder stream, the belt may be rolled back to the starting rollers at the beginning of the line. A vacuum belt may be fabricated of various materials using different methods of cloth production and may be woven or non-woven. Fabrication may be optimized to produce the desired porosity, thickness, and air permeability.

A system described herein may comprise a refining unit in fluid communication with the extraction unit, wherein the refining unit is configured to receive the hemicellulose sugar stream and an amine extractant, and wherein the amine extractant removes impurities from the hemicellulose sugar stream to produce a refined hemicellulose sugar stream. Optionally, the hemicellulose sugar stream is extracted with an amine extractant counter-currently, e.g., the hemicellulose sugar stream flows in a direction opposite to the flow of the amine extractant. The refining unit may comprise a mixer-settler device, a stirred tank, a liquid-liquid separation centrifuge, or a column, wherein the mixer-settler device, stirred tank, liquid-liquid separation centrifuge, or column is equipped with a liquid feed device to receive the hemicellulose sugar stream from the extraction unit. The refining unit can be equipped with an inlet to receive the amine extractant. Optionally, the amine extraction is conducted in a mixer-settler device, wherein the mixer-settler device can be designed to minimize emulsion formation, thereby reducing phase separation time. A mixer-settler may comprise a first stage that mixes the phases together followed by a quiescent settling stage that allows the phases to separate by gravity. Various mixer-settlers known in the art can be used. In some examples, phase separation may be enhanced by incorporating a suitable centrifuge with the mixer-settler. Optionally, both mixing and separation may be conducted in a liquid-liquid separation centrifuge. Liquid-liquid separation centrifuges are commercially available from various suppliers, including, for example, Rousselet Robatel Inc. and US Centrifuge Systems LLC. The amine extraction can be conducted at any temperature at which the amine is soluble, such as 50-70° C. Optionally, the amine extraction comprises more than one extraction step (e.g., 2, 3, or 4 steps). The ratio of the amine extractant stream (organic stream) to the hemicellulose sugar stream (aqueous stream) can range from about 0.5:1 to about 5:1 weight/weight, such as about 0.5:1, about 1:1, about 1.5:1, about 2:1, about 2.5:1, about 3:1, about 3.5:1, about 4:1, about 4.5:1, or about 5:1. In some examples, the ratio of the organic stream to the aqueous stream is about 1.5-4.0:1 weight/weight. The refining unit may further comprise at least one outlet for removing the refined hemicellulose sugar stream. In some examples, the refining unit further comprises column or batch units for contacting the hemicellulose sugar stream with ion exchange resins or activated carbon to further polish the refined sugar solution. In some examples, the outlet is in fluid communication with a fermentation unit. The refining unit may comprise second outlet for removing the organic stream comprising the amine extractant. In some examples, the organic stream is treated and the resultant purified amine extractant recycled back to the refining unit.

A system described herein may comprise a sensing unit in fluid communication with the refining unit to analyze the refined hemicellulose sugar stream. The sensing unit may analyze the refined hemicellulose sugar stream continuously or in batches. In some examples, the sensing unit comprises a pH probe. Optionally, if the pH probe detects that the pH of the refined hemicellulose sugar stream is too acidic, such as pH less than about 3.0, the sensing unit may divert the stream away from the fermentation unit. In some examples, if a pH probe detects that the pH of the refined hemicellulose sugar stream is too acidic, the sensing unit is configured to raise the pH of the solution, for example, by addition of ammonia. In some examples, the sensing unit analyzes color of the refined hemicellulose sugar stream, for example, using a spectrophotometer. If the light absorbance at a particular wavelength is determined to be too high, the sensing unit may divert the stream away from the fermentation unit. In some examples, the sensing unit analyzes conductivity of the refined hemicellulose sugar stream, for example, using a conductivity probe. If the conductivity is determined to be too high, such as conductivity greater than 10,000 microS/cm, the sensing unit may divert the stream away from the fermentation unit. In some examples, the sensing unit analyzes density of the refined hemicellulose sugar stream, for example, using a refractometer. If the density is determined to be too high or too low, such as a density corresponding to a sugar concentration outside the range of 50 g/L to 300 g/L, the sensing unit may divert the stream away from the fermentation unit, or may cause the addition of water to dilute the stream. The sensing unit may be configured to analyze concentration of one or more components of the refined hemicellulose sugar stream, wherein the one or more components are selected from xylose, arabinose, hexoses, glucose, galactose, mannose, fructose, disaccharides, oligosaccharides, ash, phenolic compounds, furfural, and hydroxymethylfurfural. Any concentration outside the ranges described for the subject methods and compositions may cause the sensing unit to divert the stream away from the fermentation unit, or to correct the concentration by suitable compensation or dilution. Any stream diverted from the fermentation unit may be further refined or utilized in some other process of the plant.

A system described herein may comprise a fermentation unit in fluid communication with the refining unit to receive the refined hemicellulose sugar stream, wherein the fermentation unit is configured to contain a fermentation feedstock comprising the refined stream and a microorganism, wherein the microorganism facilitates production of the xylitol from a monosaccharide in the refined hemicellulose sugar stream to produce a fermentation broth. The fermentation unit may comprise a tank equipped with at least one aqueous feed inlet to receive the refined hemicellulose sugar stream. Optionally, the fermentation unit can be temperature controlled, such that the fermentation unit maintains a given fermentation temperature within ±10° C., within ±8° C., within ±5° C., within ±4° C., within ±3° C., or within ±2° C. Optionally, the fermentation unit comprises one or more sensors, such as a temperature sensor, a density sensor, or a pH sensor. Optionally, the fermentation unit comprises a density sensor, such as a refractometer, such that the specific gravity of the fermentation broth can be measured. A change in the density of the fermentation broth above or below a certain threshold may indicate that the fermentation has consumed a desired concentration of hemicellulose sugars. A tank of the fermentation unit can be equipped with at least one outlet, such that the fermentation broth can be removed via the at least one outlet.

A system described herein may comprise a xylitol refining unit, wherein the xylitol refining unit is configured to remove the xylitol from the fermentation broth. The xylitol refining unit can be in fluid communication with the fermentation unit. In some examples, the xylitol refining unit comprises one or more filters, such as microfilters, ultrafilters, and nanofilters. Optionally, the xylitol refining unit comprises three stages of filtration, such that the fermentation broth is subjected to microfiltration, ultrafiltration, and nanofiltration. The one or more filters may be in fluid communication with one or more columns, wherein the one or more columns may contain activated carbon, such as granulated active carbon, or an ion exchange resin, such as strongly acidic cation resin, weakly basic anion resin, or mixed bed resin. Optionally, the one or more columns are in fluid communication with an evaporation unit, wherein the evaporation unit is configured to evaporate water from the solution, thereby increasing the concentration of dissolved solids. Optionally, the xylitol refining unit comprises a xylitol crystallization unit. The xylitol crystallization unit can be in fluid communication with the evaporation unit. In some examples, the xylitol crystallization unit comprises a means for agitating the solution. Optionally, the xylitol crystallization is temperature controlled, such that the temperature of the unit can be gradually cooled. The xylitol crystallization unit may further comprise an inlet for receiving ethanol. In some examples, ethanol is added to the solution in the xylitol crystallization unit to assist xylitol crystallization. In some examples, the xylitol crystallization unit is configured to receive feed solution from the evaporation unit in batch or continuous mode. The xylitol crystallization unit may comprise a screen or filter to facilitate the separation of xylitol crystals from the mother liquor by filtration, or may be in fluid communication with a filter or centrifuge configured to receive the crystallization slurry. The separated xylitol crystals can be re-dissolved, and the resulting xylitol solution transferred to a xylitol polishing unit. In some examples, the xylitol polishing unit comprises an ion exchange resin, such as a SAC, WBA, or MB resin. Optionally, the xylitol polishing unit comprises active carbon, such as granulated active carbon.

Figure 2C:
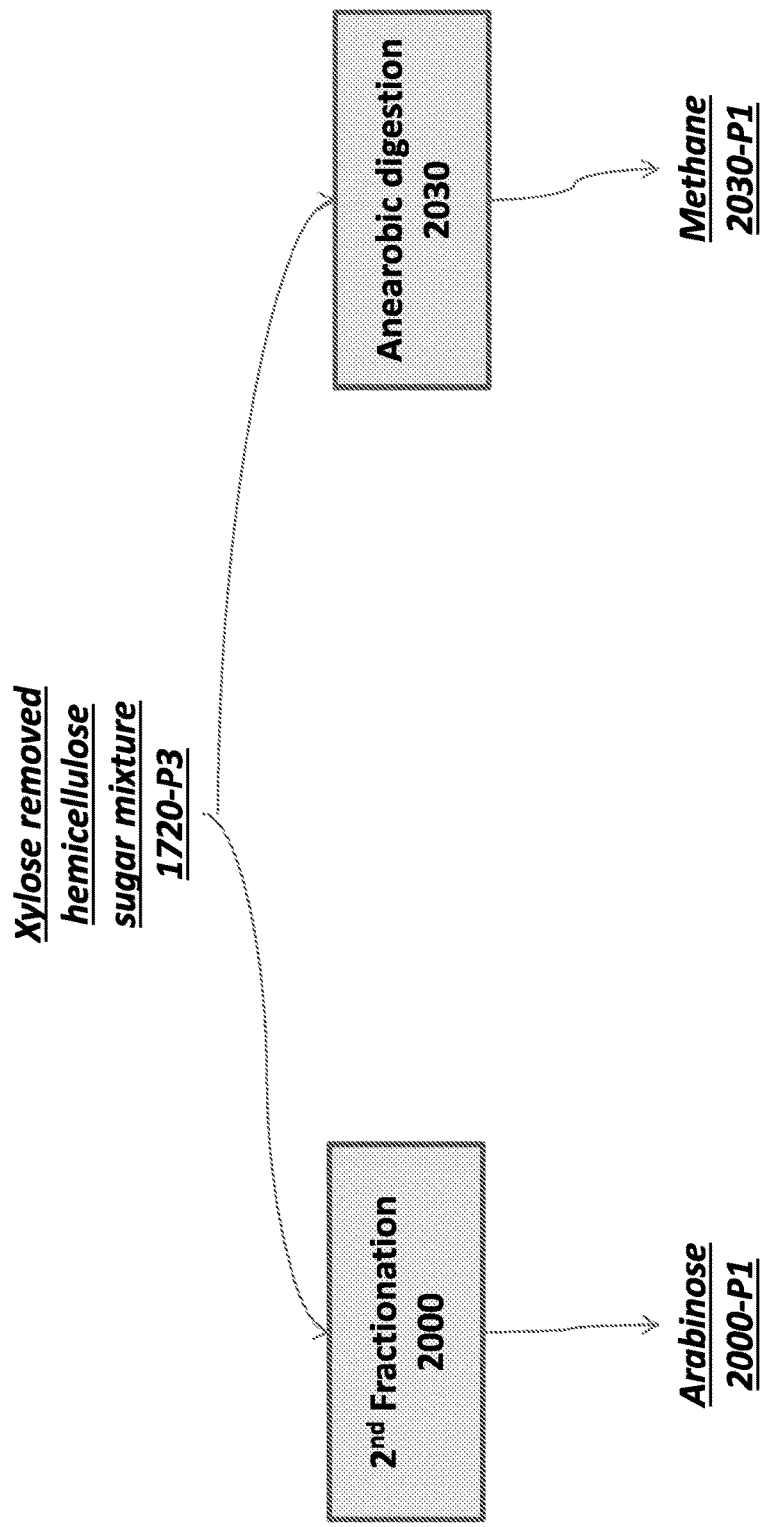
FIG. 2C illustrates a schematic diagram of exemplary processes to convert a xylose removed hemicellulose sugar mixture to downstream products such as arabinose and methane.

In some examples, the described units are connected such that mass is transferred through sequential process steps. The solid feeding unit can transfer solid bagasse mass to a sizing mill either in batch or continuously. The sizing unit may be configured to transfer either in batch or continuously sized bagasse mass to the wash unit. This wash unit (1770) may be connected such that washed bagasse solid mass is transferred to the hemicellulose extraction unit either continuously or batch-wise. Optionally, the wash unit is also connected to a waste stream allowing removal of a solid waste stream comprising the removed soil and ash to a disposal location. The wash unit may optionally be connected to other process units further downstream to receive process water. The hemicellulose extraction unit (1700) may be connected to receive washed bagasse mass by solids transfer means. Optionally, the hemicellulose extraction unit is also connected at its output to the refining unit by means of liquid transfer. The hemicellulose extraction unit may also be connected to other processes that utilize the solid lignocellulose remainder stream by means of solid transfer. In some examples, the refining unit (1710) is connected by liquid transfer means to the hemicellulose extraction unit, feeding it extraction liquor. The refining unit can be connected by means of liquid transfer to a fermentation unit (1900), feeding it with the refined hemicellulose sugar stream as feed for xylitol fermentation. Alternatively, this refining unit is connected to a xylose fractionation unit (1720 and 1837) by means of liquid transfer. A schematic diagram of exemplary conversion processes to convert a xylose enriched hemicellulose sugar mixture (1720-P1) to downstream products is provided in FIG. 2A. The xylose fractionation unit may be connected by means of liquid transfer to a fermentation unit (1900), feeding it a xylose enriched sugar mixture for the production of xylitol. The xylitol can be refined in a xylitol refining unit (1920). The xylose fractionation unit is optionally connected alternatively or in addition with a xylose crystallization unit (1841) for the production of crystalline xylose (1841-P1). The crystalline xylose can be used in a catalytic conversion unit (1910) for the catalytic conversion of xylose to xylitol, optionally crystallized in a xylitol crystallization unit (1915) to produce xylitol (1950-P1). The xylose fractionation unit may optionally be alternatively or additionally connected to another process (1780) for the chemical conversion of $C_5$ sugars to furfural (1780-P1). In some examples, the xylose fractionation unit is also connected by liquid transfer means with another process capable of using the xylose depleted sugar mixture as feed for biochemical or chemical conversion of the sugar mixture to products. A schematic diagram of exemplary processes to convert a xylose depleted sugar mixture (1720-P3) to a downstream product is provided in FIG. 2C. The xylose depleted sugar mixture can undergo a second fractionation (2000) to give an arabinose product (2000-P1). The xylose depleted sugar mixture may optionally be alternatively or additionally digested in an anaerobic digestion unit (2030) to produce methane (2030-P1). In some examples, the xylose fermentation unit is connected with the xylose fractionation unit by means of liquid transfer, feeding it with a xylose enriched sugar mixture as feed. The fermentation unit may be connected to the xylitol refining unit by means of liquid transfer. In some examples, the xylitol refining unit is connected to the fermentation unit by means of liquid transfer, feeding it with a mixture comprising xylitol. The xylitol refining unit may be connected with a xylitol crystallization unit, feeding it refined and fractionated xylitol by means of liquid transfer. The xylitol refining unit may also be connected with another process capable of utilizing the stream rejected at xylitol fractionating by means of liquid transfer. The xylitol refining unit may alternatively be connected to the fermentation unit, transferring the rejected liquid stream back to the fermentation unit to recycle nutrients and residual sugars. In a preferred example, the overall system of connected units disclosed herein works in an orchestrated manner to result in an industrial system for the production of refined hemicellulose sugar mixtures, xylose, xylitol and additional products made of the same, efficiently and with positive economics.

In some examples, the flux of mass transfer of the different connections is optimized to match fluxes upstream and downstream of each flux, so that units are optimized to be used efficiently. Energy can be transferred from unit to unit such that excess heat in one unit is utilized to heat another unit. Energy use throughout all the units disclosed herein may be optimized for the overall process.

In some examples, use of water is optimized for the overall process. Excess water produced in one unit can be transferred by liquid transfer means to be utilized where water is needed in another unit. Optionally, use of acid and base is optimized for the overall process to minimize need of fresh acid or base. For example, acidic streams resulting from regeneration of cation exchange resins by acid wash are used to regenerate Weak Acid Cation exchangers and/or acidify or neutralize streams in other units.

The system may be constructed such that it can feed at least 35,000 tons (dry solid) of sugar cane bagasse per year into the system, to produce at least 7,000 tons (dry solid) of refined hemicellulose sugars per year. The system is optionally constructed such that it can produce at least 5,000 tons (dry solid) xylose per year, at least 2,000 tons (dry solid) partially depleted xylose sugar mixture per year, along with at least 24,000 tons (dry solid) lignocellulose remainder. The system is optionally constructed such that it produces waste water at about 250 gpm.

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims. All publications, patents, and patent applications cited herein are hereby incorporated by reference in their entirety for all purposes.

Example 1—Analyses of Ash of Louisiana Bagasse Feedstock Before and after Soil and Ash Removal The ash fraction of a sample of bagasse taken from a pile at a sugar mill in Louisiana was evaluated by ashing of samples in a microwave furnace (3.1. CEM Phoenix™ Microwave Muffle Furnace). The bagasse sample was found to contain 13.4% ash.

TABLE 1A

Ash results after different treatments to remove soil and ash

| Sample | % Ash |
| --- | --- |
| Louisiana Sample R1 | 13.12 |
| Louisiana Sample A | 17.81 |
| Louisiana Sample R2 | 13.38 |
| Sample R1 washed with water | 12.78 |
| Sample A washed with water | 17.16 |
| Sample R2, 1 shear treatment, 1 pressure wash | 6.67 |
| Sample A, 2 shear treatments, 2 pressure wash | 2.52 |
| Sample R2, 6 shear treatments, 6 pressure wash | 2.68 |
| Sample R2, 8 shear treatments, 8 pressure wash | 2.26 |

The results summarized in Table 1A demonstrate the high ash present in Louisiana bagasse obtained from different sugar mills and different sampling times. The results also show that to achieve effective removal of soil and ash it is essential to apply several cycles of shear treatment and washing with high pressure to cause the removal of stones, sand and sols of ash compound. The remaining bagasse still holds 2-3% of "true" ash, that is related to metal cations and other elements associated at molecular level in the cell structure.

Another sample of bagasse was milled and de-ashed, and the samples sieved through a series of screens before and after de-ashing.

TABLE 1B

De-soiling/De-ashing of bagasse

| | | Ground Raw Bagasse | | De-Ashed Bagasse | |
| --- | --- | --- | --- | --- | --- |
| Screen Size | Screen Size (mm) | % ash | Fiber Length | % ash | Fiber Length |
| on 6 mesh | 340 | 0.3 | 1.0-15.0 | 0 | |
| on 12 | 170 | 5 | 2.0-15.0 | 1 | 5.0-10.0 |
| on 16 | 120 | 9.5 | 1.0-10.0 | 5.4 | 2.0-10.0 |
| on 20 | 80 | 12.7 | 1.0-10.0 | 6 | 1.0-5.0 |
| on 30 | 60 | 57.3 | <1.0-5.0 | 71.1 | 1.0-5.0 |
| thru 30 | <60 | 15.4 | <1.0 | 16.5 | <1.0 |

The results summarized in Table 1B demonstrate the ability to remove by industrial means most of the soil and ash from bagasse feedstock by shear treatment and high pressure wash, while still maintaining ~85% of the original feedstock at size greater than 30 mesh, that allows further handling of the washed material.

Example 2—Characterization of Different Bagasse Samples

In practical operational conditions, an industrial process should be capable of utilizing bagasse of varying storage history, as bagasse may be stored in piles by the sugar mill for over 1, 3, 5, or even over 10, 12, or 14 years. Moreover, sugarcane harvesting season is about 3 months, with sugar production being a seasonal process, while a biorefinery should operate year round. It is further advantageous that excess leaves and field debris can be handled in the same process to harvest the xylose portion within and to eliminate a bottleneck of debris handling for the farmer and/or the sugar mill. Bagasse samples that have been stored more than a year, new bagasse and field debris were characterized. "New Bagasse" samples were from piles accumulated for up to 4 years ago, "Old Bagasse" samples were from piles accumulated 5-15 years ago, and "Leaves" and other field debris were de-soiled/de-ashed according to Example 1. The washed samples were heated to 160° C. for 60 minutes to extract hemicellulose sugars. Lignocellulosic biomass before and after extraction was analyzed according to NREL/TP-510-42622. Both solid phases and the hydrolysis liquor were analyzed for carbohydrate composition by HPAE-PAD. The results are summarized in Table 2. The results indicate that all samples can be handled by the methods and systems disclosed herein.

TABLE 2

Composition of different bagasse and field debris samples

| | New Bagasse | | Old Bagasse | | Leaves | |
| --- | --- | --- | --- | --- | --- | --- |
| Dry Basis, % w/w | Pre-Hydrolysis Solids | Post-Hydrolysis Solids | Pre-Hydrolysis Solids | Post-Hydrolysis Solids | Pre-Hydrolysis Solids | Post-Hydrolysis Solids |
| Hemicellulose | 28.11 | 4.39 | 19.32 | 3.58 | 30.60 | 3.04 |
| Cellulose | 40.26 | 49.74 | 47.39 | 48.26 | 36.19 | 40.51 |
| Klason lignin | 20.52 | 27.08 | 26.45 | 31.21 | 19.07 | 30.76 |
| Ash | 2.1 | 6.49 | 2.27 | 10.08 | 3.56 | 3.89 |
| TOTAL | 91.36 | 88.24 | 95.93 | 96.24 | 89.97 | 78.95 |
| Individual Sugars Dry Basis, % w/w | Pre-Hydrolysis Solids | Post-Hydrolysis Solids | Pre-Hydrolysis Solids | Post-Hydrolysis Solids | Pre-Hydrolysis Solids | Post-Hydrolysis Solids |
| trehalose | 0 | 0 | 0 | 0 | 0.00 | 0.00 |
| arabinose | 2.33 | 0.3 | 0.24 | 0.09 | 3.87 | 0.35 |
| galactose | 0.5 | 0.06 | 0.05 | 0.05 | 0.74 | 0.15 |
| glucose | 40.26 | 49.74 | 47.39 | 48.26 | 36.19 | 40.51 |
| xylose | 24.81 | 3.31 | 18.45 | 2.69 | 25.41 | 2.03 |
| mannose | 0.47 | 0.72 | 0.58 | 0.74 | 0.57 | 0.50 |

TABLE 2-continued

Composition of different bagasse and field debris samples

| | | | | | | |
|---|---|---|---|---|---|---|
| fructose | 0.33 | 0.49 | 0.46 | 0.53 | 0.49 | 0.67 |
| isomaltose | 0 | 0 | 0 | 0 | 0.00 | 0.00 |
| cellobiose | 0 | 0 | 0 | 0 | 0.00 | 0.00 |
| maltose | 0 | 0 | 0 | 0 | 0.00 | 0.00 |

| Aq conc; % w/w | Hydrolysate | Hydrolysate | Hydrolysate |
|---|---|---|---|
| trehalose | 0 | 0 | 0.00 |
| arabinose | 0.08 | 0.005 | 0.12 |
| galactose | 0.02 | 0.005 | 0.02 |
| glucose | 0.12 | 0.088 | 0.25 |
| xylose | 0.58 | 0.326 | 0.59 |
| mannose | 0.03 | 0.006 | 0.01 |
| fructose | 0.02 | 0.003 | 0.03 |
| isomaltose | 0 | 0 | 0.00 |
| cellobiose | 0 | 0 | 0.00 |
| maltose | 0 | 0 | 0.00 |
| xylose/monomers | 68.2% | 75.3% | 57.1% |
| C6/xylose | 32.8% | 31.3% | 54.7% |

Example 3—Shredding of Louisiana Bagasse

Bagasse was received from a sugar mill in lumps. The biomass was shredded using a wood chipper and screened through a series of sieves. Typical particle sizes of the crushed/shredded bagasse are presented in Table 3.

TABLE 3

Particle size of shredded bagasse

| Mesh | Micron | % On |
|---|---|---|
| 12 | 1680 | 6.2 |
| 20 | 841 | 3.6 |
| 30 | 595 | 16.5 |
| 40 | 420 | 20.4 |
| 60 | 250 | 21.6 |
| 80 | 177 | 10.2 |
| 100 | 149 | 5.9 |
| 120 | 125 | 2.4 |
| 200 | 74 | 6.5 |
| Thru | 74 | 7.3 |
| | | 100.6 |

Example 4—Extraction, Refinement, and Fractionation of Biomass

Bagasse was shredded in a wood shredder. The shredded bagasse was washed in a temperature controlled tank and the washed bagasse (60 lbs, dry base) treated with an aqueous solution containing 0.5% $H_2SO_4$ (wt/wt) at a liquid to solid ratio of 14.2:1. The average temperature of the temperature controlled tank was maintained at 130-135° C. for 3 hours. The solution was circulated by pumping. The resulting liquor was collected, and the solids were washed with water. The wash water was then used to prepare the acid solution for the next batch by adding acids as needed. The hemicellulose-depleted lignocellulose remainder stream was collected and dried.

The acidic hemicellulose sugar stream was run through a SAC column. The sugar stream was then extracted continuously in a series of mixer settlers (2 stages) with an amine extractant (30:70 trilaurylamine:hexanol). The amine extractant to sugar stream ratio was kept in the range of 2:1 to 1.5:1. The resulting aqueous phase was further purified by using a SAC resin, a WBA resin, a granulated active carbon and a mixed bed resin. The pH of the resulting stream was adjusted to 4.5 with 0.5% HCl and the sugar solution was evaporated to a concentration of ~30% DS. The resulting refined hemicellulose sugar stream contained about 7% arabinose, 2.5% galactose, 6.5% glucose, 65% xylose, 1.5% mannose, 4% fructose and 14% oligosaccharides (all % weight/total sugars). This sugar solution was further processed by fractionation on an SSMB system, resulting in a xylose rich fraction and a xylose depleted fraction. Each fraction was concentrated by evaporation. Table 4 provides a chemical analysis of the resulting xylose rich sugar solution.

TABLE 4

Chemical analysis of a xylose enriched sugar stream produced by hemicellulose sugar extraction and purification from bagasse

| PARAMETER | RESULT | UNITS |
|---|---|---|
| APPEARANCE | Colorless | |
| pH | 3.58 | |
| Saccharides | | |
| % TS (HPLC) | 68.2 | % w/w |
| Composition (HPAE-PAD) | | |
| XYLOSE | 81.84 (55.81) | %/TS (% |
| ARABINOSE | 4.38 (2.99) | %/TS (% |
| MANNOSE | 1.99 (1.36) | %/TS (% |
| GLUCOSE | 5.07 (3.46) | %/TS (% |
| GALACTOSE | 0.91 (0.62) | %/TS (% |
| FRUCTOSE | 6.15 (4.20) | %/TS (% |
| Impurities | | |
| Furfurals (GC) | <0.005 | % w/w |
| Phenols (FC) | 0.04 | % w/w |
| Metals & inorganics (ICP) | | |
| Ca | <2 | ppm |
| Cu | <2 | ppm |
| Fe | <2 | ppm |
| K | <2 | ppm |
| Mg | <2 | ppm |
| Mn | <2 | ppm |
| Na | <2 | ppm |
| S | <10 | ppm |
| P | <10 | ppm |

Example 5—Extraction and Refinement of Biomass

Bagasse was shredded and de-soiled according to Examples 1 and 3 and the refined solids separated by filtration. The collected hemicellulose sugar stream was refined by first contacting with a SAC resin, followed by removal of much of the impurities by amine extraction. The refined aqueous sugar solution was further polished by contacting with a SAC resin, a WBA resin and finally evaporated to a concentration above 70% wt/wt dissolved sugars. The process was conducted at pilot scale at Virdia PDU, Danville, Va. Table 5 summarizes the sugar profile of the refined hemicellulose sugar streams.

TABLE 5

Sugar composition of a refined hemicellulose sugar stream produced by hemicellulose sugar extraction and purification from bagasse

| Sample | 1 | 2 | 3 | 4 | 5 | 6 | 7 | 8 | 9 | 10 | Average |
|---|---|---|---|---|---|---|---|---|---|---|---|
| Total Sugars (g) | 87.53 | 87.53 | 86.68 | 89.79 | 76.02 | 87.81 | 76.25 | 71.41 | 81.11 | 88.41 | 83.25 |
| Arabinose (g) | 5.59 | 5.59 | 6.13 | 5.90 | 4.81 | 5.59 | 3.63 | 3.14 | 3.60 | 4.06 | 4.80 |
| Galactose (g) | 2.05 | 2.05 | 2.12 | 2.03 | 1.62 | 2.02 | 1.84 | 1.74 | 1.78 | 1.95 | 1.92 |
| Glucose (g) | 5.09 | 5.09 | 5.58 | 5.33 | 4.65 | 6.79 | 7.15 | 6.75 | 7.54 | 6.79 | 6.07 |
| Xylose (g) | 58.69 | 58.69 | 56.58 | 59.05 | 52.14 | 58.11 | 50.65 | 47.21 | 56.24 | 55.10 | 55.25 |
| Mannose (g) | 1.51 | 1.51 | 1.12 | 1.43 | 1.30 | 2.27 | 2.22 | 2.09 | 2.27 | 1.84 | 1.75 |
| Fructose (g) | 3.12 | 3.12 | 3.37 | 1.97 | 1.54 | 2.52 | 2.86 | 2.94 | 2.16 | 3.49 | 2.71 |

As evidenced in Table 5, a refined hemicellulose sugar stream produced from bagasse comprises, on average, 66% xylose, 6% arabinose, and 15% hexoses, all weight/weight relative to total sugars. The streams exemplified in Table 5 are thus suitable for use in the subject methods for conversion to xylitol.

Example 6—Fractionation of Refined Hemicellulose Sugar Stream

Figure 6:
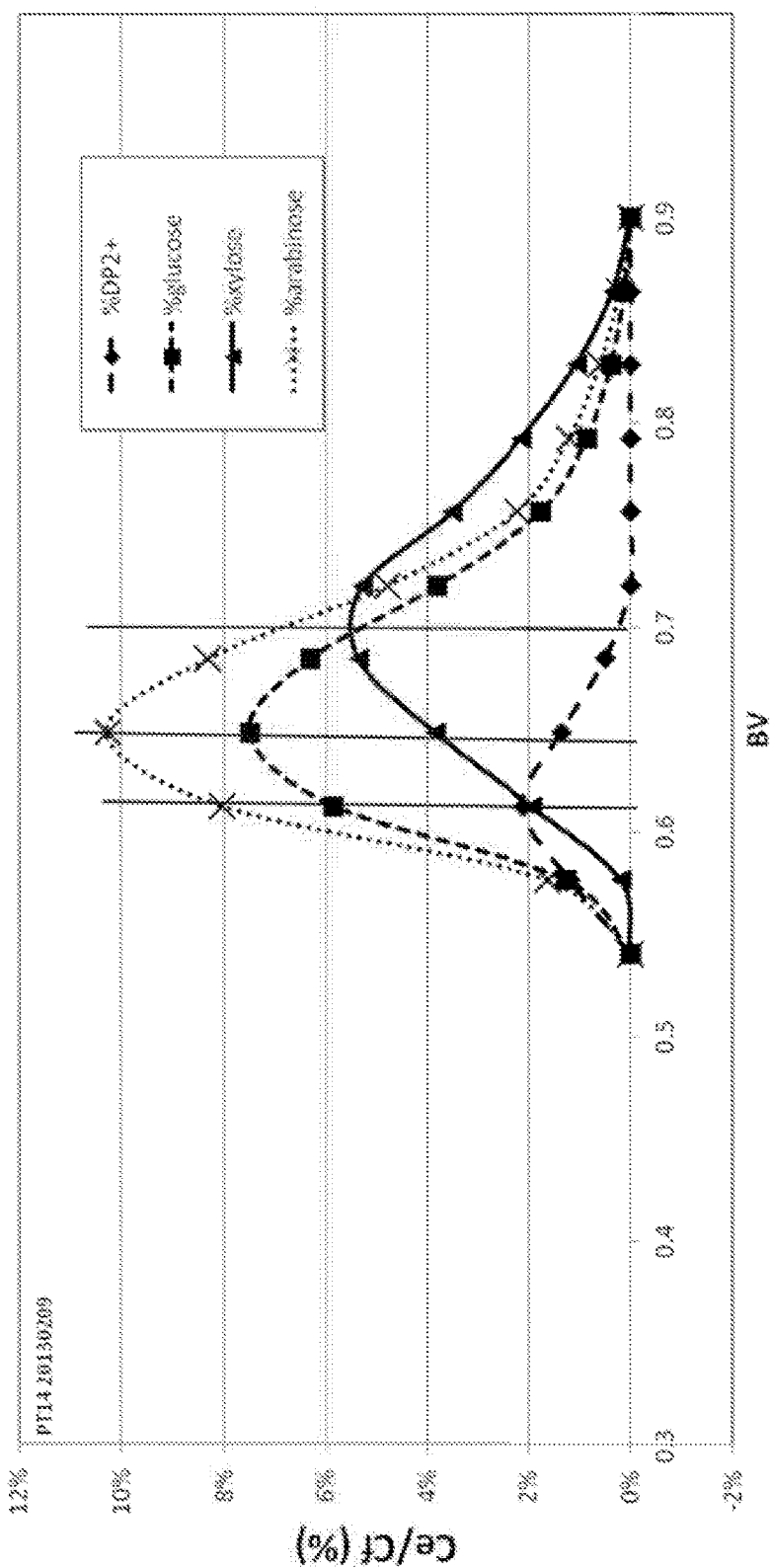
FIG. 6 illustrates results of a pulse test chromatogram showing fractionation of a hemicellulose sugar mixture to obtain xylose enriched and xylose removed sugar mixtures.

Refined hemicellulose sugar streams 1 to 10 produced according to Example 5 were fractionated by chromatography (as per PCT/US2013/039585) to produce xylose enriched extract streams 1 to 10 (Table 6A) and xylose depleted raffinate streams 1 to 10 (Table 6B). A pulse test chromatogram showing fractionation of a refined hemicellulose sugar stream is provided in FIG. 6. This pulse test demonstrates the ability to fractionate a refined hemicellulose sugar stream to obtain a xylose enriched stream and a xylose depleted stream.

TABLE 6A

Sugar composition of a xylose enriched sugar mixture produced from bagasse

| Sample | 1 | 2 | 3 | 4 | 5 | 6 | 7 | 8 | 9 | 10 | Average |
|---|---|---|---|---|---|---|---|---|---|---|---|
| Total Sugars (g) | 45.01 | 45.01 | 67.60 | 66.06 | 70.42 | 69.72 | 44.97 | 63.04 | 58.11 | 46.74 | 57.67 |
| Arabinose (g) | 0.23 | 0.23 | 3.35 | 4.38 | 3.60 | 3.91 | 1.06 | 2.16 | 1.60 | 0.96 | 2.15 |
| Galactose (g) | 0.04 | 0.04 | 0.58 | 0.96 | 0.69 | 0.73 | 0.25 | 0.76 | 0.48 | 0.20 | 0.47 |
| Glucose (g) | 0.37 | 0.37 | 3.31 | 4.52 | 3.57 | 4.16 | 1.85 | 4.08 | 3.20 | 1.36 | 2.68 |
| Xylose (g) | 39.09 | 39.09 | 57.86 | 53.33 | 60.13 | 55.34 | 38.27 | 51.98 | 50.18 | 39.89 | 48.51 |
| Mannose (g) | 0.23 | 0.23 | 0.69 | 1.32 | 0.84 | 1.91 | 0.80 | 1.64 | 1.40 | 0.88 | 1.00 |
| Fructose (g) | 0.68 | 0.68 | 1.78 | 1.55 | 1.58 | 3.67 | 2.75 | 2.40 | 1.20 | 3.40 | 1.97 |

TABLE 6B

Sugar composition of a xylose depleted sugar mixture produced from bagasse

| Sample | 1 | 2 | 3 | 4 | 5 | 6 | 7 | 8 | 9 | 10 | Average |
|---|---|---|---|---|---|---|---|---|---|---|---|
| Total Sugars (g) | 18.00 | 18.00 | 19.15 | 18.00 | 10.24 | 17.62 | 15.32 | 12.68 | 19.53 | 22.98 | 17.15 |
| Arabinose (g) | 2.32 | 2.32 | 2.42 | 1.63 | 1.14 | 1.84 | 1.21 | 1.24 | 2.07 | 2.11 | 1.83 |
| Galactose (g) | 1.36 | 1.36 | 1.32 | 1.00 | 0.63 | 1.12 | 1.07 | 0.94 | 1.53 | 1.49 | 1.18 |
| Glucose (g) | 1.88 | 1.88 | 2.02 | 1.27 | 0.89 | 1.53 | 2.54 | 2.64 | 4.79 | 3.75 | 2.32 |

TABLE 6B-continued

Sugar composition of a xylose depleted sugar mixture produced from bagasse

| Sample | 1 | 2 | 3 | 4 | 5 | 6 | 7 | 8 | 9 | 10 | Average |
|---|---|---|---|---|---|---|---|---|---|---|---|
| Xylose (g) | 2.87 | 2.87 | 3.17 | 3.82 | 2.14 | 3.78 | 3.13 | 2.51 | 4.60 | 5.02 | 3.39 |
| Mannose (g) | 0.36 | 0.36 | 0.42 | 0.28 | 0.15 | 0.29 | 0.45 | 0.46 | 0.84 | 0.80 | 0.44 |
| Fructose (g) | 0.57 | 0.57 | 0.65 | 0.51 | 0.20 | 0.19 | 0.72 | 0.46 | 0.57 | 1.07 | 0.55 |

As evidenced in Table 6A, a xylose enriched sugar mixture produced from bagasse comprises, on average, 84% xylose, 4% arabinose, and 11% hexoses, all weight/weight relative to total sugars. Some xylose enriched mixtures, such as Sample 3, have a lower concentration of hexoses (86% xylose, 5% arabinose, and 9% hexoses). On average, the samples exemplified in Table 6A are suitable for use in the subject methods for conversion to xylitol, although some of the individual samples may contain a higher than ideal ratio of xylose to hexoses. Surprisingly, fractionation of a refined hemicellulose sugar stream may not be necessary to produce a sugar stream suitable for conversion to xylitol.

As evidenced in Table 6B, a xylose depleted sugar mixture produced from bagasse comprises, on average, 20% xylose, 11% arabinose, and 26% hexoses, all weight/weight relative to total sugars.

Example 7—Sugar Composition to Feed a Fermentation Process

The refined hemicellulose sugar streams disclosed herein are particularly suitable as feed for fermenting species capable of hydrogenating xylose to xylitol with high specificity, and capable of using the C6 sugars as well as at least some of the arabinose as their energy source for proliferation. Table 7 summarizes typical refined hemicellulose sugar streams suitable to be fed for xylitol production.

TABLE 7

Sugar composition of a refined hemicellulose sugar stream suitable as feed for xylitol fermentation

| Sample | AC130418 | AC130419 | AC130420 | AC130422 | AC130423 | AC130424 | AC130502 | AC130507 | AC130508 | AC130517 | Average |
|---|---|---|---|---|---|---|---|---|---|---|---|
| Xylose (%/monomers) | 77.2 | 77.2 | 75.5 | 78.0 | 78.9 | 75.2 | 74.1 | 73.9 | 76.4 | 75.3 | 76.1 |
| Arabinose (%/monomers) | 7.4 | 7.4 | 8.2 | 7.8 | 7.3 | 7.2 | 5.3 | 4.9 | 4.9 | 5.5 | 6.6 |
| C6 sugars (%/monomers) | 15.5 | 15.5 | 16.3 | 14.2 | 13.8 | 17.6 | 20.6 | 21.2 | 18.7 | 19.2 | 17.3 |

Example 8—Xylitol Crystallization from a Model Solution

The ability to purify xylitol from a mixture containing xylitol, arabitol, and xylose by crystallization and chromatography was evaluated. Crystallization was performed in an agitated, jacketed beaker attached to a circulating water heater/cooler. A solution was made to simulate a fermentation product: 300 g of a solution containing 93.9% xylitol, 3.7% xylose, and 2.8% arabitol/arabinose was diluted to 79.2% DS, and ethanol added according to the total weight of solvent at indicated mol %. Crystallization was initiated at 65° C. by seeding with xylitol and the solution cooled to 35° C. over 16 h. Crystals were collected by filtration, washed with ethanol, dried, and analyzed for xylitol purity by HPAE-PAD. Xylitol yield and purity are summarized in Table 8. It is observed that high yield of xylitol was achieved (e.g. 77% in one crystallization), with the xylitol being 99.9% pure of reducing sugars and arabitol.

TABLE 8

Yield and purity of xylitol crystals

| % Ethanol | Xylitol yield, % | Xylitol purity, % | Residual arabitol, ppm | Residual xylose, ppm |
|---|---|---|---|---|
| 10 | 77 | 99.9 | 200 | 570 |

Example 9—Fractionation of Xylitol from the Crystallization Mother Liquor

Xylitol was fractionated from a mixture containing 43% weight/weight xylitol, 6% weight/weight arabitol, 6% weight/weight xylose, and 8% weight/weight ethanol. The composition of this mixture is representative of major components present in the crystallization mother liquor.

A pulse test was conducted utilizing 250 mL of Purolite PCR 642 (gel form, styrene divinylbenzene copolymer, functional group sulfonic acid, and mean bead size 295-335 µm). The gel was pre-conditioned with a solution containing strontium salt to make it fully in a strontium form. A 12.5 mL sample of the xylitol mixture was injected, followed by water elution at 8.33 mL/min. Effective fractionation of xylitol from the mixture was observed, with the xylose peaking at 0.61 BV, ethanol at 0.72 BV, arabitol at 0.84 BV and xylitol peaking at 0.96 BV. The pulse test results are described in FIG. 7. This pulse test demonstrates the ability to fractionate the mother liquor solution to obtain a xylitol stream, arabitol stream and reducing sugar stream.

Example 10—De-Ashing/De-Soiling of Old and New Bagasse at Pilot Scale

Figure 10:
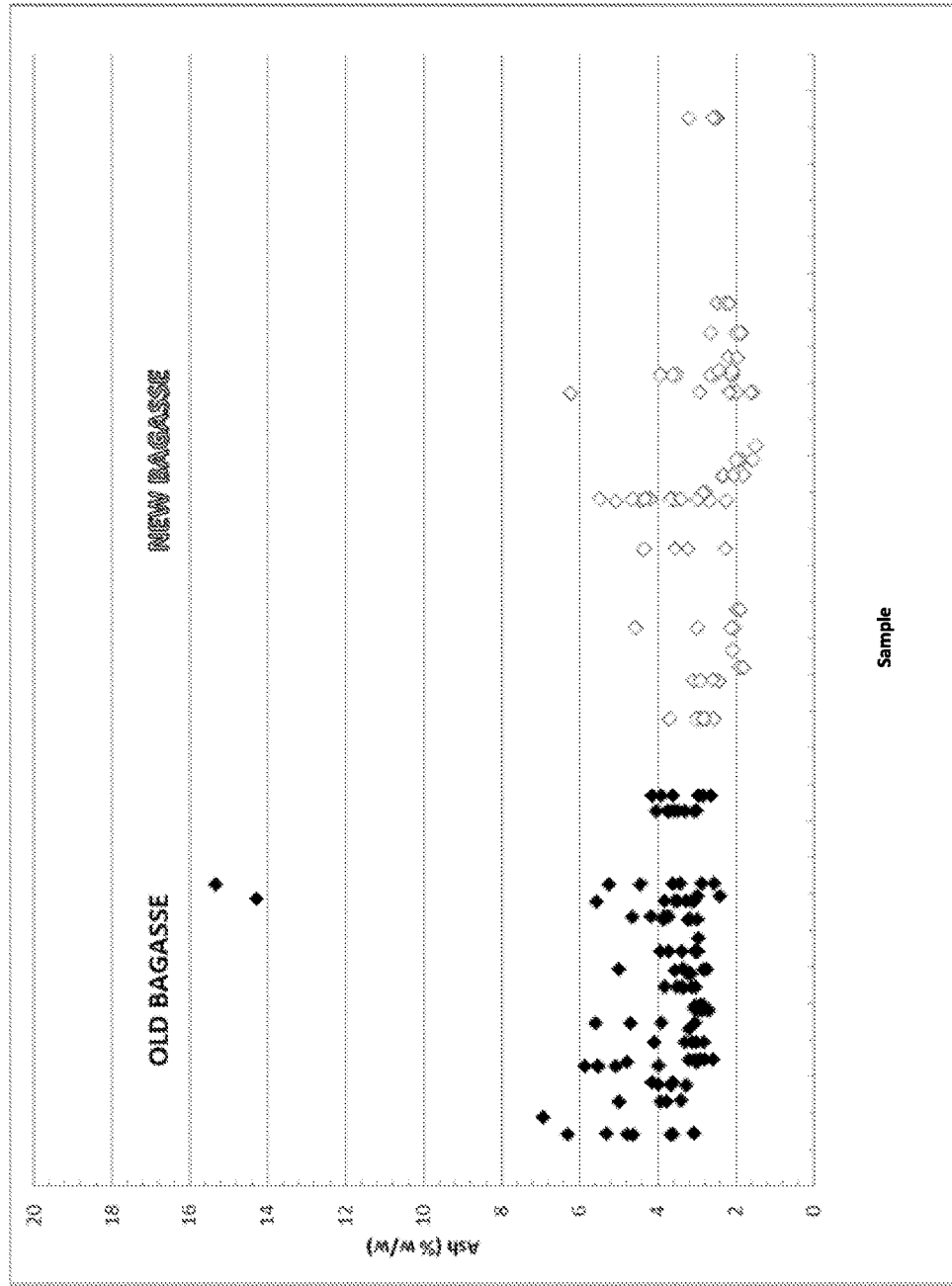
FIG. 10 illustrates residual ash content of washed bagasse samples.

A system as described schematically in FIG. 8 was constructed, comprising 4 screens (Fluidquip, DSM, Screen Service) for solid/liquid separation and a final screw press (Vincent Corporation). 40 tons of bagasse from Raceland, La. were analyzed for ash and moisture content, and found to have an ash level of 12.9±1.6% wt/wt and a moisture level of 56.6±6.6% wt/wt. Bagasse was first shredded to break up clumps and fed into the wash unit of FIG. 8. Washed and de-watered bagasse was collected daily for analysis of residual ash amounts. The daily results shown in FIG. 10 indicate that the wash system successfully removed soil from the bagasse feed to reduce the measured ash level below 6% wt/wt.

Example 11—Filtering, Washing and De-Watering Lignocellulose Remainder Stream from Hemicellulose Sugar Stream Washed bagasse was heated to extract the hemicellulose sugars in batches of 2000-3000 Lb under conditions similar to Example 4. The collected slurry was continuously fed into a 0.6 m² Stainless Steel 024 Filter (BHS Sonthofen Inc). The slurry, having a solids concentration of 7.5-8%, was fed at 70° C. at a throughput of 0.5-1.5 gal/min (average approximately 1 gal/min). The wash liquid was city water at 70° C. Polypropylene (850 μm thick, air permeability of 50 L/m²S) was used as a filtration material. Prior to filtration, the slurry was sparged with steam to increase the temperature to 70° C. The slurry was agitated and heated in the totes using the steam and an air dispersion device. The slurry was then pumped to the filter using a diaphragm pump. The filter cake was washed with hot water. The filter cake was allowed to dewater under vacuum and discharged via a 90 degree roller. The cake was analyzed for moisture, ash and for residual free sugars, with results summarized in Table 11, showing effective washing and de-watering of the lignocellulose remainder stream. The clarity of filtrate was evaluated by centrifuging a sample of the filtrate. The solid content of the mother filter was estimated as less than 0.1%, and no solid content was visualized in the wash filtrate, indicating that the solids were efficiently removed by filtration.

TABLE 11

Moisture, ash and residual sugar in the lignocellulose remainder stream

| Reference No. | Residual sugars (% wt/wt) | Moisture (% wt/wt) | Ash (% wt/wt) |
| --- | --- | --- | --- |
| 21888 | 0.4 | 73.4 | 5.5 |
| 21892 | 1.9 | 74.9 | 2.8 |
| 21896 | 0.7 | 72.9 | 3.0 |
| 21787 | 1.0 | 73.0 | 3.6 |
| 21752 | 0.7 | 72.5 | 3.0 |
| 21791 | 1.1 | 71.8 | 5.4 |
| 21795 | 0.3 | 72.2 | 4.8 |
| 21853 | 0.5 | 72.7 | 3.0 |
| 21884 | NA | 74.8 | NA |
| Average | 0.8 | 73.1 | 3.9 |
| STDV | 0.5 | 1.1 | 1.2 |

Example 12—Refining of Hemicellulose Hydrolysate Collected in Example 11

The hemicellulose hydrolysate collected in Example 11 was refined by contacting with a SAC resin followed by amine extraction. The refined aqueous solution was evaporated to strip off the solvent, then further polished by contacting with a SAC resin, a WBA resin, a MB resin, and finally evaporation to about 70% wt/wt DS. The final sugar products were analyzed and shown to have the compositions of Table 12A. Some of the material was fractionated by chromatography to enrich the xylose fraction, the composition of which is provided in Table 12B. Both samples were successfully fermented to xylitol by various microorganisms, with appropriate addition of C6 sugars (e.g., glucose) to support the proliferation of the microorganism.

TABLE 12A

Sugar composition of a refined hemicellulose sugar stream produced by hemicellulose sugar extraction and purification from bagasse

| PARAMETER | RESULT | UNITS |
| --- | --- | --- |
| APPEARANCE | Colorless, clear solution | |
| pH | 4.08 | |
| Saccharides | | |
| DS (HPLC) | 68.64 | % wt/wt |
| Degree of Polymerization (HPLC) | | |
| Monomers | 98.80 | % |
| Oligomers | 1.20 | % |
| Composition (HPAE-PAD) | | |
| XYLOSE | 57.58 | % of monomers |
| ARABINOSE | 8.09 | % of monomers |
| MANNOSE | 2.61 | % of monomers |
| GLUCOSE | 16.84 | % of monomers |
| GALACTOSE | 2.21 | % of monomers |
| FRUCTOSE | 12.67 | % of monomers |
| Impurities | | |
| Furfurals (UV) | <0.01 | % wt/wt |
| Phenols (UV) | 0.02 | ppm/DS |
| Metals & inorganics (ICP) | | |
| Ca | 11 | ppm/DS |
| Cu | <2 | ppm/DS |
| Fe | <2 | ppm/DS |
| K | <2 | ppm/DS |
| Mg | 2 | ppm/DS |
| Mn | <2 | ppm/DS |
| Na | 110 | ppm/DS |
| S | <16 | ppm/DS |
| P | <23 | ppm/DS |

Reference: DB4D01

TABLE 12B

Sugar composition of a xylose-enriched sugar stream produced by hemicellulose sugar extraction and purification from bagasse

| PARAMETER | RESULT | UNITS |
| --- | --- | --- |
| APPEARANCE | Colorless viscous liquid, crystal slurry | |
| Saccharides | | |
| DS (HPLC) | 78.80 | % wt/wt |
| Degree of polymerization (HPLC) | | |
| Monomers | 98.11 | % |
| Oligomers | 1.89 | % |
| Composition (HPAE-PAD) | | |
| XYLOSE | 83.71 | % of monomers |
| ARABINOSE | 2.97 | % of monomers |
| MANNOSE | 2.01 | % of monomers |
| GLUCOSE | 5.39 | % of monomers |
| GALACTOSE | 0.83 | % of monomers |
| FRUCTOSE | 5.09 | % of monomers |
| Impurities | | |
| Furfurals (UV) | <0.005 | % wt/wt |
| Phenols (UV) | 0.04 | ppm/DS |
| Metals & inorganics (ICP) | | |
| Ca | <2 | ppm/DS |
| Cu | <2 | ppm/DS |

TABLE 12B-continued

Sugar composition of a xylose-enriched sugar stream produced by hemicellulose sugar extraction and purification from bagasse

| PARAMETER | RESULT | UNITS |
|---|---|---|
| Fe | <2 | ppm/DS |
| K | <2 | ppm/DS |
| Mg | <2 | ppm/DS |
| Mn | <2 | ppm/DS | the extraction step. The de-ashed biomass is anticipated to be much more suitable than the feed biomass for usage as feed for energy uses, e.g. oxidative burning to produce energy directly or pyrolysis to produce bio-oil. The hemi-depleted biomass is anticipated to be an even better feed for energy purposes, as more inorganic content is removed as well as some carbohydrates, consequently the percentage of lignin is increased from an average of ~24% to an average of ~40%. The higher lignin content and lower sugar content results in higher energy density of the biomass.

TABLE 13

Raceland bagasse composition analysis after the de-ashing step and after hemicellulose extraction step

| | Moisture | | | Compositional Analysis - % dry basis | | | | | |
|---|---|---|---|---|---|---|---|---|---|
| | | | | Total | Carbohydrate Composition | | | | |
| Sample Name | (% w/w) | Ash | Lignin | carbohydrate | Glucose | Xylose | Arabinose | Galactose | Mannose |
| De-ashed 1 | 54.6 | 4.7 | 23.81 | 66.98 | 42.58 | 21.41 | 1.00 | 0.25 | 1.24 |
| De-ashed 2 | 58.5 | 4.8 | 24.03 | 66.16 | 40.62 | 22.62 | 0.97 | 0.24 | 1.22 |
| De-ashed 3 | 57.7 | 3.9 | 23.28 | 68.35 | 40.48 | 24.53 | 1.19 | 0.24 | 1.43 |
| De-ashed 4 | 55.2 | 3.6 | 23.45 | 67.41 | 39.95 | 24.02 | 1.23 | 0.25 | 1.47 |
| De-ashed 5 | 53.2 | 3.1 | 23.36 | 70.31 | 41.71 | 25.26 | 1.19 | 0.48 | 1.19 |
| Hemi-depleted 1 | 64.1 | 4.2 | 39.32 | 57.76 | 52.42 | 4.37 | 0 | 0 | 0.73 |
| Hemi-depleted 2 | 71.7 | 5.4 | 39.65 | 61.9 | 57.60 | 4.30 | 0 | 0 | 0 |
| Hemi-depleted 3 | 66.9 | 4.1 | 31.85 | 57.05 | 54.62 | 2.43 | 0 | 0 | 0 |
| Hemi-depleted 4 | 66.4 | 5.1 | 47.47 | 47.19 | 45.19 | 2.00 | 0 | 0 | 0 |
| Hemi-depleted 5 | 68.2 | 5 | 42.89 | 52.8 | 49.61 | 3.19 | 0 | 0 | 0 |

| | Compositional Analysis - % dry basis | | | | | |
|---|---|---|---|---|---|---|
| | Carbohydrate Composition | ICP Results - ppm dry basis | | | | |
| Sample Name | Fructose | S | Ca | Fe | K | Mg | Na |
| De-ashed 1 | 0.5 | 81 | 1800 | 1600 | 590 | 560 | 120 |
| De-ashed 2 | 0.49 | 67 | 980 | 1200 | 580 | 510 | 120 |
| De-ashed 3 | 0.48 | 61 | 710 | 970 | 400 | 360 | 65 |
| De-ashed 4 | 0.49 | 44 | 690 | 970 | 340 | 350 | 50 |
| De-ashed 5 | 0.48 | 44 | 800 | 830 | 240 | 320 | 120 |
| Hemi-depleted 1 | 0.24 | 780 | 120 | 130 | 88 | 63 | 500 |
| Hemi-depleted 2 | 0 | 730 | 97 | 130 | 88 | 56 | 490 |
| Hemi-depleted 3 | 0 | 2300 | 190 | 240 | 92 | 84 | 620 |
| Hemi-depleted 4 | 0 | 1900 | 150 | 180 | 82 | 67 | 650 |
| Hemi-depleted 5 | 0 | 3700 | 330 | 380 | 170 | 140 | 460 |

TABLE 12B-continued

Sugar composition of a xylose-enriched sugar stream produced by hemicellulose sugar extraction and purification from bagasse

| PARAMETER | RESULT | UNITS |
|---|---|---|
| Na | <2 | ppm/DS |
| S | <10 | ppm/DS |
| P | <10 | ppm/DS |

Reference: DB4D02

Example 13—Biomass Composition Analysis after De-Soiling Step and Hemicellulose Extraction Step at Pilot Scale Bagasse from Raceland, La. was de-ashed according to Example 10 and extracted and separated as described in Example 11. Samples of the solid biomass were collected after each process step, dried and analyzed for their composition. Table 13 summarizes the results, indicating efficient de-ashing of the solid in the de-ashing/de-soiling step, and efficient extraction of hemicellulose sugars as well as reducing much of the remaining metal elements present in biomass by extracting the physiologically bound metals at Example 14—Fermentation of a Refined Hemicellulose Sugar Stream A fermenter containing fermentation media (tryptone, 14 g; yeast extract, 7 g; potassium phosphate, dibasic, 4.2 g; sodium chloride, 7 g; magnesium sulfate, 2 g; water, 750 mL, antifoam Cognis Clerol FBA 3107, 3 drops) is sterilized as described in U.S. Pub. No. 2013/0217070. A refined hemicellulose sugar stream prepared according to the subject methods (e.g., as in Examples 5 and 7) is added (100 mL, comprising 30 g of xylose). The fermenter is inoculated with 50 mL of a starter culture of a suitable microorganism (e.g., ZUC220 or ZUC170) at 30° C., and the fermentation allowed to run at 30° C. and pH 7.0 (NH$_4$OH controlled) with agitation (800 RPM) and introduction of air at 1 LPM as described in U.S. Pub. No. 2013/0217070. The volume after inoculation is 900 mL. After 24 hours, additional refined hemicellulose sugar stream is added (185 mL, comprising 130 g of xylose). The fermentation is allowed to run for a total of 80 hours after inoculation before separating the microorganism from the xylitol stream by filtration. Xylitol is crystallized as described in Example 8. Fermentation methods of the disclosure may display a volumetric productivity of greater than 1.5 g/L/h ("A" productivity), from 1.0 to 1.5 g/L/h ("B" productivity), from 0.5 to 1.0 g/L/h ("C" productivity), or less than 0.5 g/L/h ("D" productivity). In some examples, the xylitol yield of the fermentation methods described herein is greater than 100 g/L ("A" yield), from 75 to 100 g/L ("B" yield), from 50 to 75 g/L ("C" yield), or less than 50 g/L ("D" yield). Further examples of fermentation conditions can be found, for example, in U.S. Pub. No. 2013/0217070.

Example 15—Removal of Protein and Amino Acid by the Sugar Refining Method

Protein and amino acids are usually present in biomass feedstock and can be removed from sugar solutions to avoid inhibition of some microorganisms used for industrial fermentation processes. This may be necessary when sugar cane leaves are used as feedstock, as inherently more protein and amino acids are present in leaves than in the cane. Samples of bagasse and leaves were hydrolyzed and refined as described in Example 5. Samples of bagasse, leaves, and refined hemicellulose sugar streams derived from the same were analyzed by Galbraith Laboratories, Inc. for nitrogen and protein content, with the results summarized in Table 15. It can be seen that nitrogen containing molecules have been removed efficiently in the refining process, as both samples comprise less than 200 ppm nitrogen.

TABLE 15

Nitrogen and protein analysis in biomass and refined hemicellulose sugar streams produced from same

| Sample | Nitrogen (Kjeldahl) | Protein (Wet Chemistry) |
|---|---|---|
| Bagasse | 1121 ppm | 7005 ppm |
| Sugarcane leaves | 5574 ppm | 34800 ppm |
| Refined hemicellulose sugar stream from bagasse, ca. 65% DS | 13 ppm | Not Determined |
| Refined hemicellulose sugar stream from leaves, ca. 65% DS | 147 ppm | Not Determined |

Further Embodiments of the Invention

1. A method of producing xylitol from a lignocellulose-containing biomass, comprising:
   (i) fermenting a refined hemicellulose sugar stream to produce a fermentation broth comprising xylitol; and
   (ii) recovering xylitol from the fermentation broth;
   wherein the refined hemicellulose sugar stream has been produced by a process comprising:
      (a) extracting hemicellulose sugars from the biomass, thereby obtaining a hemicellulose sugar stream and a lignocellulose remainder stream;
      (b) contacting the hemicellulose sugar stream with an amine extractant to form a mixture; and
      (c) separating from the mixture an organic stream comprising the amine extractant and at least one impurity and the refined hemicellulose sugar stream.
2. The method of embodiment 1, wherein the biomass is selected from hardwood, wood-pulp, bagasse, sugarcane leaves, birch, *eucalyptus*, corn cobs, corn stover, coconut hulls, switchgrass, and wheat straw, or a combination thereof.
3. The method of embodiment 2, wherein the biomass is selected from bagasse and sugarcane leaves, or a combination thereof.
4. The method of any one of embodiments 1 to 3, further comprising reducing ash and soil content of the biomass prior to extracting hemicellulose sugars from the biomass.
5. The method of embodiment 4, wherein the reducing comprises one or more stages of slurrying, washing, and dewatering the biomass.
6. The method of any one of embodiments 1 to 5, wherein the extracting hemicellulose sugars comprises hot water extraction.
7. The method of embodiment 6, further comprising an acid.
8. The method of embodiment 7, wherein the acid is an inorganic acid.
9. The method of embodiment 7 or 8, wherein the acid is present in an amount up to 2% weight/weight.
10. The method of any one of embodiments 6 to 9, wherein the extracting occurs at a temperature of 100 to 200° C.
11. The method of any one of embodiments 1 to 10, wherein the amine extractant comprises an amine and a diluent.
12. The method of embodiment 11, wherein the amine comprises at least 20 carbon atoms.
13. The method of embodiment 12, wherein the amine is trilaurylamime.
14. The method of any one of embodiments 11 to 13, wherein the diluent comprises an alcohol.
15. The method of embodiment 14, wherein the diluent comprises hexanol or 2-ethyl-1-hexanol.
16. The method of any one of embodiments 11 to 13, wherein the diluent comprises a $C_{6-12}$ monoalcohol, kerosene, or a mixture thereof.
17. The method of any one of embodiments 1 to 16, wherein the at least one impurity is selected from ash, acid soluble lignin, furfural, fatty acids, inorganic acids, organic acids, methanol, proteins, amino acids, glycerol, sterols, rosin acid, and waxy materials.
18. The method of any one of embodiments 1 to 17, wherein the fermentation broth further comprises a microorganism selected from naturally occurring bacteria, recombinant bacteria, naturally occurring yeast, recombinant yeast, and fungi.
19. The method of embodiment 18, wherein the microorganism is an *E. coli* strain.
20. The method of any one of embodiments 1 to 19, wherein the fermenting produces, in less than 80 hours, at least 60 grams of the xylitol per liter of the fermentation broth.
21. The method of embodiment 20, wherein the fermenting produces, in less than 80 hours, at least 100 grams of the xylitol per liter of the fermentation broth.
22. The method of any one of embodiments 1 to 21, wherein the fermenting produces the xylitol at a rate of at least 1 g/L/h.
23. The method of any one of embodiments 1 to 22, wherein the fermentation broth comprises less than 1 gram of ethanol per liter.
24. The method of any one of embodiments 1 to 23, wherein at least 70% of xylose in the biomass is converted to xylitol.
25. The method of any one of embodiments 1 to 24, wherein xylose content of the refined hemicellulose sugar stream is at least 80% the xylose content of the hemicellulose sugar stream.
26. The method of any one of embodiments 1 to 25, wherein the fermenting does not comprise xylose purified by crystallization.
27. The method of any one of embodiments 1 to 26, wherein the refined hemicellulose sugar stream comprises at least 50% xylose weight/weight relative to total dissolved sugars.

28. The method of embodiment 27, wherein the refined hemicellulose sugar stream comprises between 50 and 90% xylose weight/weight relative to total dissolved sugars.

29. A method for producing xylitol by fermentation of a refined hemicellulose sugar stream derived from a lignocellulosic hydrolysate, comprising converting xylose in the refined hemicellulose sugar stream to xylitol through fermentation by a microorganism, wherein the refined hemicellulose sugar stream comprises: 50 to 90% xylose weight/weight relative to total dissolved sugars, less than 200 ppm calcium, and furfural in an amount up to 1000 ppm.

30. The method of embodiment 29, wherein the microorganism is selected from naturally occurring bacteria, recombinant bacteria, naturally occurring yeast, recombinant yeast, and fungi.

31. The method of embodiment 30, wherein the microorganism is an *E. coli* strain.

32. The method of any one of embodiments 29 to 31, wherein the fermentation produces, in less than 80 hours, at least 60 grams of the xylitol per liter of fermentation broth.

33. The method of any one of embodiments 29 to 32, wherein the fermentation produces, in less than 80 hours, at least 100 grams of the xylitol per liter of fermentation broth.

34. The method of any one of embodiments 29 to 33, wherein the fermentation produces the xylitol at a rate of at least 1 g/L/h.

35. The method of any one of embodiments 1 to 34, wherein the refined hemicellulose sugar stream comprises less than 5% oligomers weight/weight relative to total dissolved sugars.

36. The method of any one of embodiments 1 to 35, wherein the refined hemicellulose sugar stream comprises arabinose in an amount up to 12% weight/weight relative to total dissolved sugars.

37. The method of embodiment 36, wherein the refined hemicellulose sugar stream comprises between 3 and 12% arabinose weight/weight relative to total dissolved sugars.

38. The method of any one of embodiments 1 to 37, wherein the refined hemicellulose sugar stream comprises at least 10% hexoses weight/weight relative to total dissolved sugars.

39. The method of embodiment 38, wherein the refined hemicellulose sugar stream comprises between 10 and 50% hexoses weight/weight relative to total dissolved sugars.

40. The method of embodiment 38 or 39, wherein the hexoses comprise glucose, galactose, mannose, and fructose.

41. The method of any one of embodiments 38 to 40, wherein glucose and fructose comprise at least 50% weight/weight of the hexoses.

42. The method of any one of embodiments 1 to 41, wherein the ratio of xylose to hexoses is between 1.5:1 and 5:1 weight/weight.

43. The method of any one of embodiments 1 to 42, wherein the refined hemicellulose sugar stream comprises disaccharides in an amount up to 8% weight/weight relative to total dissolved sugars.

44. The method of any one of embodiments 1 to 43, wherein the refined hemicellulose sugar stream comprises ash in an amount up to 0.25% weight/weight.

45. The method of any one of embodiments 1 to 44, wherein the refined hemicellulose sugar stream comprises phenolic compounds in amounts up to 200 ppm.

46. The method of any one of embodiments 1 to 45, wherein the refined hemicellulose sugar stream comprises furfural in an amount up to 200 ppm.

47. The method of any one of embodiments 1 to 46, wherein the refined hemicellulose sugar stream comprises less than 200 ppm calcium.

48. The method of any one of embodiments 1 to 47, wherein the refined hemicellulose sugar stream comprises nitrogen in an amount up to 1000 ppm.

49. A system for producing xylitol from a lignocellulose-containing biomass, comprising:
(i) a hemicellulose extraction unit configured to extract and hydrolyze hemicellulose from the biomass to produce a hemicellulose sugar stream and a lignocellulose remainder stream;
(ii) a refining unit in fluid communication with the extraction unit, wherein the refining unit is configured to receive the hemicellulose sugar stream and an amine extractant, and wherein the amine extractant removes impurities from the hemicellulose sugar stream to produce a refined hemicellulose sugar stream;
(iii) a sensing unit configured to analyze one or more parameters of the refined hemicellulose sugar stream;
(iv) a fermentation unit in fluid communication with the refining unit to receive the refined hemicellulose sugar stream, wherein the fermentation unit is configured to contain the refined stream and a microorganism, and wherein the microorganism facilitates production of the xylitol from a monosaccharide in the refined stream to produce a fermentation broth; and
(v) a xylitol refining unit, wherein the xylitol refining unit is configured to remove the xylitol from the fermentation broth.

50. The system of embodiment 49, further comprising a wash unit configured to remove ash and soil from the biomass, wherein the hemicellulose extraction unit is in fluid communication with the wash unit.

51. The system of embodiment 49 or 50, wherein at least 90% of xylose in the refined hemicellulose sugar stream is converted to xylitol in the fermentation unit.

52. The system of any one of embodiments 49 to 51, wherein the xylitol is produced at a rate of at least 1 g/L/h in the fermentation unit.

53. The system of any one of embodiments 49 to 52, wherein the fermentation broth comprises less than 10 g/L ethanol.

54. The system of embodiment 53, wherein the fermentation broth comprises less than 4.5 g/L ethanol.

55. The system of embodiment 53, wherein the fermentation broth comprises less than 1 g/L ethanol.

56. The system of any one of embodiments 49 to 55, wherein the biomass is selected from bagasse and sugarcane leaves, or a combination thereof.

57. The system of any one of embodiments 49 to 56, wherein the one or more parameters are selected from pH, light absorbance, conductivity, density, xylose concentration, and hexose concentration 58. A fermentation feedstock comprising:
(i) 50 to 90% xylose weight/weight relative to total dissolved sugars;
(ii) 10 to 45% hexoses weight/weight relative to total dissolved sugars;
(iii) arabinose in an amount up to 12% weight/weight relative to total dissolved sugars;
(iv) disaccharides in an amount up to 8% weight/weight relative to total dissolved sugars;
(v) furfural in an amount up to 1000 ppm; and
(vi) less than 200 ppm calcium.

59. The fermentation feedstock of embodiment 58, further comprising:
(vii) less than 1000 ppm acetic acid; and
(viii) less than 1000 ppm formic acid.
60. The fermentation feedstock of embodiment 58 or 59, further comprising a $C_{6-12}$ monoalcohol in an amount up to 100 ppm.
61. The fermentation feedstock of any one of embodiments 58 to 60, further comprising nitrogen in an amount up to 1000 ppm.
62. The fermentation feedstock of any one of embodiments 58 to 61, further comprising a microorganism.
63. A fermentation broth comprising:
(i) at least 60 g/L xylitol
(ii) less than 10 g/L ethanol;
(iii) xylose in an amount up to 50 g/L;
(iv) hexoses in an amount up to 35 g/L;
(v) furfural in an amount up to 1000 ppm; and
(vi) less than 200 ppm calcium.
64. The fermentation broth of embodiment 63, further comprising:
(vii) less than 1000 ppm acetic acid; and
(viii) less than 1000 ppm formic acid.
65. The fermentation broth of embodiment 63 or 64, further comprising a $C_{6-12}$ monoalcohol in an amount up to 100 ppm.
66. The fermentation broth of any one of embodiments 63 to 65, further comprising a microorganism.
67. A xylitol composition comprising:
(i) at least 98% xylitol weight/weight relative to total dissolved solids;
(ii) oligosaccharides in an amount up to 1% weight/weight relative to total dissolved solids; and
(iii) hexoses in an amount up to 1%.
68. The composition of embodiment 67, further comprising ash in an amount up to 0.25% weight/weight relative to total dissolved solids.
69. The composition of embodiment 67 or 68, further comprising furfural in an amount up to 1000 ppm.
70. The composition of any one of embodiments 67 to 69, further comprising an amine in an amount up to 100 ppm, and wherein the amine comprises at least 12 carbon atoms.
71. The composition of any one of embodiments 67 to 70, further comprising a $C_{6-12}$ monoalcohol in an amount up to 100 ppm.
72. The composition of any one of embodiments 67 to 71, wherein the hexoses are selected from glucose, galactose, mannose, and fructose.
73. The composition of any one of embodiments 67 to 72, further comprising less than 100 ppm arabitol.
74. The composition of any one of embodiments 67 to 73, further comprising less than 100 ppm galactitol.
75. The composition of claim 74, further comprising less than 1 ppm galactitol.
76. The composition of any one of embodiments 67 to 75, wherein the composition is derived from a hydrolyzate of a lignocellulose-containing biomass.
77. The composition of any one of embodiments 67 to 76, wherein the composition is crystalline.
78. The composition of any one of embodiments 67 to 76, wherein the composition is provided as an aqueous solution.
79. The composition of embodiment 78, wherein the aqueous solution comprises at least 50% weight/weight dissolved solids.

80. A method of producing a refined hemicellulose sugar stream suitable for conversion to xylitol, comprising:
(i) extracting hemicellulose sugars from the biomass, thereby obtaining a hemicellulose sugar stream and a lignocellulose remainder stream;
(ii) contacting the hemicellulose sugar stream with an amine extractant to form a mixture;
(iii) separating from the mixture an organic stream comprising the amine extractant and at least one impurity and a refined hemicellulose sugar stream; and
(iv) measuring concentrations of at least one of xylose, arabinose, hexoses, disaccharides, ash, acetic acid, formic acid, phenolic compounds, furfural, calcium, and nitrogen;
wherein the refined hemicellulose sugar stream is suitable for conversion to xylitol if the refined stream comprises:
(1) at least 50% xylose weight/weight relative to total dissolved sugars;
(2) at least 10% hexoses weight/weight relative to total dissolved sugars; and
(3) less than 200 ppm calcium;
and wherein the refined stream suitable for conversion to xylitol further comprises at least one characteristic selected from:
(4) arabinose in an amount up to 12% weight/weight relative to total dissolved sugars;
(5) disaccharides in an amount up to 8% weight/weight relative to total dissolved sugars;
(6) ash in an amount up to 0.25% weight/weight;
(7) less than 1000 ppm acetic acid;
(8) less than 1000 ppm formic acid;
(9) phenolic compounds in an amount up to 200 ppm;
(10) furfural in an amount up to 200 ppm; and
(11) nitrogen in an amount up to 1000 ppm;
and wherein a refined stream unsuitable for conversion to xylitol is further refined.
81. The method of embodiment 80, wherein the refined stream suitable for conversion to xylitol further comprises furfural in an amount up to 200 ppm.
82. The method of embodiment 80 or 81, wherein the refined stream suitable for conversion to xylitol further comprises arabinose in an amount up to 12% weight/weight relative to total dissolved sugars.
83. The method of any one of embodiments 80 to 82, wherein the refined stream suitable for conversion to xylitol further comprises disaccharides in an amount up to 8% weight/weight relative to total dissolved sugars.
84. The method of any one of embodiments 80 to 83, wherein the refined stream suitable for conversion to xylitol further comprises ash in an amount up to 0.25% weight/weight.
85. The method of any one of embodiments 80 to 84, wherein the refined stream suitable for conversion to xylitol further comprises acetic acid in an amount up to 1000 ppm.
86. The method of any one of embodiments 80 to 85, wherein the refined stream suitable for conversion to xylitol further comprises formic acid in an amount up to 1000 ppm.
87. The method of any one of embodiments 80 to 86, wherein the refined stream suitable for conversion to xylitol further comprises phenolic compounds in an amount up to 200 ppm.
88. The method of any one of embodiments 80 to 87, wherein the refined stream suitable for conversion to xylitol further comprises nitrogen in an amount up to 1000 ppm.

What is claimed is:

1. A method for producing xylitol by fermentation of a refined hemicellulose sugar stream derived from a lignocellulosic hydrolysate, the method comprising converting xylose in the refined hemicellulose sugar stream to xylitol through fermentation by a microorganism, wherein at least 70% of xylose from the hydrolysate is converted to xylitol, and wherein the refined hemicellulose sugar stream comprises: 50 to 90% xylose weight/weight relative to total dissolved sugars, at least 10% hexoses weight/weight relative to total dissolved sugars, wherein glucose and fructose comprise at least 50% weight/weight of the hexoses, nitrogen in an amount up to 1000 ppm, less than 200 ppm calcium, and furfural in an amount up to 1000 ppm.

2. The method of claim 1, wherein the hexoses comprise glucose, galactose, mannose, and fructose.

3. The method of claim 1, wherein the ratio of xylose to hexoses is between 1.5:1 and 5:1 weight/weight.

4. The method of claim 1, wherein the refined hemicellulose sugar stream further comprises arabinose in an amount up to 12% weight/weight relative to total dissolved sugars.

5. The method of claim 1, wherein the refined hemicellulose sugar stream further comprises less than 5% oligomers weight/weight relative to total dissolved sugars.

6. The method of claim 1, wherein the refined hemicellulose sugar stream further comprises ash in an amount up to 0.25% weight/weight.

7. The method of claim 1, wherein the refined hemicellulose sugar stream further comprises phenolic compounds in amounts up to 200 ppm.

8. The method of claim 1, wherein the refined hemicellulose sugar stream further comprises furfural in an amount up to 200 ppm.

9. The method of claim 1, wherein the xylose has not been purified by crystallization.

10. The method of claim 1, wherein the converting produces, in less than 80 hours, at least 60 grams of the xylitol per liter of fermentation broth.

11. The method of claim 1, wherein the converting produces the xylitol at a rate of at least 1 g/L/h.

12. The method of claim 1, wherein the converting produces less than 1 gram of ethanol per liter of fermentation broth.

13. A method of producing xylitol from a lignocellulosic hydrolysate, comprising:
  (i) extracting hemicellulose sugars from the lignocellulosic hydrolysate, thereby obtaining a hemicellulose sugar stream and a lignocellulose remainder stream;
  (ii) contacting the hemicellulose sugar stream with an amine extractant to form a mixture;
  (iii) separating from the mixture an organic stream comprising the amine extractant and at least one impurity and a refined hemicellulose sugar stream, the refined hemicellulose stream comprising nitrogen and furfural in an amount up to 1000 ppm, less than 200 ppm calcium, 50 to 90% xylose weight/weight relative to total dissolved sugars, and at least 10% hexoses weight/weight relative to total dissolved sugars, wherein glucose and fructose comprise at least 50% weight/weight of the hexoses;
  (iv) fermenting the refined hemicellulose sugar stream to produce a fermentation broth comprising xylitol by converting xylose in the refined hemicellulose sugar stream to xylitol; and
  (v) recovering xylitol from the fermentation broth, wherein at least 70% of xylose in the lignocellulosic hydrolysate is converted to xylitol.

* * * * *